(12) United States Patent
Newberry

(10) Patent No.: US 12,376,802 B2
(45) Date of Patent: *Aug. 5, 2025

(54) SYSTEM AND METHOD FOR HEALTH MONITORING INCLUDING A USER DEVICE AND BIOSENSOR

(71) Applicant: Trilinear BioVentures, LLC, Huntsville, AL (US)

(72) Inventor: Robert Steven Newberry, New Hope, AL (US)

(73) Assignee: Trilinear BioVentures, LLC

( * ) Notice: Subject to any disclaimer, the term of this patent is extended or adjusted under 35 U.S.C. 154(b) by 1176 days.

This patent is subject to a terminal disclaimer.

(21) Appl. No.: 17/127,266

(22) Filed: Dec. 18, 2020

(65) Prior Publication Data

US 2021/0137466 A1 May 13, 2021

Related U.S. Application Data

(63) Continuation-in-part of application No. 15/718,721, filed on Sep. 28, 2017, now Pat. No. 10,517,515, and (Continued)

(51) Int. Cl.
*A61B 5/1455* (2006.01)
*A61B 5/00* (2006.01)
(Continued)

(52) U.S. Cl.
CPC .......... *A61B 5/7278* (2013.01); *A61B 5/0022* (2013.01); *A61B 5/01* (2013.01); *A61B 5/0205* (2013.01); *A61B 5/02416* (2013.01); *A61B 5/1118* (2013.01); *A61B 5/14532* (2013.01); *A61B 5/14546* (2013.01);
(Continued)

(58) Field of Classification Search
CPC .................................................. A61B 5/1455
See application file for complete search history.

(56) References Cited

U.S. PATENT DOCUMENTS 4,913,150 A   4/1990  Cheung et al.
5,115,133 A   5/1992  Knudson
(Continued)

FOREIGN PATENT DOCUMENTS

CN   102609627 A    7/2012
EP   2017001250 A1  1/2017
(Continued)

OTHER PUBLICATIONS

Alonso et al. "The nitric oxide-endothelin-1 connection." Heart Failure Review, 8, 107-115 (2003).
(Continued)

*Primary Examiner* — Marjan Fardanesh
(74) *Attorney, Agent, or Firm* — Polsinelli PC

(57) ABSTRACT

A biosensor unit is coupled to a user device and may communicate with the user device over a short range wireless or wired interface. The biosensor unit includes an optical sensor used to obtain a plurality of PPG signals. The PPG signals are used to obtain an oxygen saturation level, a heart rate and a respiration rate of a user. The PPG signal may also be used to obtain a nitric oxide (NO) level and glucose level of the user. The user device may generate a graphical user interface to display the biosensor data to a user.

20 Claims, 31 Drawing Sheets

Related U.S. Application Data a continuation-in-part of application No. 15/680,991, filed on Aug. 18, 2017, now Pat. No. 9,968,289, said application No. 15/718,721 is a continuation of application No. 15/622,941, filed on Jun. 14, 2017, now Pat. No. 9,788,767, application No. 17/127,266 is a continuation-in-part of application No. 15/462,700, filed on Mar. 17, 2017, now Pat. No. 10,500,354, and a continuation of application No. 15/404,117, filed on Jan. 11, 2017, now Pat. No. 10,932,727, which is a continuation of application No. 15/400,916, filed on Jan. 6, 2017, now Pat. No. 10,750,981, and a continuation-in-part of application No. 15/276,760, filed on Sep. 26, 2016, now Pat. No. 9,636,457, and a continuation-in-part of application No. 15/275,444, filed on Sep. 25, 2016, now Pat. No. 9,642,538, and a continuation-in-part of application No. 15/275,388, filed on Sep. 24, 2016, now Pat. No. 9,642,578, and a continuation-in-part of application No. 14/866,500, filed on Sep. 25, 2015, now Pat. No. 10,321,860.

(60) Provisional application No. 62/457,138, filed on Feb. 9, 2017.

(51) Int. Cl.
| | | |
|---|---|---|
| *A61B 5/01* | (2006.01) | |
| *A61B 5/0205* | (2006.01) | |
| *A61B 5/024* | (2006.01) | |
| *A61B 5/11* | (2006.01) | |
| *A61B 5/145* | (2006.01) | |
| *A61M 5/142* | (2006.01) | |
| *A61M 5/172* | (2006.01) | |
| *G16H 40/63* | (2018.01) | |
| *G16H 40/67* | (2018.01) | |

(52) U.S. Cl.
CPC ........ *A61B 5/1455* (2013.01); *A61B 5/14551* (2013.01); *A61B 5/14552* (2013.01); *A61B 5/4839* (2013.01); *A61B 5/4845* (2013.01); *A61B 5/6817* (2013.01); *A61B 5/7275* (2013.01); *A61B 5/742* (2013.01); *A61B 5/743* (2013.01); *A61M 5/14248* (2013.01); *A61M 5/1723* (2013.01); *G16H 40/63* (2018.01); *G16H 40/67* (2018.01); *A61B 5/0008* (2013.01); *A61B 5/6826* (2013.01); *A61B 2560/0223* (2013.01); *A61M 2205/3303* (2013.01); *A61M 2205/3313* (2013.01); *A61M 2205/3368* (2013.01); *A61M 2205/3553* (2013.01); *A61M 2205/3584* (2013.01); *A61M 2205/505* (2013.01); *A61M 2230/06* (2013.01)

(56) References Cited

U.S. PATENT DOCUMENTS

| | | | |
|---|---|---|---|
| 5,269,310 | A | 12/1993 | Jones et al. |
| 5,358,703 | A | 10/1994 | Lai |
| 5,515,847 | A | 5/1996 | Braig et al. |
| 5,673,692 | A | 10/1997 | Schulze et al. |
| 5,823,966 | A | 10/1998 | Buchert |
| 5,947,911 | A | 9/1999 | Wong et al. |
| 5,983,121 | A | 11/1999 | Tsuchiya |
| 6,087,087 | A | 7/2000 | Yonetani et al. |
| 6,280,390 | B1 | 8/2001 | Akselrod et al. |
| 6,285,896 | B1 | 9/2001 | Tobler et al. |
| 6,305,804 | B1 | 10/2001 | Rice et al. |
| 6,537,225 | B1 | 3/2003 | Mills |
| 6,694,180 | B1 | 2/2004 | Boesen |
| 6,719,705 | B2 | 4/2004 | Mills |
| 6,819,950 | B2 | 11/2004 | Mills |
| 6,921,367 | B2 | 7/2005 | Mills |
| 6,985,763 | B2 | 1/2006 | Boas et al. |
| 7,154,592 | B2 | 12/2006 | Reynolds et al. |
| 7,167,736 | B2 | 1/2007 | Winther |
| 7,171,251 | B2 | 1/2007 | Sarussi et al. |
| 7,179,228 | B2 | 2/2007 | Banet |
| 7,209,775 | B2 | 4/2007 | Bae et al. |
| 7,291,497 | B2 | 11/2007 | Holmes et al. |
| 7,371,562 | B2 | 5/2008 | Cunningham et al. |
| 7,608,045 | B2 | 10/2009 | Mills |
| 7,647,083 | B2 | 1/2010 | Al-Ali et al. |
| 7,761,127 | B2 | 7/2010 | Al-Ali et al. |
| 7,763,472 | B2 | 7/2010 | Doctor et al. |
| 7,764,982 | B2 | 7/2010 | Dalke et al. |
| 7,941,199 | B2 | 5/2011 | Kiani |
| 8,224,411 | B2 | 7/2012 | Al-Ali et al. |
| 8,255,027 | B2 | 8/2012 | Al-Ali et al. |
| 8,328,420 | B2 | 12/2012 | Abreu |
| 8,385,996 | B2 | 2/2013 | Smith et al. |
| 8,401,605 | B2 | 3/2013 | Huiku |
| 8,483,787 | B2 | 7/2013 | Al-Ali et al. |
| 8,494,507 | B1 | 7/2013 | Tedesco et al. |
| 8,597,274 | B2 | 12/2013 | Sloan et al. |
| 8,652,040 | B2 | 2/2014 | Leboeuf et al. |
| 8,676,284 | B2 | 3/2014 | He |
| 8,730,047 | B2 | 5/2014 | Ridder et al. |
| 8,868,149 | B2 | 10/2014 | Eisen et al. |
| 8,888,701 | B2 | 11/2014 | Leboeuf et al. |
| 8,906,693 | B2 | 12/2014 | Schultz et al. |
| 8,923,918 | B2 | 12/2014 | Kreger et al. |
| 8,961,932 | B2 | 2/2015 | Silverman |
| 9,022,973 | B2 | 5/2015 | Sexton et al. |
| 9,131,882 | B2 | 9/2015 | Al-Ali et al. |
| 9,149,216 | B1 | 10/2015 | Eisen et al. |
| 9,149,646 | B2 | 10/2015 | Keswarpu et al. |
| 9,387,033 | B2 | 7/2016 | Yodfat et al. |
| 9,442,092 | B2 | 9/2016 | Lane |
| 9,521,970 | B2 | 12/2016 | Hoppe et al. |
| 9,554,738 | B1 | 1/2017 | Gulati et al. |
| 9,642,578 | B2 | 5/2017 | Newberry |
| 9,668,701 | B2 | 6/2017 | Maarek |
| 9,713,428 | B2 | 7/2017 | Chon et al. |
| 9,739,663 | B2 | 8/2017 | Halder et al. |
| 9,820,656 | B2 | 11/2017 | Olivier |
| 9,839,381 | B1 | 12/2017 | Weber et al. |
| 9,924,895 | B2 | 3/2018 | Rawicz et al. |
| 9,949,675 | B2 | 4/2018 | Miller |
| 9,999,355 | B2 | 6/2018 | Kirenko |
| 10,028,682 | B2 | 7/2018 | Thiele |
| D824,937 | S | 8/2018 | Sparandara et al. |
| 10,099,554 | B2 | 10/2018 | Steeg et al. |
| 10,130,285 | B1 | 11/2018 | Singamsetty et al. |
| 10,153,796 | B2 | 12/2018 | Fung et al. |
| 10,181,021 | B2 | 1/2019 | Venkatraman et al. |
| 10,206,619 | B1 | 2/2019 | Lee et al. |
| 10,215,698 | B2 | 2/2019 | Han et al. |
| 10,227,063 | B2 | 3/2019 | Abreu |
| 10,232,156 | B2 | 3/2019 | Netzel et al. |
| 10,278,591 | B2 | 5/2019 | Gil |
| D850,316 | S | 6/2019 | Ennis et al. |
| 10,314,500 | B2 | 6/2019 | Olivier |
| 10,322,728 | B1 | 6/2019 | Porikli et al. |
| 10,342,495 | B2 | 7/2019 | Melkoniemi et al. |
| 10,349,847 | B2 | 7/2019 | Kwon et al. |
| 10,420,470 | B2 | 9/2019 | Kwon et al. |
| 10,420,491 | B2 | 9/2019 | Rajan et al. |
| 10,433,726 | B2 | 10/2019 | Ramesh et al. |
| 10,433,738 | B2 | 10/2019 | Thomas et al. |
| 10,433,739 | B2 | 10/2019 | Weekly et al. |
| 10,463,283 | B2 | 11/2019 | Ferber et al. |
| 2002/0049389 | A1 | 4/2002 | Abreu |
| 2003/0229276 | A1 | 12/2003 | Sarussi et al. |
| 2004/0078219 | A1 | 4/2004 | Kaylor et al. |
| 2004/0100376 | A1 | 5/2004 | Lye et al. |
| 2004/0157341 | A1 | 8/2004 | Reynolds et al. |
| 2005/0101841 | A9 | 5/2005 | Kaylor et al. |
| 2005/0209516 | A1 | 9/2005 | Fraden |
| 2005/0228244 | A1 | 10/2005 | Banet |

(56) References Cited

U.S. PATENT DOCUMENTS

| | | |
|---|---|---|
| 2005/0228299 A1 | 10/2005 | Banet |
| 2005/0245831 A1 | 11/2005 | Banet |
| 2006/0009698 A1 | 1/2006 | Banet |
| 2006/0094942 A1 | 5/2006 | Winther |
| 2006/0287589 A1 | 12/2006 | Wobermin et al. |
| 2007/0202605 A1 | 8/2007 | Doctor et al. |
| 2007/0203405 A1 | 8/2007 | Shimomura |
| 2007/0260132 A1 | 11/2007 | Sterling |
| 2008/0146890 A1 | 6/2008 | Leboeuf et al. |
| 2008/0165017 A1 | 7/2008 | Schwartz |
| 2008/0208019 A1 | 8/2008 | Nitzan |
| 2008/0241199 A1 | 10/2008 | Silverman |
| 2009/0043178 A1 | 2/2009 | Belotserkovsky |
| 2009/0156988 A1 | 6/2009 | Ferren et al. |
| 2009/0187167 A1 | 7/2009 | Sexton et al. |
| 2009/0287120 A1 | 11/2009 | Ferren et al. |
| 2010/0049020 A1 | 2/2010 | Dalke et al. |
| 2010/0191080 A1 | 7/2010 | Mills |
| 2010/0274101 A1 | 10/2010 | Lin et al. |
| 2010/0295686 A1 | 11/2010 | Sloan et al. |
| 2010/0331631 A1 | 12/2010 | MacLaughlin |
| 2011/0082355 A1 | 4/2011 | Eisen et al. |
| 2011/0106050 A1 | 5/2011 | Yodfat et al. |
| 2011/0137141 A1 | 6/2011 | Razoumov et al. |
| 2011/0160697 A1 | 6/2011 | Yodfat et al. |
| 2011/0166553 A1 | 7/2011 | Holmes et al. |
| 2011/0224518 A1 | 9/2011 | Tindi et al. |
| 2011/0237464 A1 | 9/2011 | Cunningham et al. |
| 2011/0275978 A1 | 11/2011 | Hyde et al. |
| 2012/0010683 A1 | 1/2012 | Keswarpu et al. |
| 2012/0029363 A1 | 2/2012 | Lund |
| 2012/0095302 A1 | 4/2012 | Adhikari |
| 2012/0131507 A1 | 5/2012 | Sparandara et al. |
| 2012/0136054 A1 | 5/2012 | Schultz et al. |
| 2012/0156933 A1 | 6/2012 | Kreger et al. |
| 2012/0197093 A1 | 8/2012 | Lebouef et al. |
| 2012/0203077 A1 | 8/2012 | He et al. |
| 2012/0238844 A1 | 9/2012 | Grata et al. |
| 2012/0330126 A1 | 12/2012 | Hoppe et al. |
| 2013/0030259 A1 | 1/2013 | Thomsen et al. |
| 2013/0060098 A1 | 3/2013 | Thomsen et al. |
| 2013/0066176 A1 | 3/2013 | Addison et al. |
| 2013/0110311 A1 | 5/2013 | Ver Steeg et al. |
| 2013/0310669 A1 | 11/2013 | Nitzan |
| 2014/0046160 A1 | 2/2014 | Terashima et al. |
| 2014/0100432 A1 | 4/2014 | Golda et al. |
| 2014/0112940 A1 | 4/2014 | Lane |
| 2014/0194342 A1 | 7/2014 | Zhang et al. |
| 2014/0243648 A1 | 8/2014 | Dubielczyk |
| 2014/0253709 A1 | 9/2014 | Bresch et al. |
| 2014/0275852 A1 | 9/2014 | Hong et al. |
| 2014/0297313 A1 | 10/2014 | Condurso et al. |
| 2014/0316226 A1 | 10/2014 | Ferber et al. |
| 2015/0066238 A1 | 3/2015 | Todd et al. |
| 2015/0088007 A1 | 3/2015 | Bardy et al. |
| 2015/0094914 A1 | 4/2015 | Abreu |
| 2015/0105638 A1 | 4/2015 | Eisen et al. |
| 2015/0109617 A1 | 4/2015 | Gilbert et al. |
| 2015/0148622 A1 | 5/2015 | Moyer et al. |
| 2015/0148635 A1 | 5/2015 | Benaron |
| 2015/0150453 A1 | 6/2015 | Abreu |
| 2015/0182172 A1 | 7/2015 | Shelley et al. |
| 2015/0229341 A1 | 8/2015 | Fung et al. |
| 2015/0250404 A1 | 9/2015 | Maarek |
| 2015/0282747 A1 | 10/2015 | Thiele |
| 2015/0366471 A1 | 12/2015 | Leboeuf et al. |
| 2016/0018257 A1 | 1/2016 | Mirov et al. |
| 2016/0058308 A1 | 3/2016 | Robinson |
| 2016/0058347 A1 | 3/2016 | Reichgott et al. |
| 2016/0066863 A1 | 3/2016 | Thaveeprungsrporn et al. |
| 2016/0100781 A1 | 4/2016 | Bechtel et al. |
| 2016/0262707 A1 | 9/2016 | Devries |
| 2016/0345912 A1 | 12/2016 | Maarek |
| 2016/0367154 A1 | 12/2016 | Gladshtein et al. |
| 2017/0027521 A1 | 2/2017 | Geva et al. |
| 2017/0050518 A1 | 2/2017 | Steeg et al. |
| 2017/0071550 A1 | 3/2017 | Newberry |
| 2017/0091436 A1 | 3/2017 | Cao et al. |
| 2017/0172477 A1 | 6/2017 | Adusumilli et al. |
| 2017/0215811 A1 | 8/2017 | Newberry |
| 2017/0256110 A1 | 9/2017 | Divincent et al. |
| 2017/0347894 A1 | 12/2017 | Bhushan et al. |
| 2017/0347899 A1 | 12/2017 | Bhushan et al. |
| 2018/0117291 A1 | 5/2018 | Netzel et al. |
| 2018/0140210 A1 | 5/2018 | Jelfs et al. |
| 2018/0140237 A1 | 5/2018 | Rajan et al. |
| 2018/0177416 A1 | 6/2018 | Church et al. |
| 2018/0177440 A1 | 6/2018 | Jelfs et al. |
| 2018/0200433 A1 | 7/2018 | Cirit |
| 2018/0264242 A1 | 9/2018 | Hoffman et al. |
| 2018/0353137 A1 | 12/2018 | Balajadia et al. |
| 2018/0358119 A1 | 12/2018 | Bhushan et al. |
| 2019/0046039 A1 | 2/2019 | Ramesh et al. |
| 2019/0050622 A1 | 2/2019 | Cabibihan et al. |
| 2019/0086331 A1 | 3/2019 | Han |
| 2019/0099114 A1 | 4/2019 | Mouradian et al. |
| 2019/0110745 A1 | 4/2019 | Linnes et al. |
| 2019/0125963 A1 | 5/2019 | Mou et al. |
| 2019/0125964 A1 | 5/2019 | Mou et al. |
| 2019/0133471 A1 | 5/2019 | Olson et al. |
| 2019/0192085 A1 | 6/2019 | Krishna et al. |
| 2019/0192086 A1 | 6/2019 | Krishna et al. |
| 2019/0251238 A1 | 8/2019 | Venkatraman et al. |
| 2019/0358387 A1 | 11/2019 | Elbadry et al. |

FOREIGN PATENT DOCUMENTS

| | | |
|---|---|---|
| EP | 3488776 A1 | 5/2019 |
| WO | 2004047630 A1 | 6/2004 |
| WO | 2007013054 A1 | 2/2007 |
| WO | 2008006150 A1 | 1/2008 |
| WO | 2010128852 A3 | 11/2010 |
| WO | 2010147968 A1 | 12/2010 |
| WO | 2012108895 A1 | 8/2012 |
| WO | 2013052318 A1 | 4/2013 |
| WO | 2013127564 A1 | 9/2013 |
| WO | 2014163583 A1 | 10/2014 |
| WO | 2015143197 A1 | 9/2015 |
| WO | 2015200148 A1 | 12/2015 |
| WO | 2017001249 A1 | 1/2017 |
| WO | 2018025257 A1 | 2/2018 |
| WO | 2018206875 A1 | 11/2018 |
| WO | 2019030700 A1 | 2/2019 |
| WO | 2019118053 A1 | 6/2019 |

OTHER PUBLICATIONS

Noack et al. "Spectrophotometric determination of nitric oxide using hemoglobin." Neuroprotocols: A Companion to Methods in Neurosciences, vol. 1, No. 2,. pp. 133-139 (Oct. 1992).

Ignarro et al. "Endothelium-derived relaxing factor produced and released from artery and vein is nitric oxide." Proc. Natl. Acad. Sci. USA vol. 84, pp. 9265, 9269 (Dec. 1987).

SYSTEM AND METHOD FOR HEALTH MONITORING INCLUDING A USER DEVICE AND BIOSENSOR

CROSS REFERENCE TO RELATED APPLICATIONS

The present application claims priority under 35 U.S.C. § 120 as a continuation application to U.S. patent application Ser. No. 15/404,117 filed Jan. 11, 2017 entitled "SYSTEM AND METHOD FOR HEALTH MONITORING INCLUDING A USER DEVICE AND BIOSENSOR, and is hereby expressly incorporated by reference herein, which claims priority as a continuation in part application to the following:

U.S. patent application Ser. No. 15/400,916 entitled, "SYSTEM AND METHOD FOR HEALTH MONITORING INCLUDING A REMOTE DEVICE," filed Jan. 6, 2017, and issued as U.S. Pat. No. 10,750,981 issued Aug. 25, 2020 and hereby expressly incorporated by reference herein;

U.S. patent application Ser. No. 15/276,760 entitled, "SYSTEM AND METHOD FOR A DRUG DELIVERY AND BIOSENSOR PATCH," filed Sep. 26, 2016 and issued as U.S. Pat. No. 9,636,457 on May 2, 2017, and hereby expressly incorporated by reference herein;

U.S. patent application Ser. No. 15/275,444 entitled, "SYSTEM AND METHOD FOR A BIOSENSOR MONITORING AND TRACKING BAND," filed Sep. 25, 2016, and issued as U.S. Pat. No. 9,642,538 on May 9, 2017, and hereby expressly incorporated by reference herein;

U.S. patent application Ser. No. 15/275,388 entitled, "SYSTEM AND METHOD FOR HEALTH MONITORING USING A NON-INVASIVE, MULTI-BAND BIOSENSOR 500," filed Sep. 24, 2016 and issued as U.S. Pat. No. 9,642,578 on May 9, 2017, and hereby expressly incorporated by reference herein; and U.S. patent application Ser. No. 14/866,500 entitled, "SYSTEM AND METHOD FOR GLUCOSE MONITORING," filed Sep. 25, 2015 and issued as U.S. Pat. No. 10,321,860 on Jun. 18, 2019, and hereby expressly incorporated by reference herein.

The present application claims priority under 35 U.S.C. § 120 as a continuation in part application to U.S. patent application Ser. No. 15/718,721 entitled, "SYSTEM AND METHOD FOR MONITORING NITRIC OXIDE LEVELS USING A NON-INVASIVE, MULTI-BAND BIOSENSOR," filed Sep. 28, 2017 and issued as U.S. Pat. No. 10,517,515 on Dec. 31, 2019 and hereby expressly incorporated by reference herein, which claims priority as a continuation application to U.S. patent application Ser. No. 15/622,941 entitled, "SYSTEM AND METHOD FOR MONITORING NITRIC OXIDE LEVELS USING A NON-INVASIVE, MULTI-BAND BIOSENSOR," filed Jun. 14, 2017 and issued as U.S. Pat. No. 9,788,767 on Oct. 17, 2017, and hereby expressly incorporated by reference herein.

The present application claims priority under 35 U.S.C. § 120 as a continuation in part application to U.S. patent application Ser. No. 15/680,991 entitled, "SYSTEM AND METHOD FOR DETECTING A SEPSIS CONDITION," filed Aug. 18, 2017 and issued as U.S. Pat. No. 9,968,289 on May 15, 2018, and hereby expressly incorporated by reference herein.

The present application claims priority under 35 U.S.C. § 120 as a continuation in part application to U.S. patent application Ser. No. 15/462,700 entitled, "SYSTEM AND METHOD FOR ATOMIZING AND MONITORING A DRUG CARTRIDGE DURING INHALATION TREATMENTS," filed Mar. 17, 2017 and issued as U.S. Pat. No. 10,500,354 on Dec. 10, 2019 and hereby expressly incorporated by reference herein, which claims priority under 35 U.S.C. § 119(e) to U.S. Provisional Application No. 62/457,138 entitled, "SYSTEM AND METHOD FOR ATOMIZING AND MONITORING A DRUG CARTRIDGE DURING INHALATION TREATMENTS," filed Feb. 9, 2017 and hereby expressly incorporated by reference herein.

FIELD

This application relates to systems and methods of non-invasive, autonomous health monitoring and drug administration using a biosensor and user device.

BACKGROUND

Various techniques are available for obtaining biosensor measurements, such as blood glucose levels in patients with diabetes. One technique requires a small blood sample from the patients, e.g. from a finger prick. The blood sample is placed on a chemically prepared test strip and inserted into a glucose meter that analyzes the test strip and provides a blood glucose level. Unfortunately, to monitor their blood glucose levels, diabetics may need to prick their fingers multiple times within a day. This monitoring process can be painful, inconvenient and creates possible exposure to infections. Additionally, measurements with these devices present an error of uncertainty range between approximately 10-20% depending on sample quality, human error, calibration, humidity, and hygiene in the sample area. Thus, there is a need for an accurate, non-invasive blood analytic and glucose monitoring and tracking system and method and device that eliminates the pain of drawing blood as well as eliminates a source of potential infection.

In addition, there is a need for accurate and non-invasive biosensor measurements, such as pulse, blood oxygen level, electrolyte levels, etc. It is important to provide a convenient system for monitoring and tracking these biosensor measurements.

In addition, there is a need for a more accurate and non-invasive drug administration device based on biosensor monitoring and feedback.

SUMMARY

According to a first aspect, user equipment includes a display and at least one transceiver configured to communicate with an external biosensor, wherein the at least one transceiver receives biosensor data from the biosensor. The user equipment further includes at least one processing circuit and at least one memory device, wherein the at least one memory device stores instructions which when executed by the at least one processing device, causes the user equipment to process the biosensor data to determine a level of nitric oxide (NO) in blood flow, wherein the biosensor data includes a first PPG signal at a first wavelength and a second PPG signal at a second wavelength and generate a graphical user interface (GUI) that displays the biosensor data on the display of the user equipment.

According to a second aspect, user equipment includes a display and at least one transceiver configured to communicate over a cellular network and to an external biosensor. The user equipment further includes at least one processing circuit and at least one memory device, wherein the at least one memory device stores instructions which when executed by the at least one processing device, causes the user equipment to obtain a value $L_{\lambda 1}$ using an AC component of a first PPG signal; obtain a value $L_{\lambda 2}$ using an AC component of a second PPG signal; obtain a value $R_{\lambda 1, \lambda 2}$ from a ratio including the value $L_{\lambda 1}$ and the value $L_{\lambda 2}$; obtain a blood glucose level using the value $R_{\lambda 1, \lambda 2}$; and generate a graphical user interface that includes the blood glucose level on the display.

According to a third aspect, user equipment includes one or more transceivers configured to communicate over a cellular network and to at least one external biosensor. The user equipment also includes at least one processing circuit and at least one memory device, wherein the at least one memory device stores instructions which when executed by the at least one processing device, causes the user equipment to obtain a first AC component of a first PPG signal around a first wavelength of light ($\lambda 1$), wherein the first wavelength of light is in a range of 370 nm to 410 nm; obtain a second AC component of a second PPG signal around a second wavelength of light ($\lambda 1$), wherein the second wavelength of light is in an infrared (IR) range; and obtain an R value from a ratio including the first AC component and the second AC component.

In one or more of the above aspects, the user equipment is further configured to generate a GUI that displays one or more commands for controlling the biosensor; receive user input indicating a command for the biosensor; and transmit a command to the biosensor in response to the user input.

In one or more of the above aspects, the first wavelength of light has a high absorption coefficient for nitric oxide (NO) levels in blood flow and the second wavelength of light has a low absorption coefficient for NO levels in blood flow.

In one or more of the above aspects, the user equipment is configured to obtain a value $L_{\lambda 1}$ using a first PPG signal; obtain a value $L_{\lambda 2}$ using the second PPG signal; and determine a value $R_{\lambda 1, \lambda 2}$ using a ratio including the value $L_{\lambda 1}$ and the value $L_{\lambda 2}$. The user equipment is configured to determine a level of nitric oxide (NO) in blood flow using at least the value $R_{\lambda 1, \lambda 2}$.

In one or more of the above aspects, the user equipment is configured to obtain a blood glucose concentration level using at least the value $R_{\lambda 1, \lambda 2}$ and a calibration.

In one or more of the above aspects, the user equipment is configured to determine a level of vasodilation using the biosensor data, wherein the level of vasodilation includes a measurement of a localized change in width of a vessel from a localized relaxation of vascular muscle cells within the vessel walls.

In one or more of the above aspects, the biosensor is implemented in a finger attachment and the user equipment includes a smart phone.

In one or more of the above aspects, the user equipment is configured to generate a command to a drug administrative device to administer medication.

In one or more of the above aspects, the user equipment is configured to generate a message with the blood glucose level to a third party health care provider and transmit the message over a wide area network to the third party health care provider.

DETAILED DESCRIPTION

The word "exemplary" or "embodiment" is used herein to mean "serving as an example, instance, or illustration." Any implementation or aspect described herein as "exemplary" or as an "embodiment" is not necessarily to be construed as preferred or advantageous over other aspects of the disclosure. Likewise, the term "aspects" does not require that all aspects of the disclosure include the discussed feature, advantage, or mode of operation.

Embodiments will now be described in detail with reference to the accompanying drawings. In the following description, numerous specific details are set forth in order to provide a thorough understanding of the aspects described herein. It will be apparent, however, to one skilled in the art, that these and other aspects may be practiced without some or all of these specific details. In addition, well known steps in a method of a process may be omitted from flow diagrams presented herein in order not to obscure the aspects of the disclosure. Similarly, well known components in a device may be omitted from figures and descriptions thereof presented herein in order not to obscure the aspects of the disclosure.

Overview

User equipment (UE) includes a smart phone, tablet, watch, laptop, or other type of portable user device. The UE is configured to collect biosensor data from one or more integrated biosensors or by receiving biosensor data from one or more external biosensors through a wireless or a wired connection. The UE includes a Health Monitoring (HM) application. The HM application is configured to receive the biosensor data and display the biosensor data on the display of the UE. The UE may also communicate biosensor data over a local or wide area network to a third party, such as a pharmacy or physician's office.

In an embodiment, the integrated or external biosensors may include a pulse oximeter configured to detect pulse and blood oxygen levels. The integrated or external biosensors may also include a temperature sensor to detect body temperature. In an embodiment, at least one of the integrated or external biosensors includes a PPG circuit configured to detect one or more substances in blood, such as an indicator of glucose levels in arterial blood flow or blood levels of other substances, such as bilirubin, sodium, potassium, or even blood alcohol levels.

Embodiment—User Equipment for Health Monitoring

Figure 1:
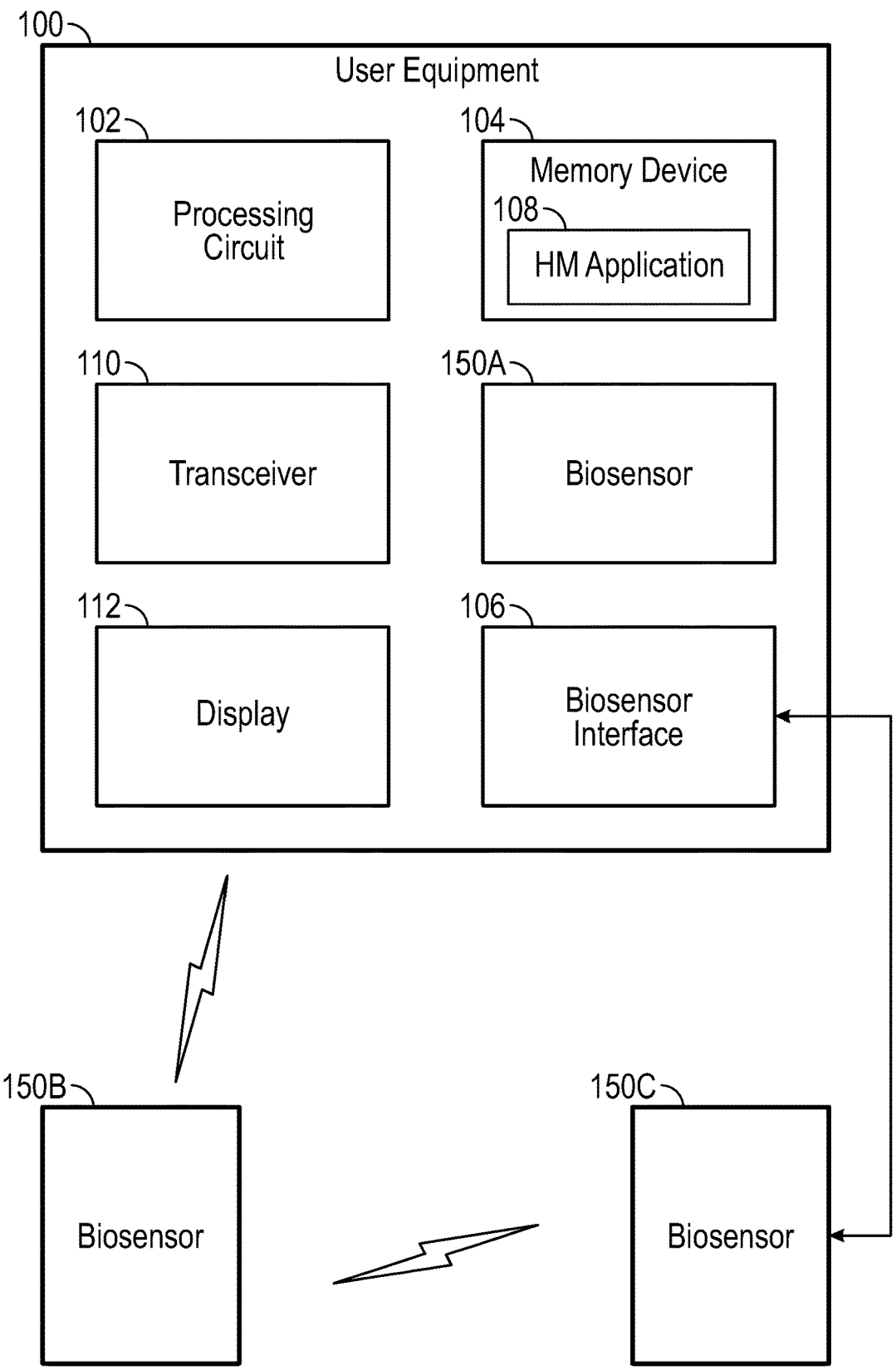
FIG. 1 illustrates an exemplary embodiment of user equipment (UE) for health monitoring.

FIG. 1 illustrates an exemplary embodiment of user equipment (UE) 100 for health monitoring. The UE 100 may include a smart phone, tablet, watch, laptop, or other type of portable user device. The UE 100 includes a processing circuit 102 and a memory device 104 that stores instructions that when performed by the processing circuit 102 may perform one or more of the functions described herein with respect to the UE 100. The UE 100 includes a biosensor interface 106 that is configured to collect biosensor data from an integrated biosensor 150A and/or by receiving biosensor data from one or more external biosensors 150B, 150C through a wireless or a wired connection.

The UE 100 may also include a wireless and/or wired transceiver 110 and display 112. In one aspect, the UE 100 further includes a Health Monitoring (HM) application 108 stored in the memory device 104. The processing circuit 102 is configured to process one or more instructions of the HM application 108 to perform one or more of the functions described herein. The HM application 108 processes biosensor data and displays the biosensor data on the display 112. The HM application 108 may also generate messages for transmission to third parties by the transceiver 110.

For example, the HM application 108 may generate messages that include requests to refill medications that are transmitted to a pharmacy over a wide area network (WAN) using the transceiver 110. In another example, the HM application 108 may generate messages that include patient health data that are transmitted to a doctor's hospital.

Figure 2:
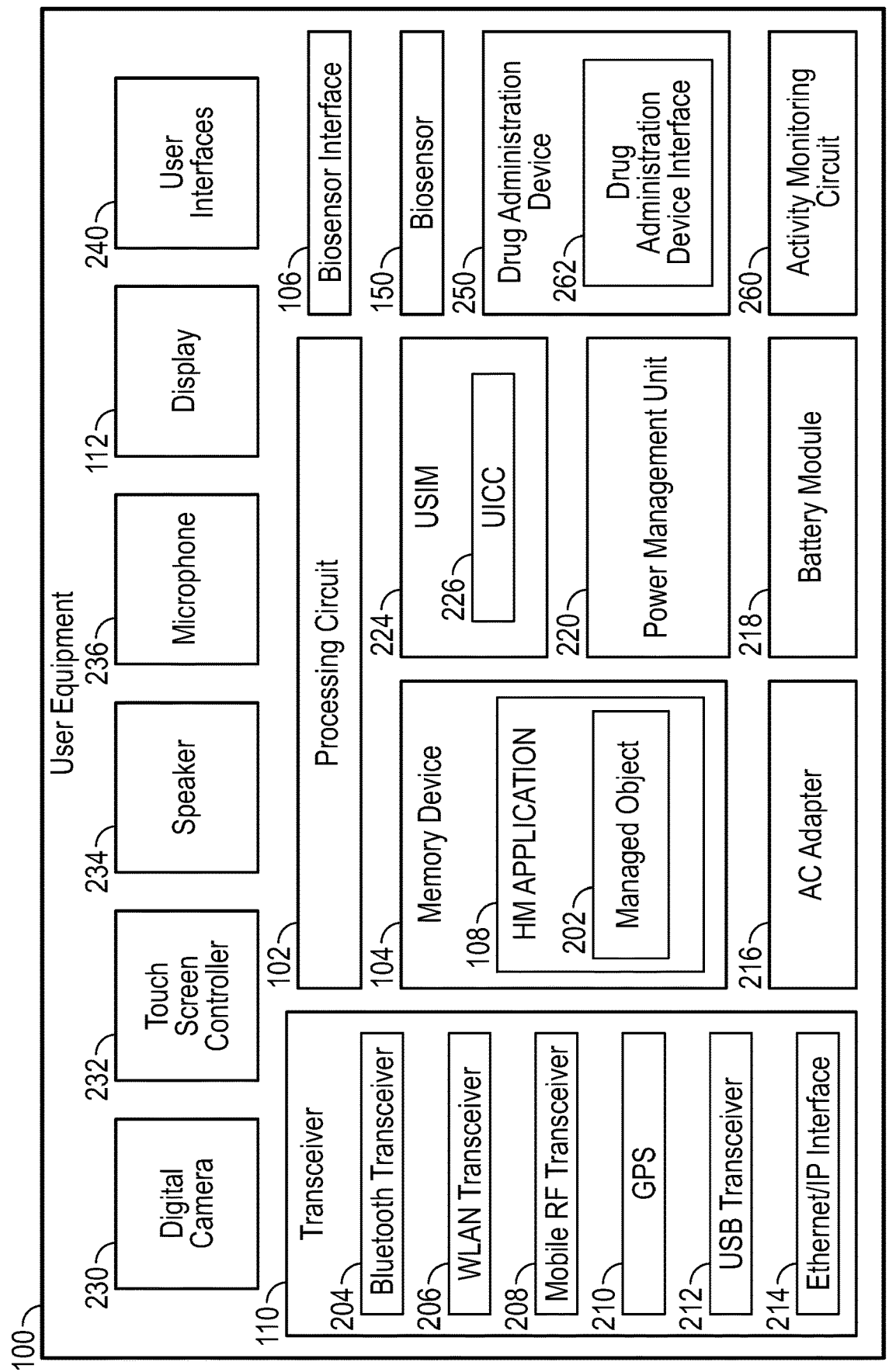
FIG. 2 illustrates a schematic block diagram of an embodiment of the user equipment in more detail.

FIG. 2 illustrates a schematic block diagram of an embodiment of the user equipment 100 in more detail. The components of the UE 100 described herein are exemplary and additional or alternative components and functions may be implemented. In addition, one or more of the functions or components shown herein may not be present or may be combined with other components or functions. The UE 100 includes the display 112, the processing circuit 102 and the memory device 104. The memory device 104 may include a managed object 202 that stores the HM application 108 for instructing the UE 100 to perform one or more of the functions described herein.

The UE 100 further includes a transceiver 110. The transceiver 110 may include one or more of a Bluetooth transceiver 204, a WLAN (IEEE 802.11x compliant) transceiver 206, and a global positioning satellite (GPS) transceiver 210. The WLAN transceiver 206 may operate as a non-3GPP access interface to a WLAN network, e.g. compliant with one or more standards under IEEE 802.11 protocols. The UE 100 also includes a mobile radio frequency (RF) transceiver 208 configured to communicate over a cellular network. For example, the mobile RF transceiver 208 may communicate voice calls over cellular networks that are, e.g., compliant with Universal Mobile Telecommunications System (UMTS) Terrestrial Radio Access Network (UTRAN), Long Term Evolution (LTE) Evolved UTRAN (E-UTRAN), LTE-Advanced (LTE-A) and/or other wireless cellular network. The UE 100 may also include one or more wireline transceivers, such as a universal serial bus (USB) transceiver 212 or Ethernet/IP transceiver 214. In other embodiments, the transceiver 110 may operate in one or more other wireless frequency bands or protocols, such as near field communication, short range radio frequency, RFID, or other wireless communication protocol.

The UE 100 may further include an AC adapter 216, battery module 218 and a power management unit 220. The power management unit 220 helps to control power functions of the UE 100. When the UE 100 includes a cellular phone, the UE 100 may include a Universal Subscriber Identity Module (USIM) application 224 on an a smart card such as a Universal Integrated Circuit Card (UICC) 226. The UE 100 may further include one or more user devices, such a digital camera 230, touch screen controller 232, speaker 234 and microphone 236. The UE 100 may include one or more additional user interfaces 240, such as a keypad, touch screen, touch pad, etc. For example, the UE 100 may include a mouse and use an IR or visible light to move a pointer or other icon on the display 112 to select commands to control one or more biosensors and/or and the HM application 108. The user interface 240 may include a touch pad to select commands on the display 112 that controls operation of the UE 100 and/or HM application 108. In another embodiment, the UE 100 includes a touch screen that displays graphical user interfaces having selections and commands for controlling the UE 100 or HM application 108. One or more internal communication buses (not shown) communicatively couple the components of the UE 100.

In an embodiment, the UE 100 is configured to collect biosensor data, e.g. either by receiving biosensor data from external biosensors 150 through the biosensor interface 106 or from one or more integrated biosensors 150. For example, the biosensor 150 may include one or more sensors, such as a temperature sensor (contact or non-contact), a pulse oximeter circuit, a blood pressure circuit, or a PPG circuit, as described in more detail herein. In addition, the UE 100 may communicate with external biosensors 150 using the transceiver 110 to receive biosensor data.

The UE 100 may also include an activity monitoring circuit 260. In another embodiment, the UE 100 communicates with an external activity monitoring device, such as a FitBit® wireless wristband or other external activity tracker. The HM application 108 may collect activity information, such as periods of rest, periods of activity, steps walked or run, etc. The HM application 108 may then instruct the UE 100 to display a graphical user interface (GUI) illustrating the activity information for one or more users.

The UE 100 may also include an integrated Drug Administration Device 250 and/or a Drug Administration Device Interface 262 that is configured to deliver medication to a patient in response to the biosensor data. For example, the Drug Administration Device 250 may include an external or integrated skin patch, IV drug pump, etc.

In an embodiment, the health monitoring (HM) application 108 processes the biosensor data, such as measurements made by the biosensors, and generates health monitoring data. For example, the HM application may instruct the processing circuit 102 to execute logic to process biosensor data to determine blood pressure, pulse rate, blood oxygen saturation levels (SpO$_2$), electrocardiogram (EKG or ECG), etc. The HM application may generate one or more graphical user interfaces (GUI). The GUIs present the biosensor data received or processed by the UE 100 as well as user commands to control the biosensors. The UE 100 may also communicate biosensor data with other user equipment.

Figure 3:
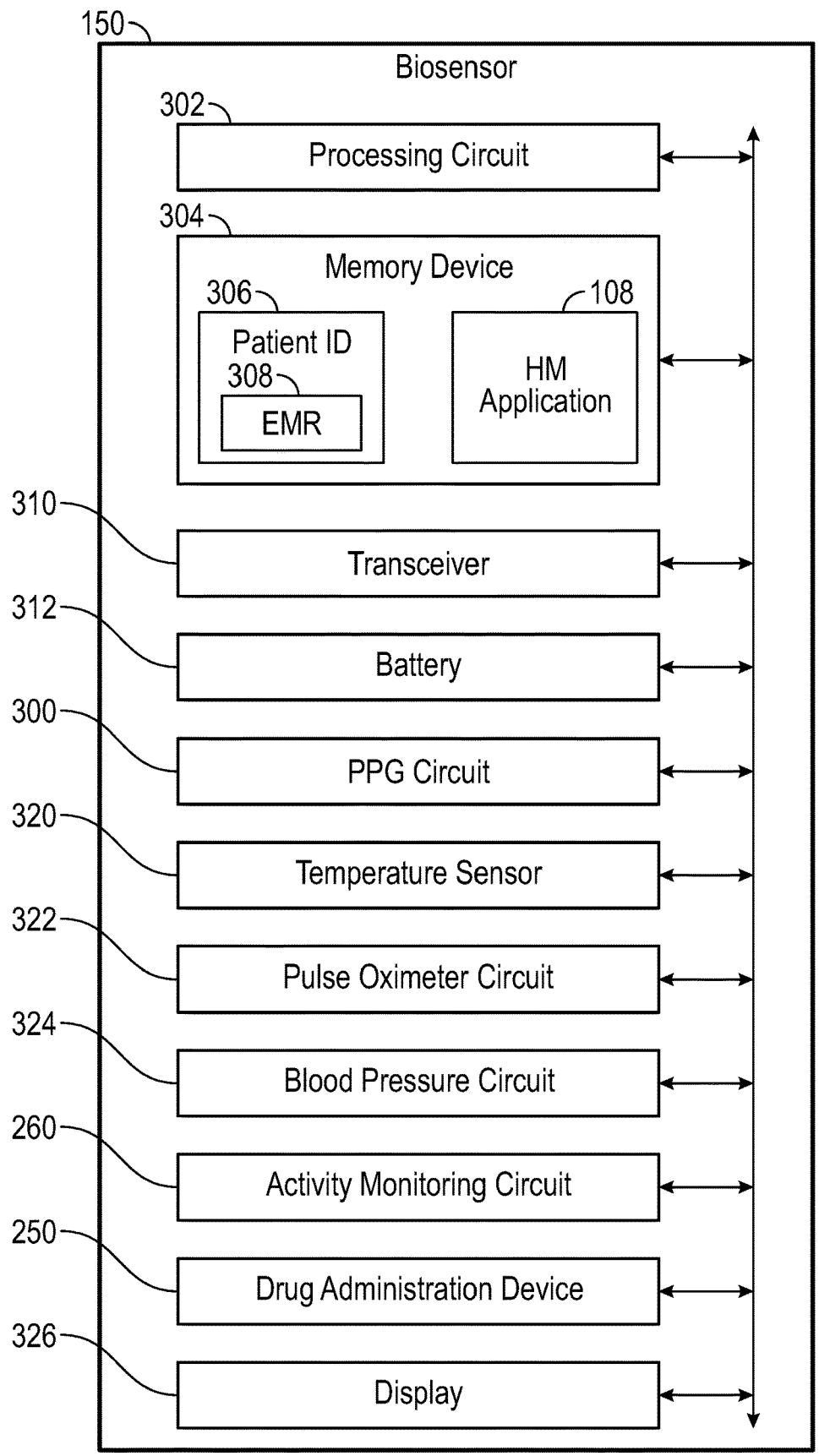
FIG. 3 illustrates a schematic block diagram of an exemplary embodiment of a biosensor.

FIG. 3 illustrates a schematic block diagram of an exemplary embodiment of a biosensor 150. The biosensor 150 may be integrated with the UE 100 or may be external to the UE 100 and wirelessly communicate with the UE 100. When located externally, the biosensor 150 may include a separate processing circuit 302, memory device 304, transceiver 310 and battery 312. When integrated with the UE 100, the biosensor 150 may include one or more of these separate components or utilize the processing circuit 102, memory device 104, battery module 218, transceiver 110 or other components of the UE 100.

The processing circuit 302 is communicatively coupled to the memory device 304. In one aspect, the memory device 304 may include one or more non-transitory processor readable memories that store instructions which when executed by the processing circuit 302, causes the processing circuit 302 to perform one or more functions described herein. The memory device 304 may also include an EEPROM to store one or more patient identifications (ID) 306, wherein each of the patient IDs 306 are associated with a user being monitored by the biosensor 150. The memory device 304 may also store an electronic medical record (EMR) 308 or portion of an EMR 308 associated with each of the patient IDs 306. The biosensor 150 may thus be used to monitor multiple users or patients associated with different patient IDs 306. The biosensor data obtained by the biosensor 150 may be stored in the EMR 308 associated with the patient ID 306 of the monitored user. The processing circuit 302 may be co-located with one or more of the other circuits in the biosensor 150 in a same physical encasement or located separately in a different physical encasement or located remotely.

The biosensor 150 may further include a transceiver 310, for example, when the biosensor 150 is external to the UE 100. The transceiver 710 may transmit the patient ID 306 and associated biosensor data to the UE 100. The transceiver 310 may include a wireless or wired transceiver configured to communicate with the UE 100 over a USB port or short range wireless interface or over a LAN, MAN and/or WAN. In one aspect, the transceiver 310 may include IEEE 802.11ah, Zigbee, IEEE 802.15-11 or WLAN (such as an IEEE 802.11 standard protocol) compliant transceiver, RFID, short range radio frequency, Bluetooth, infrared link, or other wireless communication protocol. In another aspect, the transceiver 310 may also include or alternatively include an interface for communicating over a cellular network. In an embodiment, the transceiver 310 may include a thin foil for an antenna that is specially cut and includes a carbon pad contact to a main PCB of the biosensor 150. This type of antenna is inexpensive to manufacture and may be printed on the inside of an enclosure for the biosensor 150 situated away from the skin of the patient to minimize absorption. The transceiver 310 may also include a wired transceiver interface, e.g., a USB port or other type of wired connection, for communication with the UE 100 or one or more other devices over a LAN, MAN and/or WAN. In an embodiment, the biosensor 150 is battery operated and includes a battery 312, such as a lithium ion battery.

The biosensor 150 includes one or more types of sensors, such as photoplethysmography (PPG) circuit 300, a temperature sensor 320, pulse oximeter circuit 322 or blood pressure circuit 324. The temperature sensor 320 is configured to detect a temperature of a patient. For example, the temperature sensor 320 may include an array of sensors (e.g., 16×16 pixels) positioned on a side of the biosensor 150. The array of sensors then detects an indication of the temperature of the patient from the skin. In another embodiment, the biosensor 150 may include a thermopile infrared (IR) temperature sensor. In use, a user swipes the biosensor 150 over their forehead or other area of the body. The biosensor 150 detects the temperature and transmits the temperature to the HM application 108 for storage and tracking. The HM application 108 may instruct the UE 100 to display a graphical user interface (GUI) illustrating a current temperature and a history of temperature readings for the user.

The pulse oximeter circuit 322 detects pulse or heart rate and blood oxygen saturation levels ($SpO_2$) and transmits the biosensor data to the HM application 108 for storage and tracking. The HM application 108 may instruct the UE 100 to display a graphical user interface (GUI) illustrating a current pulse and blood oxygen level and a history of heart rate and blood oxygen levels for one or more users. In addition, the pulse oximeter circuit 322 may be configured to monitor blood flow. For example, the biosensor 150 monitors and transmits heart rate measurements from one or more extremities, such as the arms and legs of the user, as well as from a chest/heart area of the user. The user may move the biosensor 150 to the plurality of positions or multiple biosensors 150 may be used. The heart rate readings from the heart/chest area and from the one or more extremities of the user are monitored and tracked by the HM application 108 of the UE 100. The heart rate readings are used to determine and track blood flow between the heart and the one or more extremities. Based on the heart rate readings, the HM application 108 may determine potential blockages in blood flow.

The blood pressure sensor 324 detects blood pressure and transmits the blood pressure to the HM application 108 for storage and tracking. The HM application 108 may instruct the UE 100 to display a graphical user interface (GUI) illustrating a current blood pressure and a history of blood pressure readings for one or more users.

In an embodiment, the UE 100 may include a photoplethysmography (PPG) circuit 300. The PPG circuit 300 is configured to generate at least a first spectral response for light reflected around a first wavelength from skin tissue of the patient, generate at least a second spectral response for light detected around a second wavelength reflected from the skin tissue of the patient. The processing circuit 302 is configured to process the first and second spectral responses at the first wavelength and the second wavelength and determine biosensor data using the first and second spectral responses. For example, the biosensor data may include oxygen saturation levels and pulse rate. The PPG circuit 300 may thus be included as the pulse oximeter circuit 322 or in addition to a separate pulse oximeter circuit 322. In addition, the PPG circuit 300 may also obtain concentration levels of one or more substances in arterial blood flow using first and second spectral responses at predetermined wavelengths. For example, the PPG circuit 300 may determine an indicator of glucose levels, analyte levels, blood alcohol levels, etc. The operation of the PPG circuit 300 is described in more detail herein.

The activity monitoring circuit 260 is configured to monitor the activity level of a user or patient of the biosensor 150. For example, the activity monitoring circuit 260 may include a multiple axes accelerometer that measures a position of the patient and motion of the patient. In one aspect, the activity monitoring circuit 260 determines periods of activity and rest. For example, the activity monitoring circuit 260 monitors and records periods of rest that meet a predetermined threshold of low motion or activity level, such as sitting, lying, sleeping, etc. The activity monitoring circuit 260 may also monitor and record periods of activity that meet a predetermined threshold of motion or activity level, such as walking, running, lifting, squatting, etc. The biosensor 150 is then configured to measure and store biosensor data, such as the patient vitals, with an indicator of the activity level of the patient. For example, blood oxygen levels may vary greatly in patients with COPD during rest and activity. Biosensor data, such as the vitals of the patient, are tracked during periods of activity and rest and the level of activity at time of measuring the vitals is recorded. The biosensor 150 is thus configured to associate measurements of patient vitals, such as pulse rate, blood oxygen levels, temperature, etc., with the activity level of the patient. The biosensor 150 may also track levels of substances in the blood using the PPG circuit 300 and the associated level of activity of the patient. For example, the biosensor 150 may track an indicator of glucose levels in the blood and the activity level of a user over a day, week, month, etc.

In another aspect, to help lower power consumption, in an embodiment, the biosensor 150 includes a rest mode. For example, the activity monitoring circuit 260 may signal a rest mode when a patient is asleep or meets a predetermined threshold of low activity level for a predetermined time period. In the rest mode, the biosensor 150 signals one or more modules to halt non-essential processing functions. When the activity monitoring circuit 260 detects a higher activity level exceeding another predetermined threshold for a predetermined time period, the biosensor 150 signals one or more modules to exit rest mode and resume normal functions. This activity monitoring feature helps to save power and extend battery life of the biosensor 150.

In another aspect, the activity monitoring circuit 260 is configured to include a fitness tracker application. The activity monitoring circuit 260 may monitor a number of steps of the patient, amount and length of periods of sleep, amount and length of periods of rest, amount and length of periods of activity, etc.

The biosensor 150 may also include an integrated drug administration device 250 or be communicatively coupled to a drug administration device 250. The biosensor 150 may be configured to control delivery of medication to a patient based on biosensor data obtained by the biosensor 150 as described in more detail in U.S. patent application Ser. No. 15/276,760 entitled, "SYSTEM AND METHOD FOR A DRUG DELIVERY AND BIOSENSOR PATCH," filed Sep. 26, 2016 and hereby expressly incorporated by reference herein.

The biosensor 150 may include a display 326. The HM application 108 is configured to display a graphical user interface (GUI) on the display 326 that includes biosensor data and controls for the biosensor 150.

Embodiment—Drug Administrative Device

Figure 4:
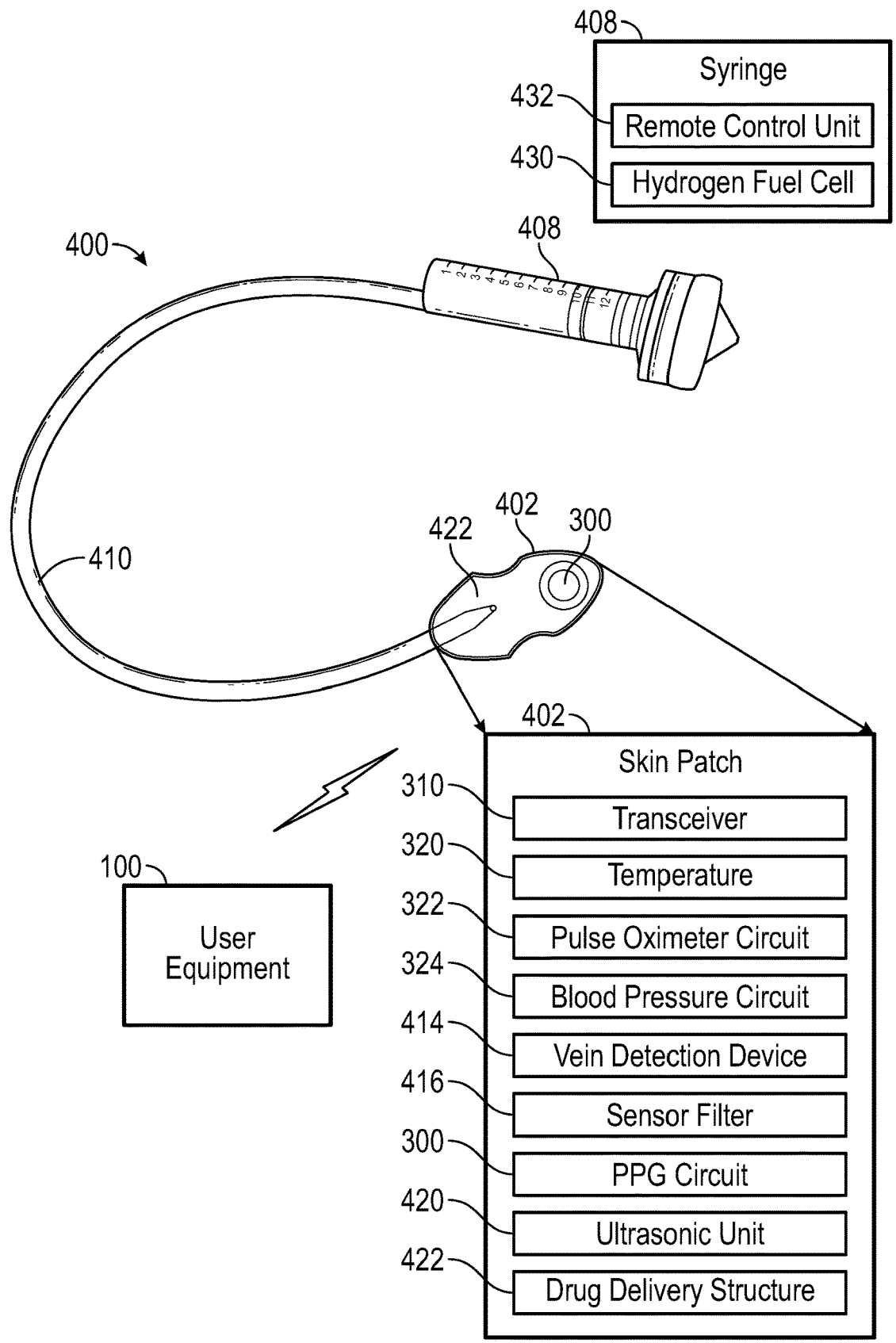
FIG. 4 illustrates an exemplary embodiment of a drug administrative device.

FIG. 4 illustrates an exemplary embodiment of a drug administrative device 400. The drug administrative device 400 includes a skin patch 402 and drug pump or syringe 408. The skin patch 402 includes a wired or wireless transceiver 310 configured to communicate with the UE 100. Though the wireless transceiver 310 is illustrated as integrated within the skin patch 402, it may be included in one or more other parts of the drug administrative device 400. A battery, such as a hydrogen fuel cell, may be integrated to power the wireless transceiver 310 and other components of the drug administrative device 250.

The skin patch 402 may also include one or more biosensors, e.g., a PPG circuit 300 as well as a temperature sensor 320, pulse oximeter circuit 322 or blood pressure circuit 324. The pulse oximeter circuit 322 is configured to detect a heart rate of a patient during drug delivery.

The skin patch 402 may also include a vein detection device 414 that assists a user, such as a patient or care giver, to locate veins or arteries. The vein detection device 414 is configured to scan a designated area of skin using an infrared (IR) signal to locate a high IR signature that indicates the presence of a vein or an artery. Alternatively or additionally, an ultraviolet (UV) signal may be used as well to detect the location of vein or artery. The vein detection device 414 may include a sensor filter 416 that filters out ambient light and light not reflected from the skin but passes IR light reflected from the designated area of the skin.

The PPG circuit 300 is configured to obtain at least a first spectral response for light reflected around a first wavelength from skin tissue of the patient, obtain at least a second spectral response for light detected around a second wavelength reflected from the skin tissue of the patient. A processing circuit (not shown) within the skin patch 402 or PPG circuit 300 is configured to process the first and second spectral responses at the first wavelength and the second wavelength and determine patient vitals using the first and second spectral responses. For example, the PPG sensor may be configured to detect oxygen saturation ($SpO_2$) levels in blood flow, as well as heart rate and blood pressure.

The PPG circuit 300 may thus be included as the pulse oximeter circuit 322 or blood pressure circuit 324 or in addition to a separate pulse oximeter circuit 322 or blood pressure circuit 324. In addition, the PPG circuit 300 may also obtain concentration levels of one or more substances in arterial blood flow using first and second spectral responses at predetermined wavelengths, such as an indicator of glucose levels, analyte levels, blood alcohol levels, etc. The operation of the PPG circuit 300 is described in more detail herein.

The skin biosensor 150 may include additional or alternative components, such as an activity monitoring circuit 260, display 326, etc.

In an embodiment, the skin patch 402 is configured to administer medication to a user through the drug delivery structure 422. The drug delivery structure 422 may include permeable material or an array of microneedles. The drug delivery structure 422 may also include a drug fluid bowl that holds a predetermined dosage of the medication.

The skin patch 402 may also include an ultrasonic unit 420 that includes an ultrasonic transducer and one or more ultrasonic horns (also known as acoustic horn, sonotrode, acoustic waveguide, and ultrasonic probe) embedded in the skin patch. The ultrasonic horn is a tapering metal bar commonly used for augmenting the oscillation displacement amplitude provided by the ultrasonic transducer. The skin patch 402 then initiates transdermal application of medication through a permeable material or microneedles while ultra-sonically transmitting energy into the epidermal layer of the skin using the ultrasonic unit 420. This process excites pours on the sub-cutaneous layer of the skin to allow rapid absorption of the medication.

The drug delivery structure 422 may be coupled to a syringe 408 by IV tubing 410. For example, the syringe 408 may be preloaded with the medication for administration by the skin patch 402. The UE 100 or skin patch 402 is then configured to control the syringe to secrete a predetermined dosage of medication at a predetermined rate of administration. The UE 100 or skin patch 402 may also control the predetermined dosage of medication, the predetermined rate of administration and period of time between dosages based on the biosensor data from the skin patch 402 or other biosensors 150. For example, the UE 100 receives real time, continuous feedback of biosensor data from one or more biosensors 150 during periods of administration of the medication. If the UE 100 detects an allergic reaction or unsafe heart rate based on the biosensor data, the UE 100 may control the syringe 408 and/or skin patch 402 to halt secretion of the medication.

In another embodiment, the UE 100 may be implemented to control a Smart Injectable Pen, a Continuous Glucose Monitoring Device and Insulin Pump, or other drug administering device. For example, the UE 100 may control an IV infusion pump using biosensor data received from one or more biosensors 150, such as the skin patch 402.

The syringe 408 may be powered by a battery, such as a hydrogen fuel cell 430. The hydrogen fuel cell 430 powers the syringe 408 to push the pre-loaded medications in the syringe 408 to the skin patch 402. The syringe 408 may include a remote control unit 432 including a processing circuit that controls the syringe 408 to dispense a predetermined dosage of medication at a predetermined rate of administration. In another embodiment, the remote control unit 432 may be configured to provide for direct injection of medication into an IV tube or catheter or a smart pen or custom IV syringe. The UE 100 communicates with the remote control unit 432 to control the dosage and administration rate of the medication using continuous and real time feedback of biosensor data, such as heart rate.

Figure 5A:
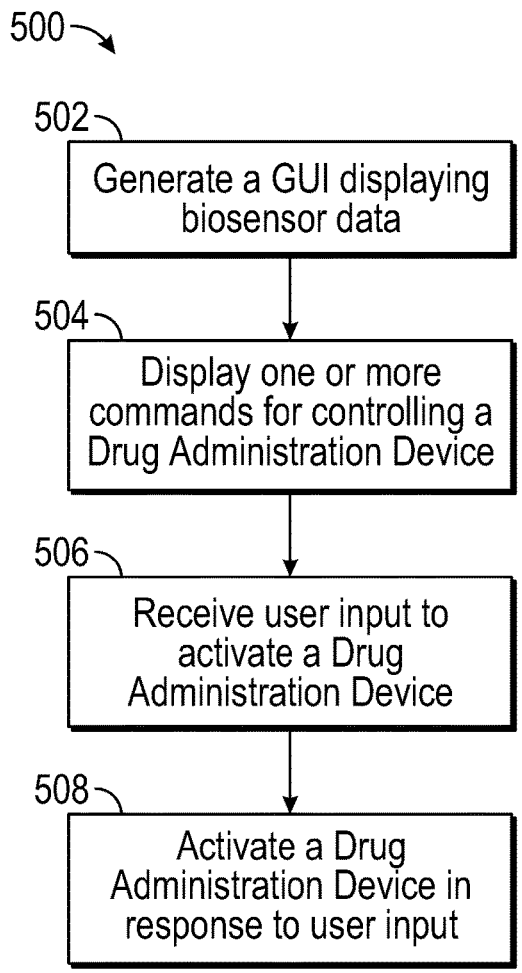
FIG. 5A illustrates a logical flow diagram of an embodiment of a method for administration of medication using the UE.

FIG. 5A illustrates a logical flow diagram of an embodiment of a method 500 for administration of medication using the UE 100. The HM application 108 generates a GUI that includes biosensor data from one or more integrated or external biosensors 150 at 502 and displays the GUI on the UE 100. The HM application 108 may also generate and display a GUI including one or more commands for controlling a drug administration device 250 at 504. The UE 100 receives user input to activate the drug administration device 250 at 506. The user input may specify or select a type of medication, a predetermined dosage of medication, a time of administration or rate of administration of the medication. Based on the user input, the HM application 108 activates the drug administration device at 508.

Figure 5B:
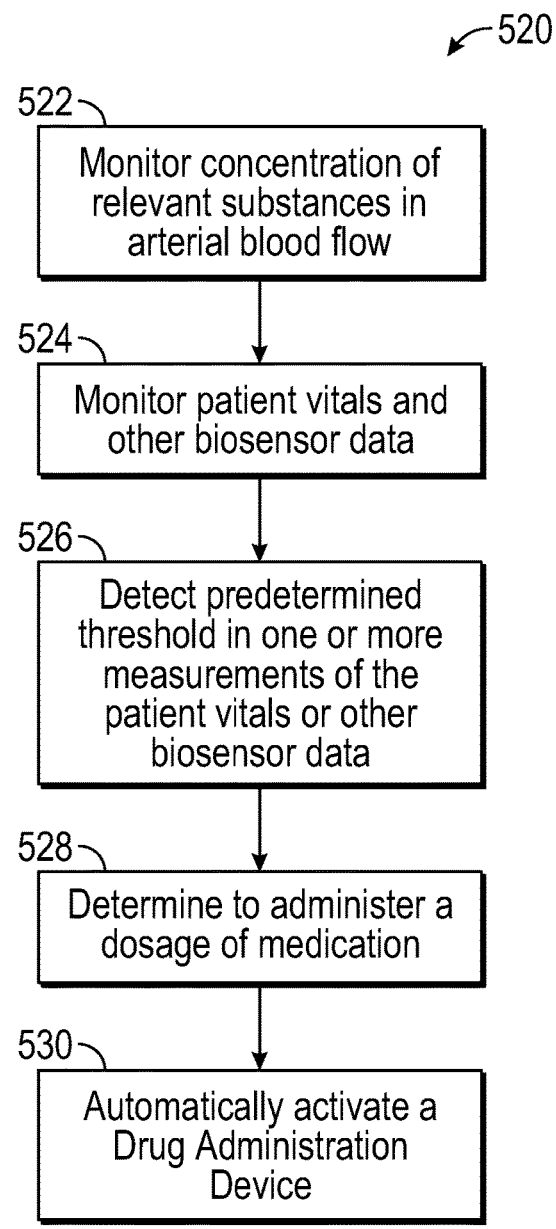
FIG. 5B illustrates a logical flow diagram of an embodiment of another method for administration of medication using the UE.

FIG. 5B illustrates a logical flow diagram of an embodiment of a method 520 for administration of medication using the UE 100. The HM application 108 in the UE 100 may non-invasively and continuously monitor a concentration of relevant substances in arterial blood flow using one or more integrated or external biosensors 522. For example, the PPG circuit 300 using PPG techniques described herein, detects a spectral response of reflected light at one or more wavelengths. Based on the spectral response, concentration levels of one or more relevant substances in surrounding tissues and/or arterial blood flow may be determined. For example, an indicator of insulin levels after caloric intake in arterial blood flow may be determined and monitored or a level of white blood cells may be monitored in the arterial blood flow by the PPG circuit 300.

The UE 100 may also monitor patient vitals, such as respiratory rate, temperature, heart rate, blood pressure, blood oxygen $SpO_2$ levels, ECG, etc., using one or more integrated or external biosensors 150. The UE 100 may also monitor other biosensor data, such as activity level, of the patient at 524.

The UE 100 may detect a predetermined threshold in one or more measurements of the patient vitals or other biosensor data at 526. Based on the biosensor data, the UE 100 may determine to administer a dosage of medication using the drug administration device 250 at 528. For example, the UE 100 may detect a predetermined threshold in one or more measurements of the biosensor data. The UE 100 may then determine a dosage amount, rate of administration and/or frequency of dosages of medication. The UE 100 then automatically activates a drug administration device to administer the medication at 530 without user input.

For example, the UE 100 may determine insulin levels after caloric intake in arterial blood flow have fallen to a predetermined threshold. The UE 100 may then determine to administer insulin to the patient through the drug delivery system. Based on the insulin level, the UE 100 may determine a dosage amount, rate of dosage and frequency of dosages.

In another example, many people have dangerous allergic reactions requiring immediate attention, e.g. food allergy or insect bite allergy. The UE 100 may detect patient vitals indicating an allergic reaction and determine to administer a dosage of epinephrine. For example, the UE 100 may detect one or more of blood pressure, respiratory rate or heart rate that exceed a predetermined threshold indicating an allergic reaction. The UE 100 then administers epinephrine or other allergy medication in response to the biosensor data. The UE 100 may thus replace epi-pens in patients with life threatening allergic reactions. Epi-pens may not be available or may be difficult for a person having an allergic reaction to administer. The UE 100 would automate this administration of life saving medication.

In an embodiment, the biosensor data is provided to a caretaker, such as a physician or pharmacy, by the UE 100. The caretaker may then instruct the UE 100 to administer the medication based on the biosensor data through the user interface. For example, the UE 100 may transmit an alert to a physician or nurse when a patient exhibits symptoms of an allergic reaction or other condition. The UE 100 may transmit the biosensor data with the alert. The caretaker may then instruct the UE 100 to administer medication based on the biosensor data.

Embodiment—Biosensor Form Factors

Due to its compact form factor, the biosensor 150 may be configured in various form factors, such as a skin patch, ear piece, on a button, etc. The biosensor may be configured for measurement of biosensor data on various skin surfaces of a patient, including on a forehead, arm, wrist, abdominal area, chest, leg, ear lobe, finger, toe, ear canal, etc.

Figure 6:
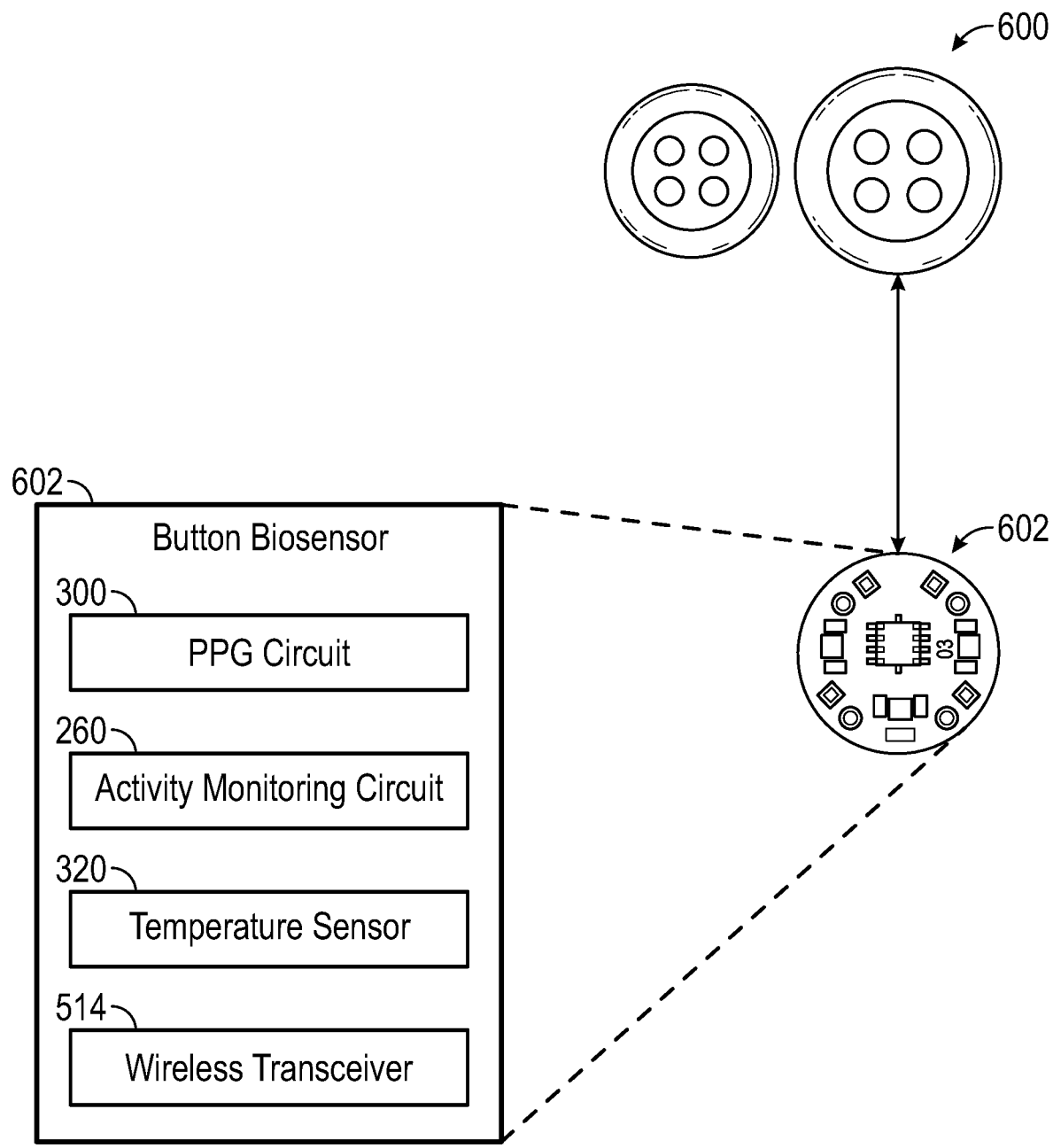
FIG. 6 illustrates an embodiment of a wearable shirt button with an integrated button biosensor.

FIG. 6 illustrates an embodiment of a wearable shirt button 600 with an integrated button biosensor 602. The button biosensor 602 includes for example a PPG circuit 300, an activity monitoring circuit 260, or temperature sensor 320. The button biosensor 602, e.g., is configured to integrate into a shirt button or clothing for measuring biosensor data. The transceiver 110 includes a wireless transceiver (positioned on an opposite side of the body facing sensor side) for communicating with the UE 100. In use, in an embodiment, the button sensor 602 detects biosensor data and transmits the biosensor data to the HM application in the UE 100 for storage and tracking. The HM application may instruct the UE 100 to display a graphical user interface (GUI) illustrating the biosensor data and a history of the biosensor data.

Figure 7:
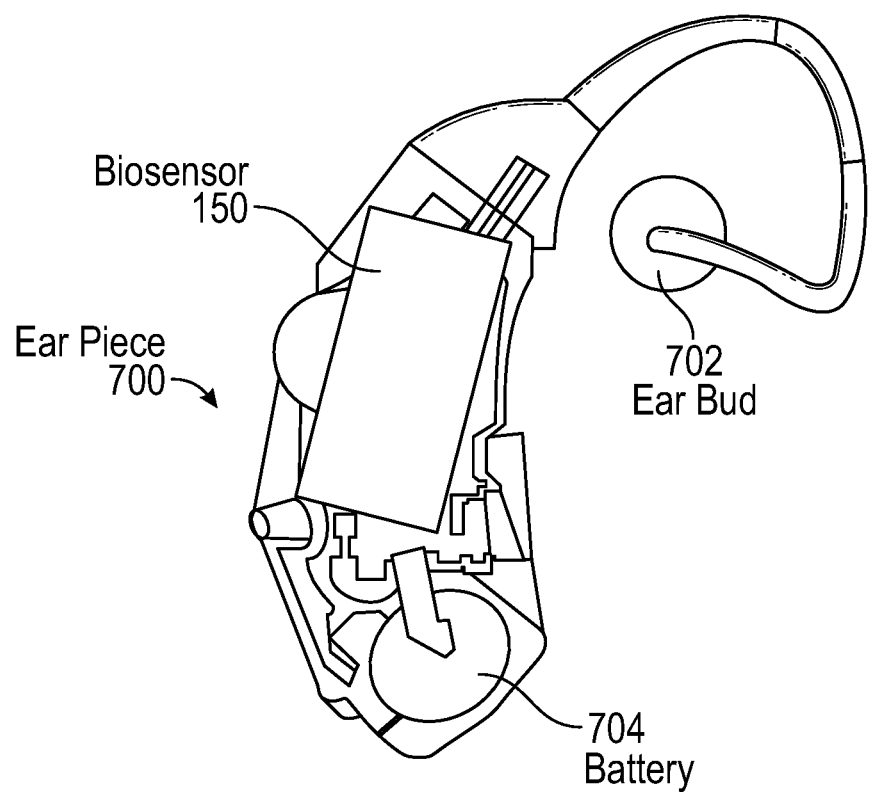
FIG. 7 illustrates a schematic block diagram of an exemplary embodiment of another form factor of the biosensor.

FIG. 7 illustrates an exemplary embodiment of another form factor of a biosensor 150. In this embodiment, a biosensor 150 is configured in an earpiece 700. The earpiece 700 includes an earbud 702. The biosensor 150 is configured to transmit light into the ear canal from one or more optical fibers in the earbud 702 and detect light from the ear canal using one or more optical fibers. The biosensor 150 may be powered by a battery 704. The biosensor 150 includes a wireless transceiver to transmit biosensor data to the UE 100.

Figure 8A:
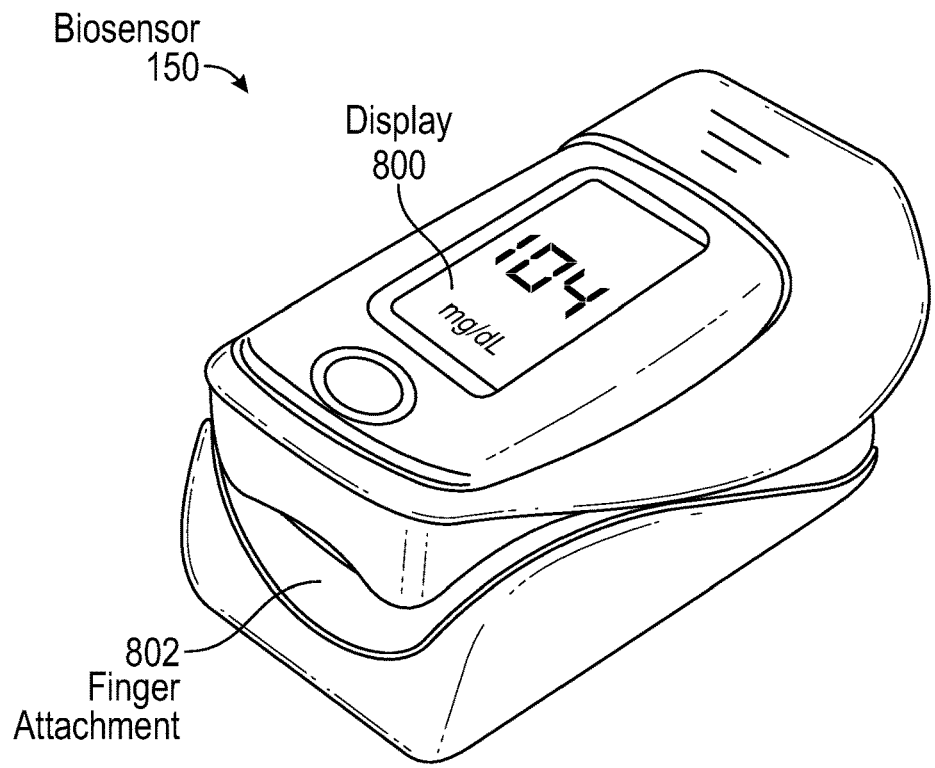
FIG. 8A illustrates an exemplary embodiment of another form factor of the biosensor.

FIG. 8A illustrates an exemplary embodiment of another form factor of the biosensor 150. In this embodiment, the biosensor 150 is configured to attach to a finger or fingertip using finger attachment 802. The finger attachment 802 is configured to securely hold a finger that is inserted into the finger attachment 802. A display 800 is implemented on the biosensor 150 with a graphical user interface (GUI) that displays biosensor data. For example, in use, the biosensor 150 measures blood glucose levels using the PPG circuit 300. The blood glucose levels are then displayed using the GUI on the display 800. The PPG circuit may also measure other patient vitals that are displayed on the display 800, such as oxygen saturation levels, temperature, respiration rates, heart rate, blood alcohol levels, digestive response, caloric intake, white blood cell count, electrolyte or other blood analyte concentrations, liver enzymes, etc. The biosensor 150 may thus provide biosensor data continuously and non-invasively. The finger biosensor 150 may also include a transceiver 110 to transmit biosensor data to the UE 100 for tracking and storage by the HM application 108.

Figure 8B:
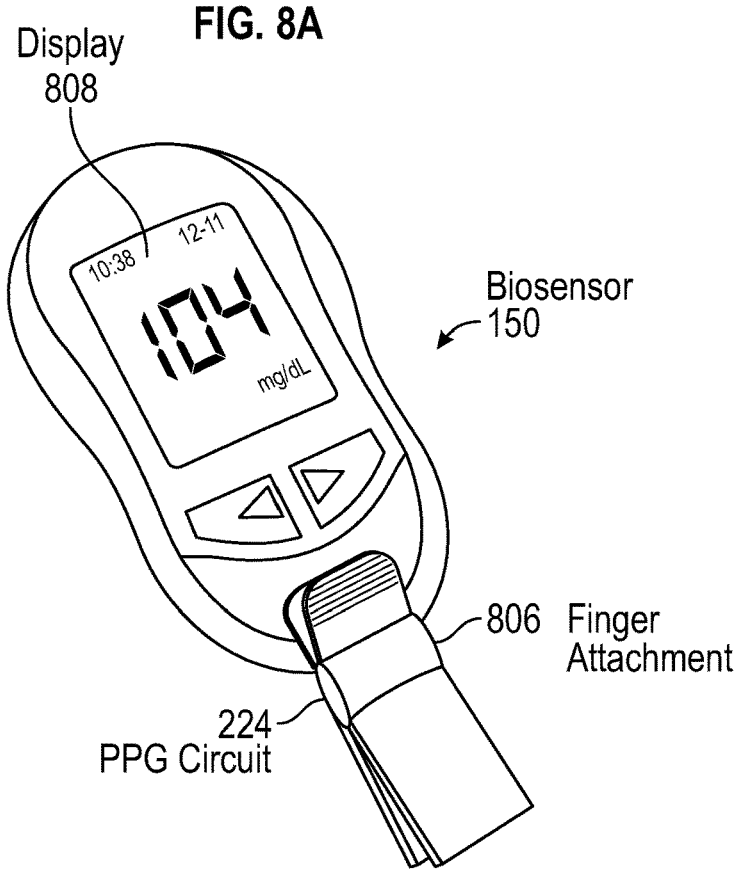
FIG. 8B illustrates an exemplary embodiment of another form factor of the biosensor.

FIG. 8B illustrates an exemplary embodiment of another form factor of the biosensor 150. In this embodiment, the biosensor 150 is configured to attach to a finger or fingertip using finger attachment 806. The finger attachment 806 includes the PPG circuit 300 and is configured to securely hold a finger that is inserted into the finger attachment 806. The finger attachment 806 may be implemented within the same encasement as the other components of the biosensor 150 or be communicatively coupled either through a wired or wireless interface to the other components of the biosensor 150. A display 808 is implemented for the biosensor 150 with a graphical user interface (GUI) that displays biosensor data including blood glucose levels. The finger biosensor 150 may also include a transceiver 110 to transmit biosensor data to the UE 100 for tracking and storage by the HM application 108.

The biosensor 150 may be configured to be implemented within the UE 100. In addition, one or more biosensors 150 in one or more form factors may be used in combination with the UE 100 to determine biosensor data at one or more areas of the body. The UE 100 may then store biosensor data measured by the one or more biosensors 150 in the EMR 708 of the patient. The HM application 108 of the UE 100 may then utilize the biosensor data for tracking and display or other functions.

Embodiment—HM Application

Figure 9:
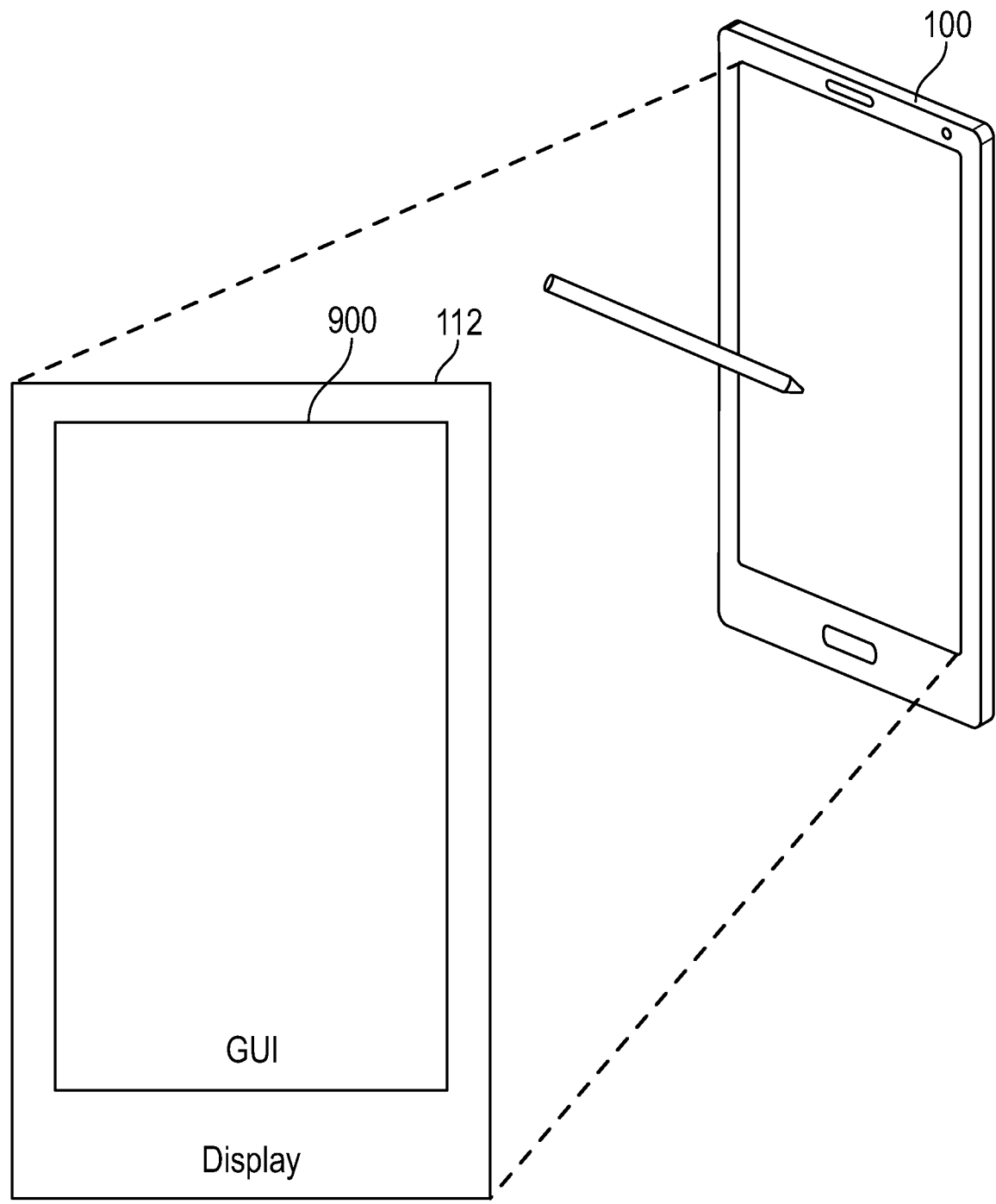
FIG. 9 illustrates an embodiment of a graphical user interface (GUI) displayed on the UE.

FIG. 9 illustrates an embodiment of a graphical user interface (GUI) 900 displayed on the UE 100. In this example, the UE 100 includes a smart phone with a touch screen. Using the HM application 108, the UE 100 is configured to generate a GUI 900 for display on the display 112. An authorized user is operable to track biosensor data using the HM application 108 and control certain functions of one or more integrated or external biosensors 150 or drug administrative devices 250.

Figure 10:
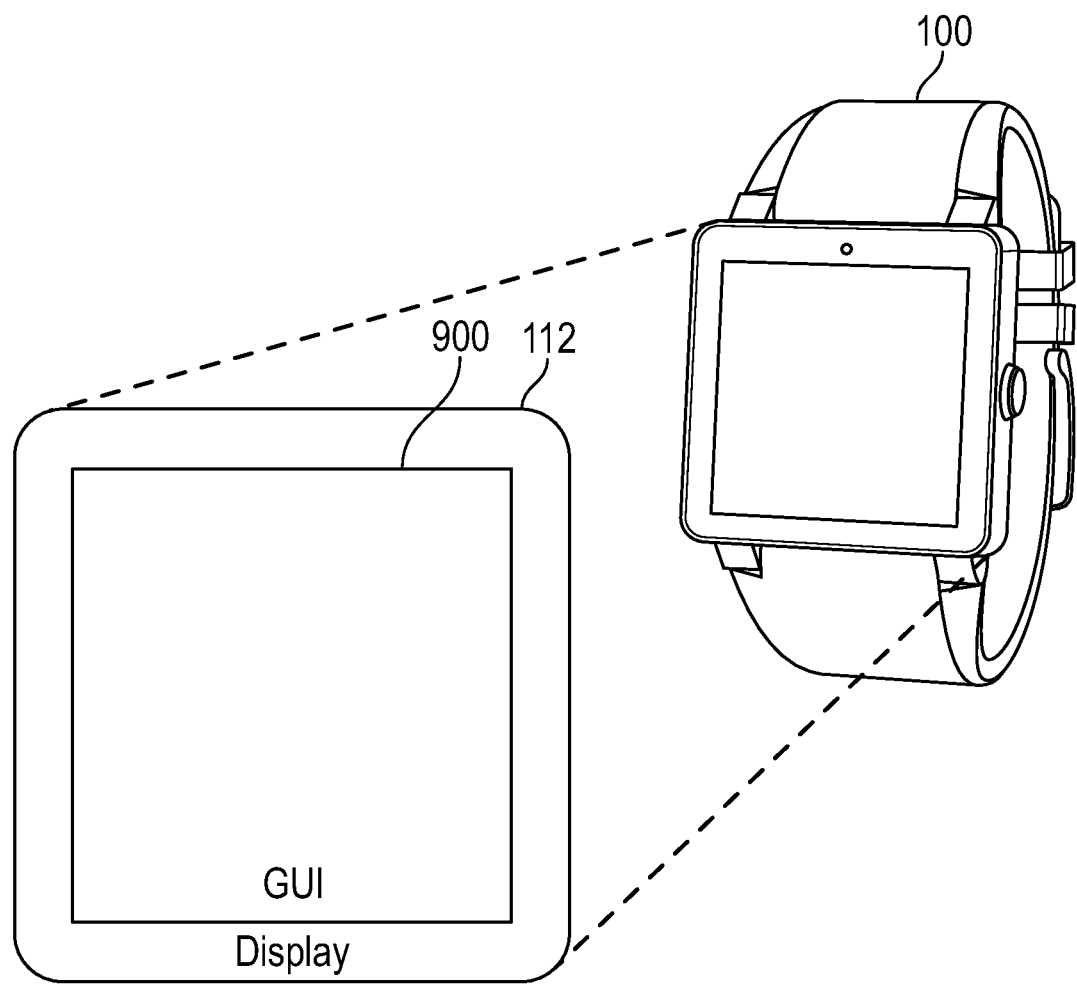
FIG. 10 illustrates an embodiment of a graphical user interface (GUI) 900 displayed on another embodiment of the UE.

FIG. 10 illustrates an embodiment of a graphical user interface (GUI) 900 displayed on another embodiment of the UE 100. In this embodiment, the UE 100 includes a smart watch. Using the HM application 108, the UE 100 is configured to generate a GUI 900 for display on the display 112. An authorized user is operable to track biosensor data using the UE 100 and control certain functions of one or more integrated or external biosensors 150 or drug administrative devices 250.

The HM application 108 may be a web-based application supported by a central application server. For example, the central application server may be a web server and support the user application via a website. The UE 100 may then use a web browser or other HTML enabled application to access either all or parts of the HM application 108 via the website supported by the central application server. The HM application 108 is then run within the web browser. In another embodiment, the HM application 108 is a stand-alone application that is downloaded to the UE 100 and is operable on the UE 100 without access to the web server or only needs to access the web server for additional information, such as biosensor data. In another embodiment, the HM application 108 may be a mobile application designed for download and use by a mobile phone or other mobile device.

The HM application 108 may generate a GUI 900 on the UE 100. The HM application 108 is configured to track and display biosensor data. For example, the HM application 108 receives biosensor data from one or more biosensors 150 and may then upon request generate a GUI 900 that includes a graphical display of glucose levels or other biosensor data. The graphical display of the biosensor data may illustrate the data over a requested period of time, such as one day, one week, etc. The HM application 108 may issue alerts when biosensor data reaches certain predetermined thresholds. For example, when the HM application 108 determines that a glucose level measurement reaches or exceeds a predetermined high or low threshold, the HM application 108 displays and sounds an alert message. In general, a good range for blood sugar levels is between 70 milligrams/deciliter (mg/Dl) and 150 mg/Dl. When the sugar level are lower than 70 mg/Dl or greater than 150 mg/Dl, the alert message may include a request or command to inject insulin by the drug administrative device 250. The HM application 108 may also track activity and generate one or more GUIs 900 that includes an activity tracker display. The activity tracker display may include periods of rest or sleep and periods of activity along with biosensor data for such periods, such as pulse, glucose levels, oxygen levels, temperature, blood pressure, etc.

Figure 11:
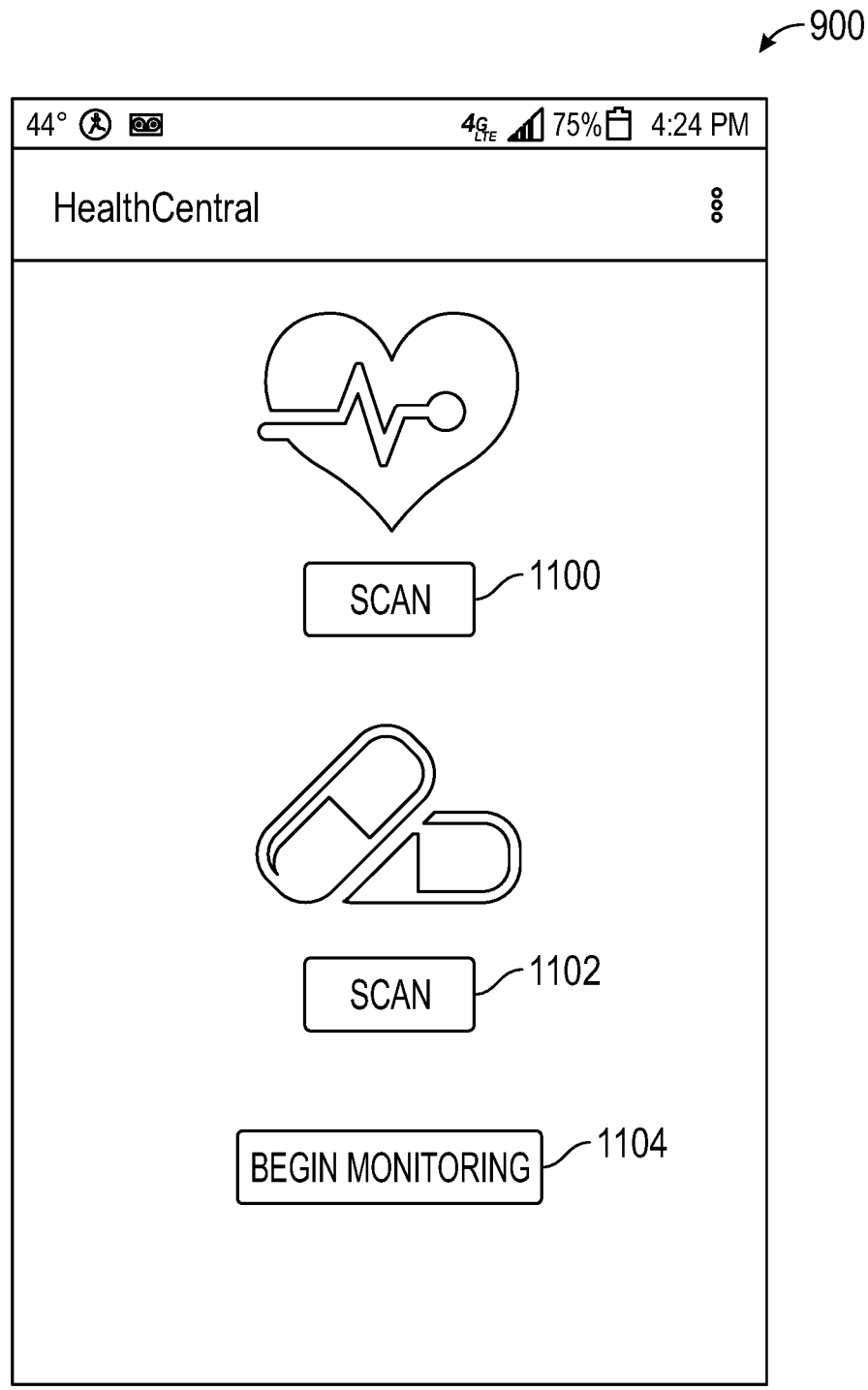
FIG. 11 illustrates a schematic block diagram of an embodiment of a graphical user interface (GUI) generated by the health monitoring application.

FIG. 11 illustrates a schematic block diagram of an embodiment of a graphical user interface (GUI) 900 generated by the HM application 108. The HM application 108 may generate the GUI 900, e.g. on the UE 100. The GUI 900 provides an interface for a user to select a command to control operation of one or more biosensors 150 integrated with the UE 100 or external to the UE 100. For example, a user may select to initiate a scan by a first biosensor 150 by selecting a first scan GUI 1100 or may select to initiate a scan by a second biosensor 150 by selecting a second scan GUI 1102. In another example, a user may select to begin monitoring by a plurality of biosensors 150 by selecting a Begin Monitoring GUI 1104.

Figure 12:
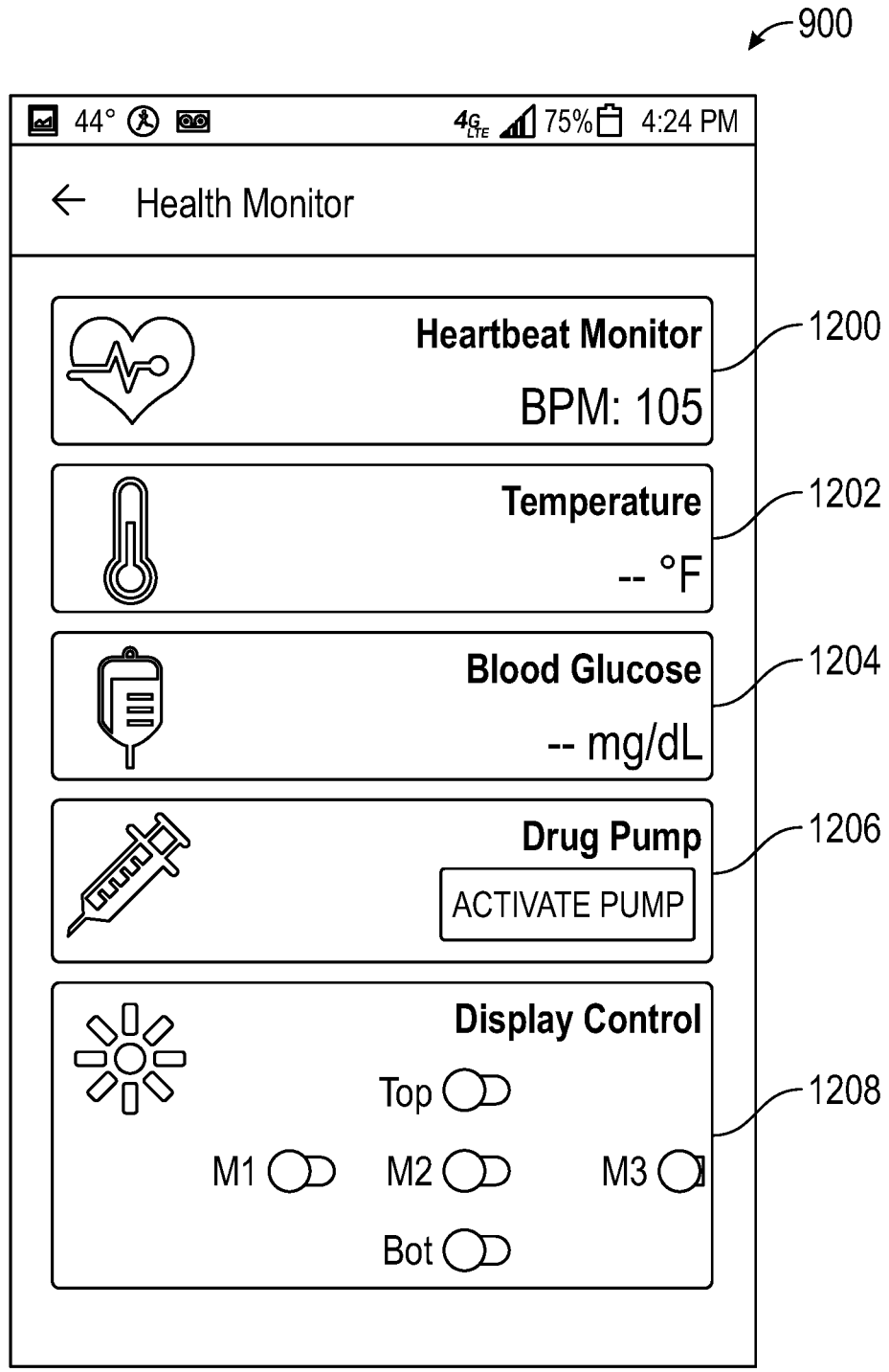
FIG. 12 illustrates a schematic block diagram of an embodiment of a graphical user interface (GUI) generated by the health monitoring application.

FIG. 12 illustrates a schematic block diagram of an embodiment of another graphical user interface (GUI) 900 generated by the HM application 108. The HM application 108 may be implemented generate the GUI 900, e.g. on the display 112 of the UE 100, based on biosensor data from one or more biosensors 150. The HM application 108 is operable to generate the GUI 900 to display monitored biosensor data. For example, the GUI 900 may display a Heartbeat Monitor GUI 1200 that tracks detected heart rate or beats per minute (BPM), e.g. BPM=105. The GUI 900 may display a Temperature GUI 1202 that illustrates measured temperature of a user, and a Blood Glucose Level GUI 1204 that illustrates measured indicator of blood glucose levels. The GUI 900 may also illustrate an Activate Pump command GUI 1206 to activate a drug administrative device 250, such as a drug pump.

The GUI 900 may also illustrate a history of readings of biosensor data. The history may display biosensor data measured over one day, multiple days, one week, one month, one year, or other specified time frame. The HM application 108 may also generate a display control GUI 1208. A user may control the display of the GUIs on the UE 100 using the display control GUI 1208.

Figure 13:
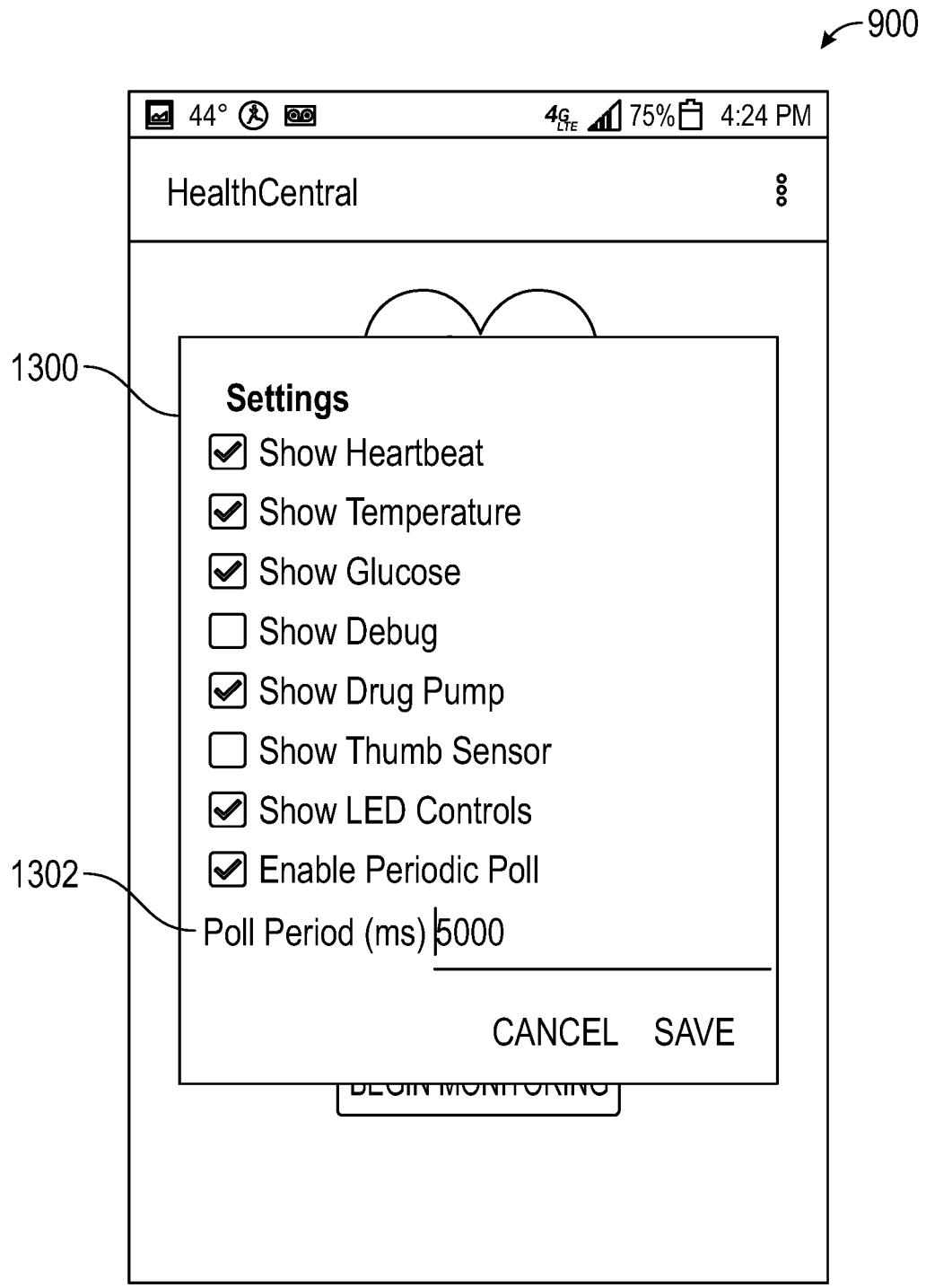
FIG. 13 illustrates a schematic block diagram of an embodiment of a graphical user interface (GUI) generated by the health monitoring application.

FIG. 13 illustrates a schematic block diagram of an embodiment of another graphical user interface (GUI) 900 generated by the HM application 108. The GUI 900 displays a Settings GUI 1300 for a user to designate settings for the GUI 900. For example, the Settings GUI 1300 may enable a user to select the various biosensor data displayed, such as heartbeat, temperature, glucose, etc. The HM application 108 may also include a poll period GUI 1302. The poll period GUI 1302 provides an interface for a user to select or input a time period or polling period for a biosensor measurement or other monitoring.

Figure 14:
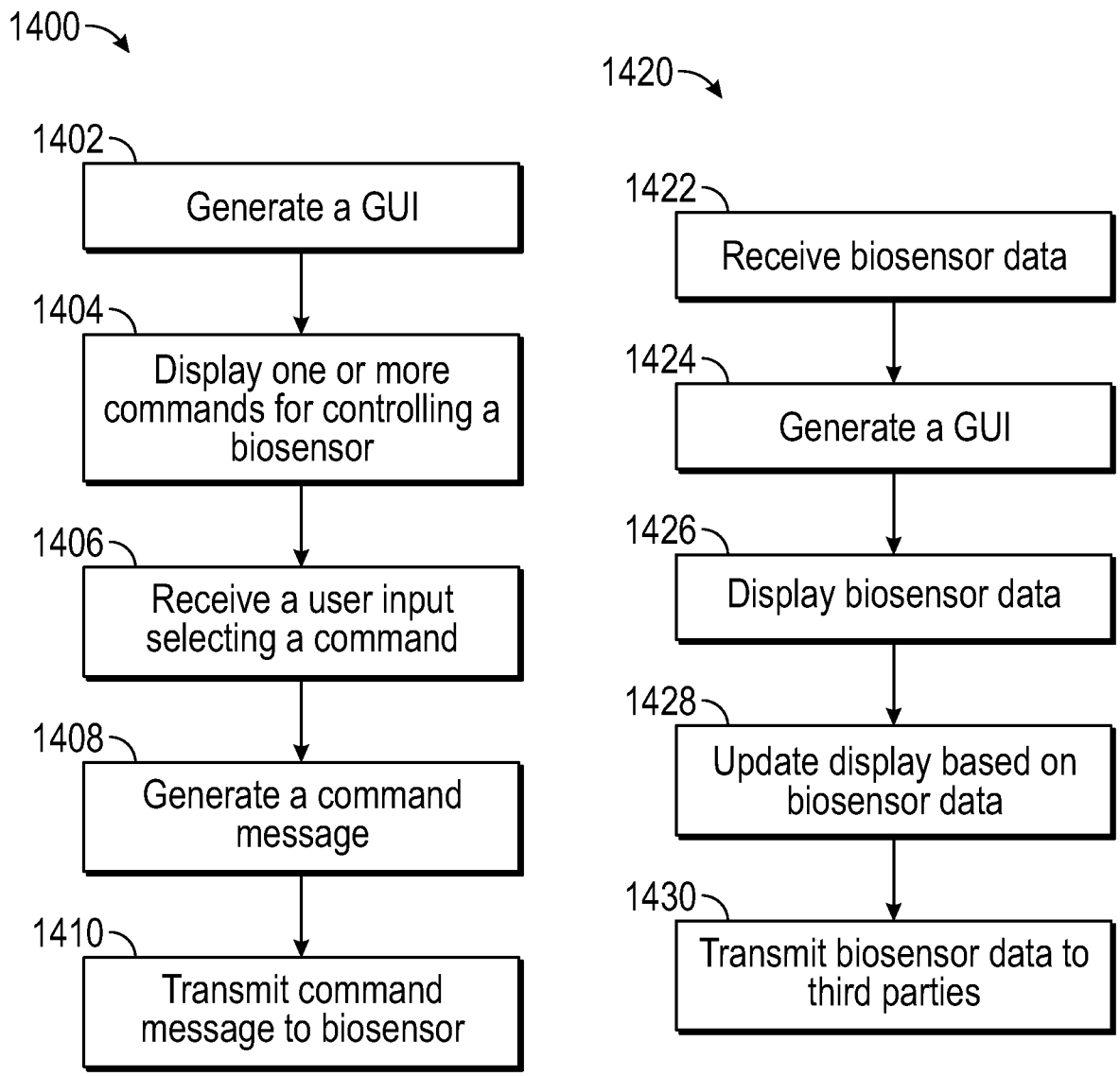
FIG. 14A illustrates a logical flow diagram of an embodiment of a method of operation of the health monitoring application of the UE.
FIG. 14B illustrates a logical flow diagram of an embodiment of another method of operation of the health monitoring application of the UE.

FIG. 14A illustrates a logical flow diagram of an embodiment of a method 1400 of operation of the HM application 108 of the UE 100. In an embodiment, the HM application 108 may generate a GUI 900 for display on the UE 100 at 1402. The GUI 900 displays one or more commands for controlling an integrated or external biosensor 150 at 1404. The HM application 108 may receive a user input selecting a command at 1406. The HM application 108 generates a command in response to the user input at 1408. The HM application 108 initiates transmission of the command to an external biosensor to perform the command or transmits the command to an integrated biosensor to perform the command at 1410.

FIG. 14B illustrates a logical flow diagram of an embodiment of another method 1420 of operation of the HM application 108 of the UE 100. In an embodiment, the HM application 108 receives biosensor data from one or more integrated or external biosensors at 1422. The HM application 108 may generate a GUI 900 that displays biosensor data on the display 112 at 1426. The HM application 108 may receive updated biosensor data from the one or more biosensors 150. The HM application 108 then updates the GUI 900 on the display 112 based on the updated biosensor data at 1428. The HM application 108 may also transmit biosensor data to third parties, such as a doctor's office or pharmacy at 1430. For example, the HM application 108 may generate messages that include requests to refill medications that are transmitted by the UE 100 to a pharmacy over a wide area network (WAN). In another example, the HM application 108 may generate messages that include biosensor data that are transmitted by the UE 100 to a doctor's hospital over a wide area network (WAN).

Embodiment of a Communication Network

Figure 15:
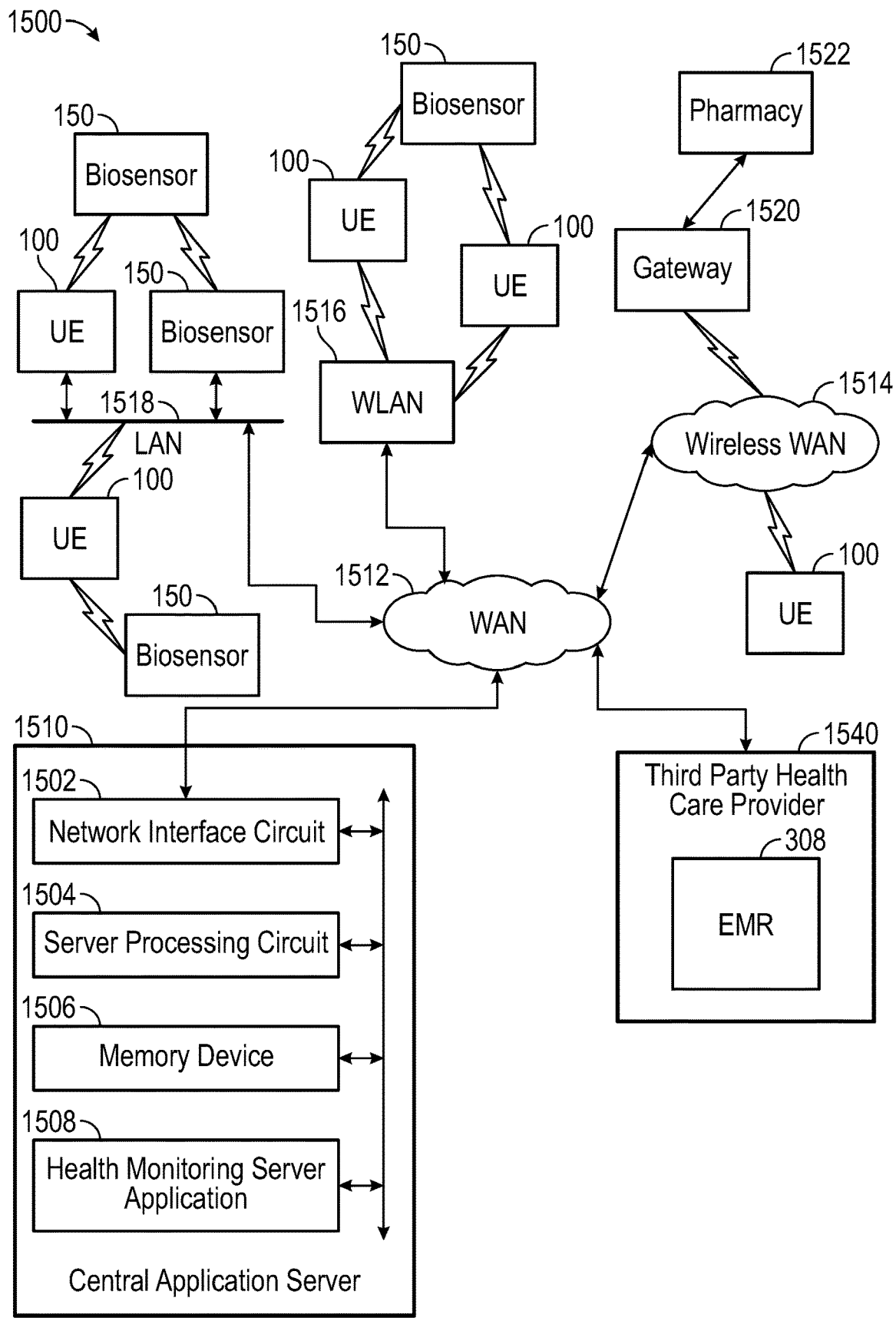
FIG. 15 illustrates a schematic block diagram of an embodiment of an exemplary communication network in which the devices described herein may operate.

FIG. 15 illustrates a schematic block diagram of an embodiment of an exemplary communication network 1500 in which the devices described herein may operate. The exemplary communication network 1500 includes one or more networks that are communicatively coupled, such as a wide area network (WAN) 1512, a wired or wireless local area network (LAN) 1516, a wireless local area network (WLAN) 1516, and a wireless wide area network (WAN) 1512. The LAN 1518 and the WLANs 1516 may operate inside a home or enterprise environment, such as a medical office, physician office, emergency care center, pharmacy or hospital or other health care provider or business. The wireless WAN 1514 may include, for example, a 3G or 4G cellular network, a GSM network, a WIMAX network, an EDGE network, a GERAN network, etc. or a satellite network or a combination thereof. The WAN 1512 includes the Internet, service provider network, other type of WAN, or a combination of one or more thereof.

One or more UEs 100 are communicatively coupled to a central application server 1510 by one or more of the exemplary networks in the communication network 1500. The central application server 1510 includes a network interface circuit 1502 and a server processing circuit 1504. The network interface circuit 1502 includes an interface for wireless and/or wired network communications with one or more of the exemplary networks in the communication network 1500. The network interface circuit 1502 may also include authentication capability that provides authentication prior to allowing access to some or all of the resources of the central application server 1510. The network interface circuit 1502 may also include firewall, gateway and proxy server functions.

The central application server 1510 also includes a server processing circuit 1504 and a memory device 1506. For example, the memory device 1506 is a non-transitory, processor readable medium that stores instructions from the health monitoring server application 1508 which when executed by the server processing circuit 1504, causes the server processing circuit 1504 to perform one or more functions described herein. In an embodiment, the memory device 1506 stores biosensor data for a plurality of patients transmitted to the central application server 1510 from the plurality of UE 100.

The central application server 1510 includes a health monitoring server application 1508. The health monitoring server application 1508 is operable to communicate with the plurality of UE 100. The health monitoring server application 1508 may be a web-based application supported by the central application server 1510. For example, the central application server 1510 may be a web server and support the health monitoring server application 1508 via a website. In another embodiment, the health monitoring server application 1508 is a stand-alone application that is downloaded to the UE 100 by the central application server 1510 and is operable on the UE 100 without access to the central application server 1510 or only needs to accesses the central application server 1510 for additional information, such as biosensor data. Using the HM application 108, the plurality of UE 100 are configured to track biosensor data and control certain functions of the plurality of biosensors 150. In addition, the health monitoring server application 1508 supports the HM application 108 on one or more of the plurality of UE 100. The UE 100 may communicate directly with one or more external biosensors 150 or indirectly through one or more networks.

The central application server 1510 may also be operable to communicate with a third party over the communication network 1220 to provide biosensor data. For example, the HM application 108 may provide biosensor data to a third party health care provider 1540, such as a medical office, hospital, nursing home, etc. For example, the HM application 108 may transmit heart rate information or pulse rate information or other biosensor data, to the third party health care provider 1540 over the communication network 1500 as requested or needed. The HM application 108 may also communicate with a pharmacy 1522 to request medication refills or provide biosensor data.

Figure 16:
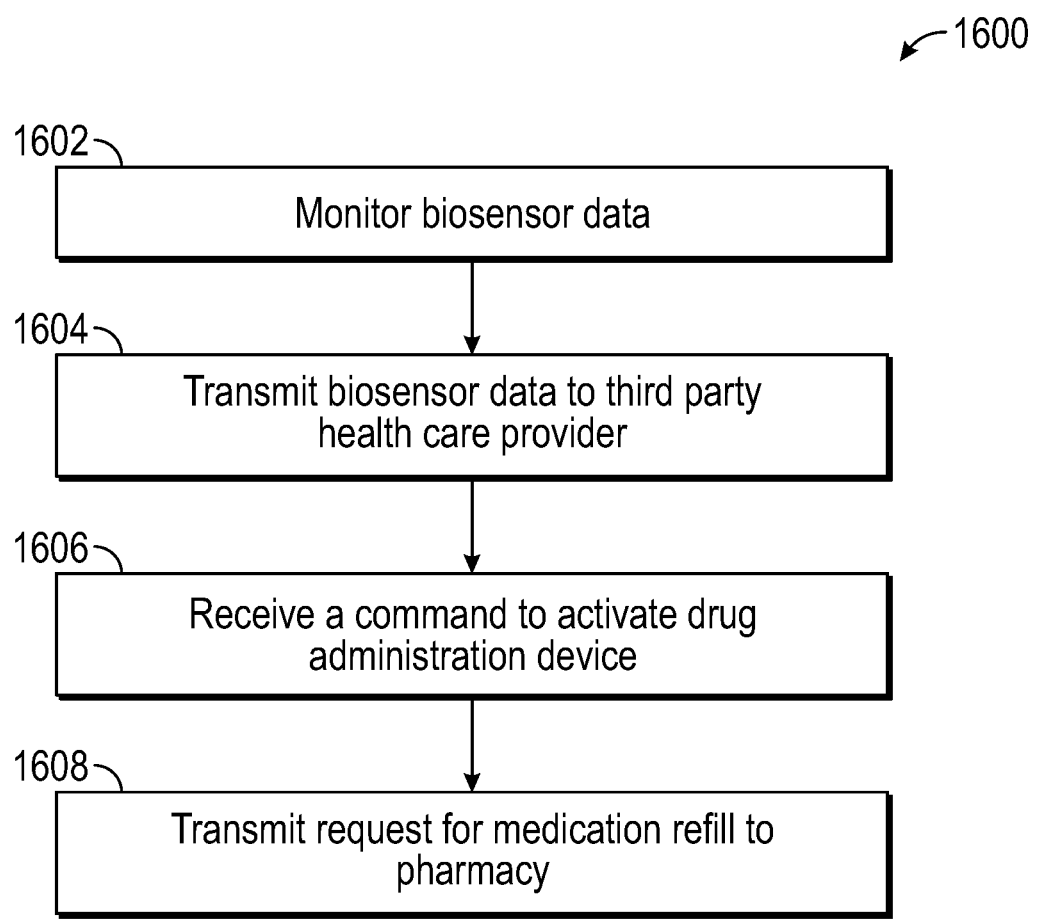
FIG. 16 illustrates a logic flow diagram of an embodiment of another method of operation of the health monitoring application of the UE.

FIG. 16 illustrates a logic flow diagram of an exemplary embodiment of a method 1600 of operation of the HM application 108 of the UE 100. The HM application 108 is configured to receive and monitor biosensor data from one or more external or integrated biosensors 150 at 1602. For example, the one or more biosensors 150 may detect an indicator of glucose levels, alcohol levels or other analytes. In addition, the one or more biosensors 150 may also detect blood pressure, peripheral oxygen ($SpO_2$) saturation amounts, body temperature, various electrolytes and many common blood analytic levels, such as bilirubin amount and sodium and potassium. The one or more biosensors 150 may also detect blood alcohol levels. The biosensor data is obtained by the HM application 108 and transmitted by the UE 100 to a third party health care provider 1540 at 1604. The third party health care provider 1540 may analyze the biosensor data and generate a message to the UE 100 in response to the biosensor data. For example, the third party health care provider 1540 may request that a user administer medication or request that the UE 100 automatically activate a drug administration device to administer medication at 1606. For example, the biosensor data may include pulse rate or blood pressure or other biosensor data. Based on the biosensor data, the third party health care provider 1540 may determine that a patient is having a dangerous allergic reaction and transmits a command to automatically activate a drug administration device to administer an allergy medication. In another example, the biosensor data indicates a glucose level above a predetermined threshold. The activity monitor may also indicate slow or no activity by the user of the UE 100. The third party health care provider 1540 may determine the patient is not able to administer medication by themselves and so transmits a command to the UE 100 to automatically activate a drug administration device to administer insulin.

The HM application 108 may also generate a request for medication refill to a pharmacy at 1608. The request may be transmitted to a pharmacy 1522 by the UE 100 over the communication network 1500. The request may be generated in response to user input or based on an indicator from the drug administration device of low medication levels.

Embodiment—PPG Circuit

Figure 17:
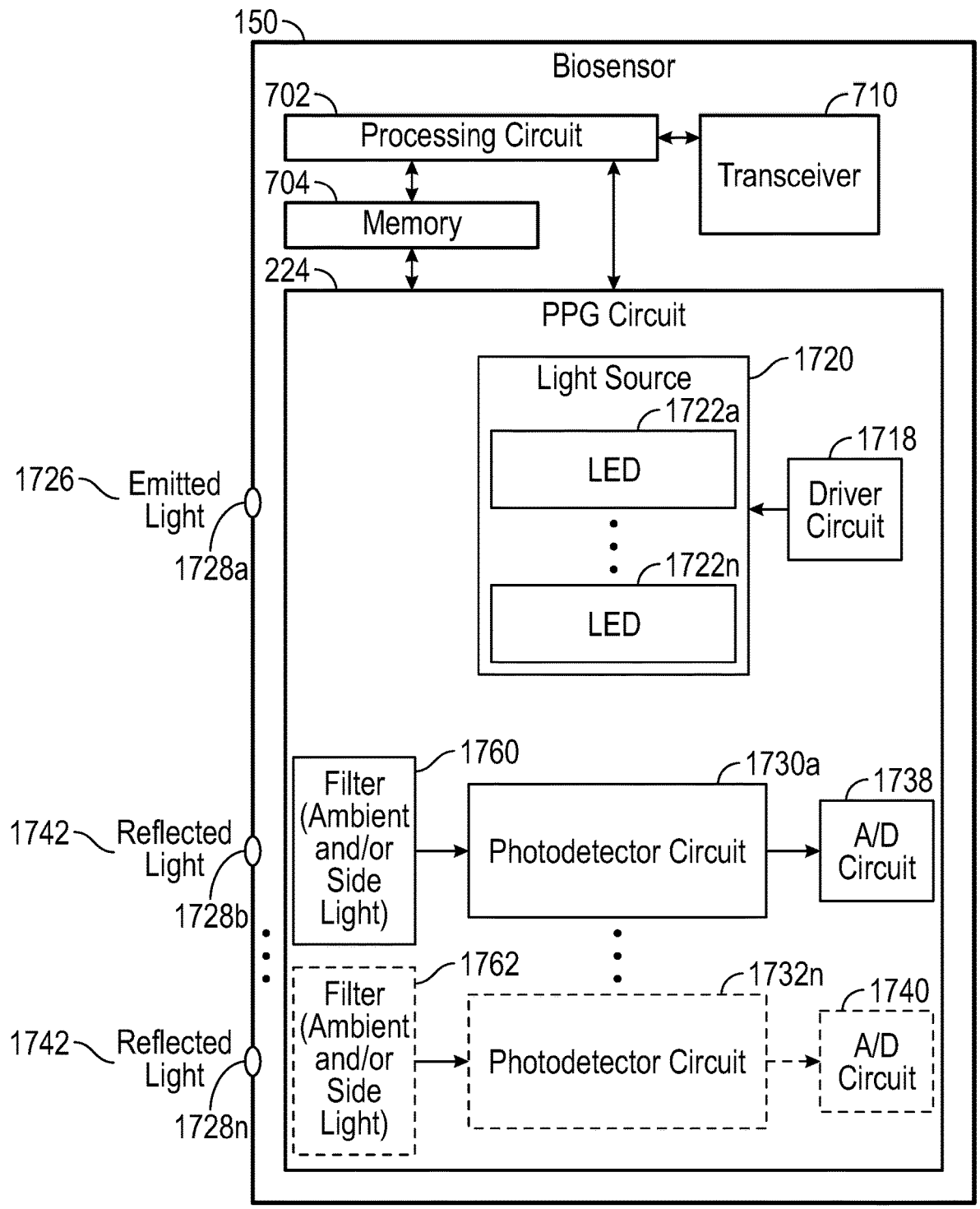
FIG. 17 illustrates a schematic block diagram illustrating an embodiment of the PPG circuit in more detail.

FIG. 17 illustrates a schematic block diagram illustrating an embodiment of the PPG circuit 300 in more detail. The PPG circuit 300 implements photoplethysmography (PPG) techniques for obtaining concentration levels or indicators of one or more substances in pulsating arterial blood flow. The PPG circuit 300 includes a light source 1720 having a plurality of light sources, such as LEDs 1722*a-n*, configured to emit light through at least one aperture 1728*a*. The PPG circuit 300 is configured to direct the emitted light at an outer or epidermal layer of skin tissue of a patient. The plurality of light sources are configured to emit light in one or more spectrums, including infrared (IR) light, ultraviolet (UV) light, near IR light or visible light, in response to driver circuit 1718. For example, the biosensor 150 may include a first LED 1722*a* that emits visible light and a second LED 1722*b* that emits infrared light and a third LED 1722*c* that emits UV light, etc. In another embodiment, one or more of the light sources 1722*a-n* may include tunable LEDs or lasers operable to emit light over one or more frequencies or ranges of frequencies or spectrums in response to driver circuit 1718.

In an embodiment, the driver circuit 1718 is configured to control the one or more LEDs 1722*a-n* to generate light at one or more frequencies for predetermined periods of time. The driver circuit 118 may control the LEDs 1722*a-n* to operate concurrently or progressively. The driver circuit 118 is configured to control a power level, emission period and frequency of emission of the LEDs 1722*a-n*. The biosensor 150 is thus configured to emit one or more frequencies of light in one or more spectrums that is directed at the surface or epidermal layer of the skin tissue of a patient.

The PPG circuit 300 further includes one or more photodetector circuits 1730*a-n*. For example, a first photodetector circuit 1730 may be configured to detect visible light and the second photodetector circuit 1730 may be configured to detect IR light. The first photodetector circuit 1730 and the second photodetector circuit 130 may also include a first filter 1760 and a second filter 1762 configured to filter ambient light and/or scattered light. For example, in some embodiments, only light received at an approximately perpendicular angle to the skin surface of the patient is desired to pass through the filters. The first photodetector circuit 1730 and the second photodetector circuit 1732 are coupled to a first A/D circuit 1738 and a second A/D circuit 1740. The A/D circuits 1738 and 1740 may also include an amplifier and other components needed to generate the spectral response. In another aspect, the plurality of photodetectors 1730 is coupled in parallel to a single amplifier and A/D circuit 1738. The light detected by each of the photodetectors 1730 is thus added and amplified to generate a single spectral response.

In another embodiment, a single photodetector circuit 1730 may be implemented operable to detect light over multiple spectrums or frequency ranges. For example, the photodetector circuit 1730 may include a Digital UV Index/IR/Visible Light Sensor such as Part No. Si1145 from Silicon Labs™.

The one or more photodetector circuits 1730 include a spectrometer or other type of circuit configured to detect an intensity of light as a function of wavelength or frequency to obtain a spectral response. The one or more photodetector circuits 1730 detect the intensity of light either transmitted through or reflected from tissue of a patient that enters one or more apertures 1728*b-n* of the biosensor 150. For example, the light may be detected from transmissive absorption (e.g., through a fingertip or ear lobe) or from reflection (e.g., reflected from a forehead or stomach tissue). The photodetector circuits 1730*a-n* then obtain a spectral response of the detected light by measuring the intensity of light either transmitted or reflected to the photodiodes.

Figure 18:
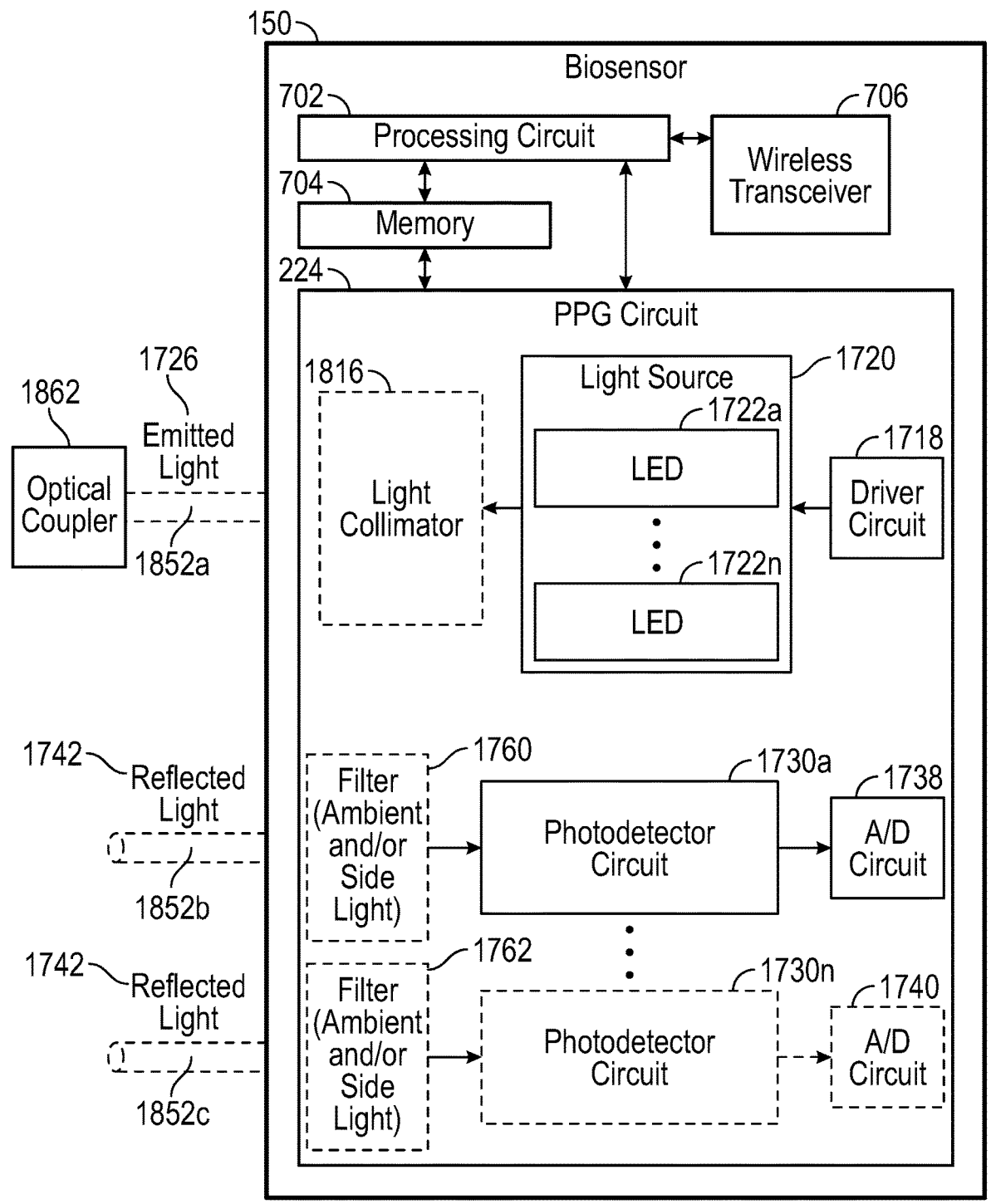
FIG. 18 illustrates a schematic block diagram of another exemplary embodiment of the the PPG circuit.

FIG. 18 illustrates a schematic block diagram of another exemplary embodiment of the the PPG circuit 300. In this embodiment, the PPG circuit 300 is configured for emitting and detecting light through one or more optical fibers 1852*a-c*. The PPG circuit 300 is optically coupled to a plurality of optical fibers 1852*a-c*. In an embodiment, the plurality of optical fibers 1852*a-c* includes a first optical fiber 1852*a* optically coupled to the light source 1720. An optical coupler (not shown) to spread the angle of light emitted from the optical fiber 1852*a* may also be implemented. The optical fiber 1852*a* may have a narrow viewing angle such that an insufficient area of skin surface is exposed to the light. An optical coupler 1862 may be used to widen the viewing angle to increase the area of skin surface exposed to the light.

A second optical fiber 1852*b* is optically coupled to a first photodetector circuit 1730*a* and a third optical fiber 1852*c* is optically coupled to the second photodetector circuit 1730*n*. Other configurations and numbers of the plurality of optical fibers 1852 may also be implemented.

In one aspect, the plurality of optical fibers 1852 is situated within an outer ear canal to transmit and detect light in the ear canal. A light collimator 1816, such as a prism, may be used to align a direction of the light emitted from the light source 1720. One or more filters 1760, 1762 may optionally be implemented to receive the reflected light 1742 from the plurality of optical fibers 1852*b*, 1852*c*. However, the filters 1760, 1762 may not be needed as the plurality of optical fibers 1852*b*, 1852*c* may be sufficient to filter ambient light and/or scattered light.

Figure 19:
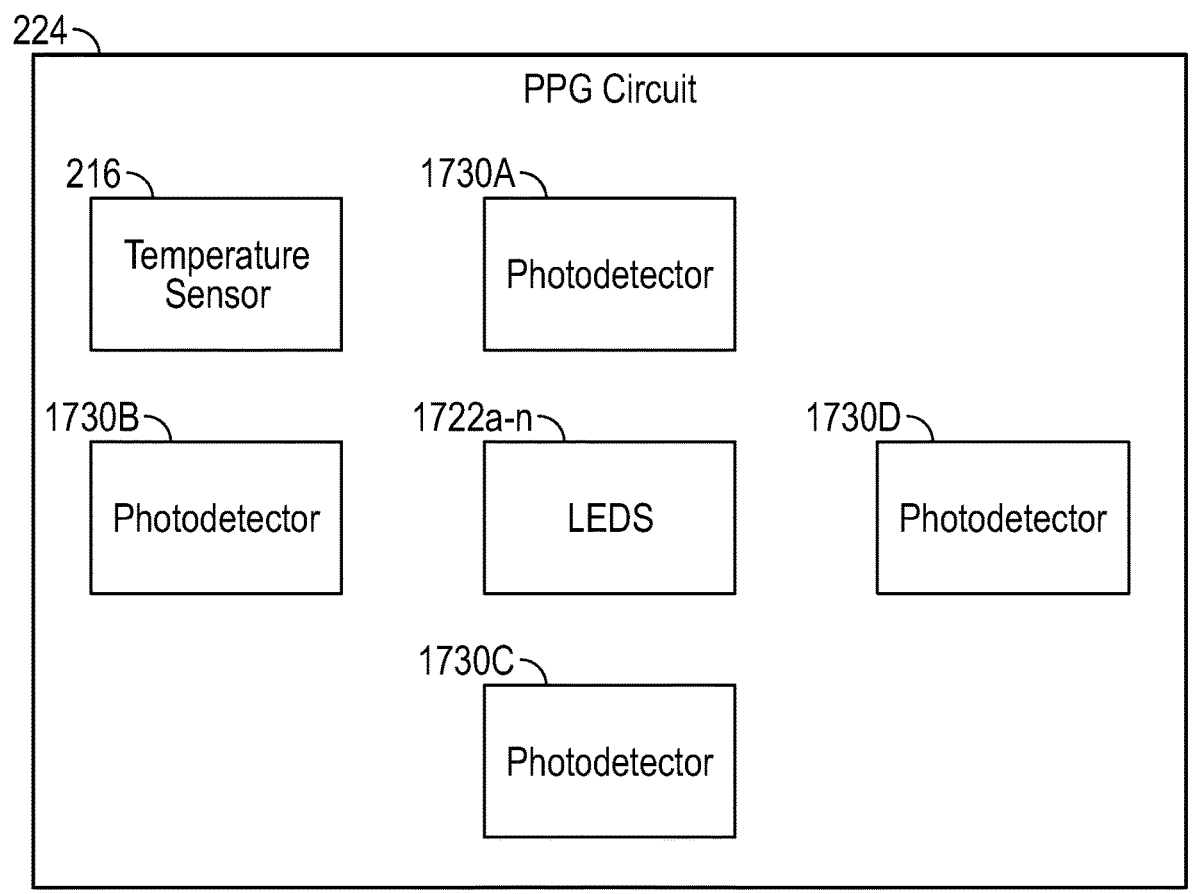
FIG. 19 illustrates a schematic block diagram of an embodiment of the PPG circuit with a plurality of photodetectors.

FIG. 19 illustrates a schematic block diagram of an embodiment of the PPG circuit 300 with a plurality of photodetectors 1730. In one aspect, the plurality of photodetectors 1730 are situated in different physical positions and orientations in the biosensor 150. For example, at least four photodetectors 1730*a*, 1730*b*, 1730*c* and 1730*d* are situated in the biosensor 150 in four different physical positions in a North-South and East-West orientation or polarity. The output signals of the plurality of photodetectors are coupled in parallel to the amplifier and A/D circuit 1738. The light signals detected by each of the photodetectors 1730 through an aperture 1728 in the biosensor are added and amplified to generate a single spectral response. The spectral response is thus more robust and less affected by motion artifacts and movement of the biosensor 150. The LEDs 1722*a-n* may be situated centrally to the physical position of the plurality of photodetectors 1730. The temperature sensor 320 may also be physically situated near the PPG circuit 300 to detect temperature through an aperture 1728.

Embodiment—PPG Measurement of Blood Flow

One or more of the embodiments of the biosensor 150 described herein are configured to detect a concentration level or indicator of one or more substances within blood flow, such as analyte levels, nitric oxide levels, insulin resistance or insulin response after caloric intake and predict diabetic risk or diabetic precursors. The biosensor 150 may detect insulin response, vascular health, cardiovascular sensor, cytochrome P450 proteins (e.g. one or more liver enzymes or reactions), digestion phase 1 and 2 or caloric intake. The biosensor 150 may even be configured to detect proteins or other elements or compounds associated with cancer. The biosensor 150 may also detect various electrolytes and many common blood analytic levels, such as bilirubin amount and sodium and potassium. For example, the biosensor 150 may detect sodium NACL concentration levels in the arterial blood flow to determine dehydration. The biosensor 150 may also detect blood alcohol levels in vivo in the arterial blood flow. Because blood flow to the skin can be modulated by multiple other physiological systems, the biosensor 150 may also be used to monitor breathing, hypovolemia, and other circulatory conditions. The biosensor 150 may also detect blood pressure, peripheral oxygen ($SpO_2$ or $SaO_2$) saturation, heart rate, respiration rate or other patient vitals. The biosensor 150 may also be used to detect sleep apnea based on oxygen saturation levels and activity monitoring during sleep.

In use, the biosensor 150 performs PPG techniques using the PPG circuit 300 to detect the concentration levels of substances in blood flow. In one aspect, the biosensor 150 analyzes reflected visible or IR light to obtain a spectrum response such as, the resonance absorption peaks of the reflected visible, UV or IR light. The spectrum response includes spectral lines that illustrate an intensity or power or energy at a wavelength or range of wavelengths in a spectral region of the detected light.

The ratio of the resonance absorption peaks from two different frequencies can be calculated and based on the Beer-Lambert law used to obtain various levels of substances in the blood flow. First, the spectral response of a substance or substances in the arterial blood flow is determined in a controlled environment, so that an absorption coefficient $\alpha_{g1}$ can be obtained at a first light wavelength $\lambda_1$ and at a second wavelength $\lambda_2$. According to the Beer-Lambert law, light intensity will decrease logarithmically with path length l (such as through an artery of length l). Assuming then an initial intensity Ln of light is passed through a path length l, a concentration $C_g$ of a substance may be determined using the following equations:

At the first wavelength $\lambda_1$, $I_1 = I_{in1} * 10^{-(\alpha_{g1} C_{gw} + \alpha_{w1} C_w) * l}$ At the first wavelength $\lambda_2$, $I_2 = I_{in2} * 10^{-(\alpha_{g2} C_{gw} + \alpha_{w2} C_w) * l}$ wherein:
$I_{in1}$ is the intensity of the initial light at $\lambda_1$
$I_{in2}$ is the intensity of the initial light at $\lambda_2$
$\alpha_{g1}$ is the absorption coefficient of the substance in arterial blood at $\lambda_1$
$\alpha_{g2}$ is the absorption coefficient of the substance in arterial blood at $\lambda_2$
$\alpha_{w1}$ is the absorption coefficient of arterial blood at $\lambda_1$
$\alpha_{w2}$ is the absorption coefficient of arterial blood at $\lambda_2$
$C_{gw}$ is the concentration of the substance and arterial blood
$C_w$ is the concentration of arterial blood
Then letting R equal:

$$R = \frac{\log 10\left(\frac{I1}{Iin1}\right)}{\log 10\left(\frac{I2}{Iin2}\right)}$$

The concentration of the substance Cg may then be equal to:

$$Cg = \frac{Cgw}{Cgw + Cw} = \frac{\alpha_{w2} R - \alpha_{w1}}{(\alpha_{w2} - \alpha_{gw2}) * R - (\alpha_{w1} - \alpha_{gw1})}$$

The biosensor 150 may thus determine the concentration of various substances in arterial blood using spectroscopy at two different wavelengths using Beer-Lambert principles.

The biosensor 150 determines concentration of one or more substances using Beer-Lambert principles. The biosensor 150 transmits light at least at a first predetermined wavelength and at a second predetermined wavelength. The biosensor 150 detects the light (reflected from the skin or transmitted through the skin) and analyzes the spectral response at the first and second wavelengths to detect an indicator or concentration level of one or more substances in the arterial blood flow. In general, the first predetermined wavelength is selected that has a high absorption coefficient for the targeted substance while the second predetermined wavelength is selected that has a low absorption coefficient for the targeted substance. Thus, it is generally desired that the spectral response for the first predetermined wavelength have a higher intensity level than the spectral response for the second predetermined wavelength.

In another aspect, the biosensor 150 may transmit light at the first predetermined wavelength and in a range of approximately 1 nm to 50 nm around the first predetermined wavelength. Similarly, the biosensor 150 may transmit light at the second predetermined wavelength and in a range of approximately 1 nm to 50 nm around the second predetermined wavelength. The range of wavelengths is determined based on the spectral response since a spectral response may extend over a range of frequencies, not a single frequency (i.e., it has a nonzero linewidth). The light that is reflected or transmitted light by the target substance may by spread over a range of wavelengths rather than just the single predetermined wavelength. In addition, the center of the spectral response may be shifted from its nominal central wavelength or the predetermined wavelength. The range of 1 nm to 50 nm is based on the bandwidth of the spectral response line and should include wavelengths with increased light intensity detected for the targeted substance around the predetermined wavelength.

The first spectral response of the light over the first range of wavelengths including the first predetermined wavelength and the second spectral response of the light over the second range of wavelengths including the second predetermined wavelengths is then generated. The biosensor 150 analyzes the first and second spectral responses to detect an indicator or concentration level of one or more substances in the arterial blood flow.

Photoplethysmography (PPG) is used to measure time-dependent volumetric properties of blood in blood vessels due to the cardiac cycle. For example, the heartbeat affects volume of arterial blood flow and the concentration of absorption levels being measured in the arterial blood flow. Over a cardiac cycle, pulsating arterial blood changes the volume of blood flow in an artery. Incident light $I_O$ is directed at a tissue site and a certain amount of light is reflected or transmitted and a certain amount of light is absorbed. At a peak of arterial blood flow or arterial volume, the reflected/transmitted light $I_L$ is at a minimum due to absorption by the venous blood, nonpulsating arterial blood, pulsating arterial blood, other tissue, etc. At a minimum of arterial blood flow or arterial volume during the cardiac cycle, the transmitted/reflected light $I_H$ is at a maximum due to lack of absorption from the pulsating arterial blood.

The biosensor 150 is configured to filter the reflected/transmitted light $I_L$ of the pulsating arterial blood from the transmitted/reflected light $I_H$. This filtering isolates the light due to reflection/transmission of substances in the pulsating arterial blood from the light due to reflection/transmission from venous (or capillary) blood, other tissues, etc. The biosensor 150 may then measure the concentration levels of one or more substances from the reflected/transmitted light $I_L$ in the pulsating arterial blood. Though the above has been described with respect to arterial blood flow, the same principles described herein may be applied to venous blood flow.

In general, the relative magnitudes of the AC and DC contributions to the reflected/transmitted light signal I may be used to substantially determine the differences between the diastolic time and the systolic points. In this case, the difference between the reflected light $I_L$ and reflected light $I_H$ corresponds to the AC contribution of the reflected light (e.g. due to the pulsating arterial blood flow). A difference function may thus be computed to determine the relative magnitudes of the AC and DC components of the reflected light I to determine the magnitude of the reflected light $I_L$ due to the pulsating arterial blood. The described techniques herein for determining the relative magnitudes of the AC and DC contributions is not intended as limiting. It will be appreciated that other methods may be employed to isolate or otherwise determine the relative magnitude of the light $I_L$ due to pulsating arterial blood flow.

Figure 20:
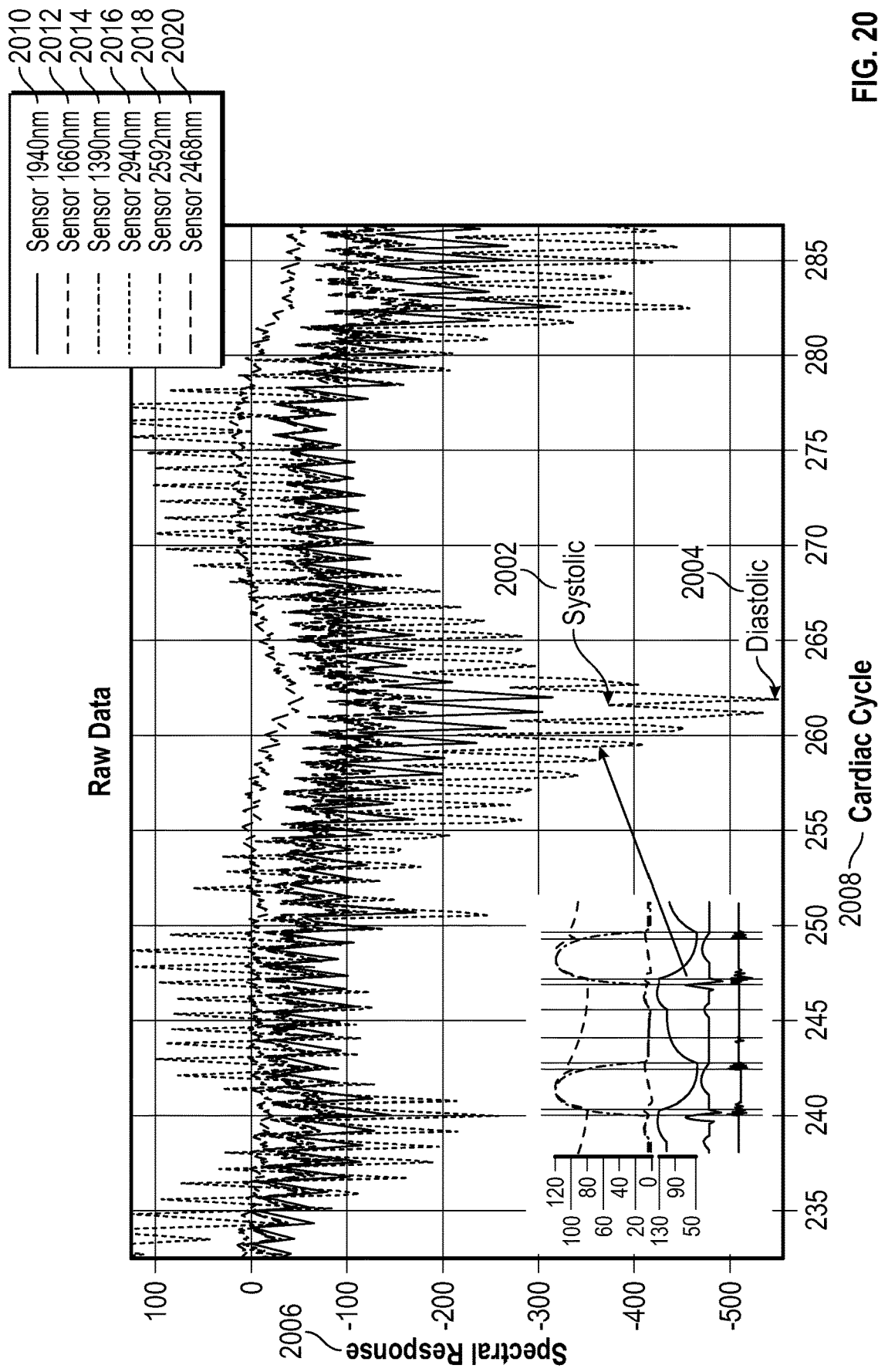
FIG. 20 illustrates a schematic diagram of a graph of actual clinical data obtained using PPG techniques at a plurality of wavelengths.

FIG. 20 illustrates a schematic diagram of a graph of actual clinical data obtained using PPG techniques at a plurality of wavelengths. The biosensor 150 emits light having a plurality of wavelengths during a measurement period. The light at each wavelength (or range of wavelengths) may be transmitted concurrently or sequentially. The intensity of the reflected light at each of the wavelengths (or range of wavelengths) is detected and the spectral response is measured over the measurement period. The spectral response 2006 for the plurality of wavelengths obtained using the biosensor in clinical trials is shown in FIG. 20. In this clinical trial, two biosensors 150 attached to two separate fingertips of a patient were used to obtain the spectral responses 2006. The first biosensor 150 obtained the spectral response for a wavelength at 940 nm 2010, a wavelength at 660 nm 2012 and a wavelength at 390 nm 2014. The second biosensor 150 obtained the spectral response for a wavelength at 940 nm 2016, a wavelength at 592 nm 2018 and a wavelength at 468 nm 2020.

In one aspect, the spectral response of each wavelength may be aligned based on the systolic 2002 and diastolic 2004 points in their spectral responses. This alignment is useful to associate each spectral response with a particular stage or phase of the pulse-induced local pressure wave within the blood vessel (which may mimic the cardiac cycle 2008 and thus include systolic and diastolic stages and sub-stages thereof). This temporal alignment helps to determine the absorption measurements acquired near a systolic point in time of the cardiac cycle 2008 and near the diastolic point in time of the cardiac cycle 2008 associated with the local pressure wave within the patient's blood vessels. This measured local pulse timing information may be useful for properly interpreting the absorption measurements in order to determine the relative contributions of the AC and DC components measured by the biosensor 150. So for one or more wavelengths, the systolic points 2002 and diastolic points 2004 in the spectral response are isolated or determined. These systolic points 2002 and diastolic points 2004 for the one or more wavelengths may then be aligned as a method to discern concurrent responses across the one or more wavelengths.

In another embodiment, the systolic points 2002 and diastolic points 2004 in the absorbance measurements are temporally correlated to the pulse-driven pressure wave within the arterial blood vessels—which may differ from the cardiac cycle. In another embodiment, the biosensor 150 may concurrently measure the intensity reflected at each the plurality of wavelengths. Since the measurements are concurrent, no alignment of the spectral responses of the plurality of wavelengths may be necessary.

Figure 21:
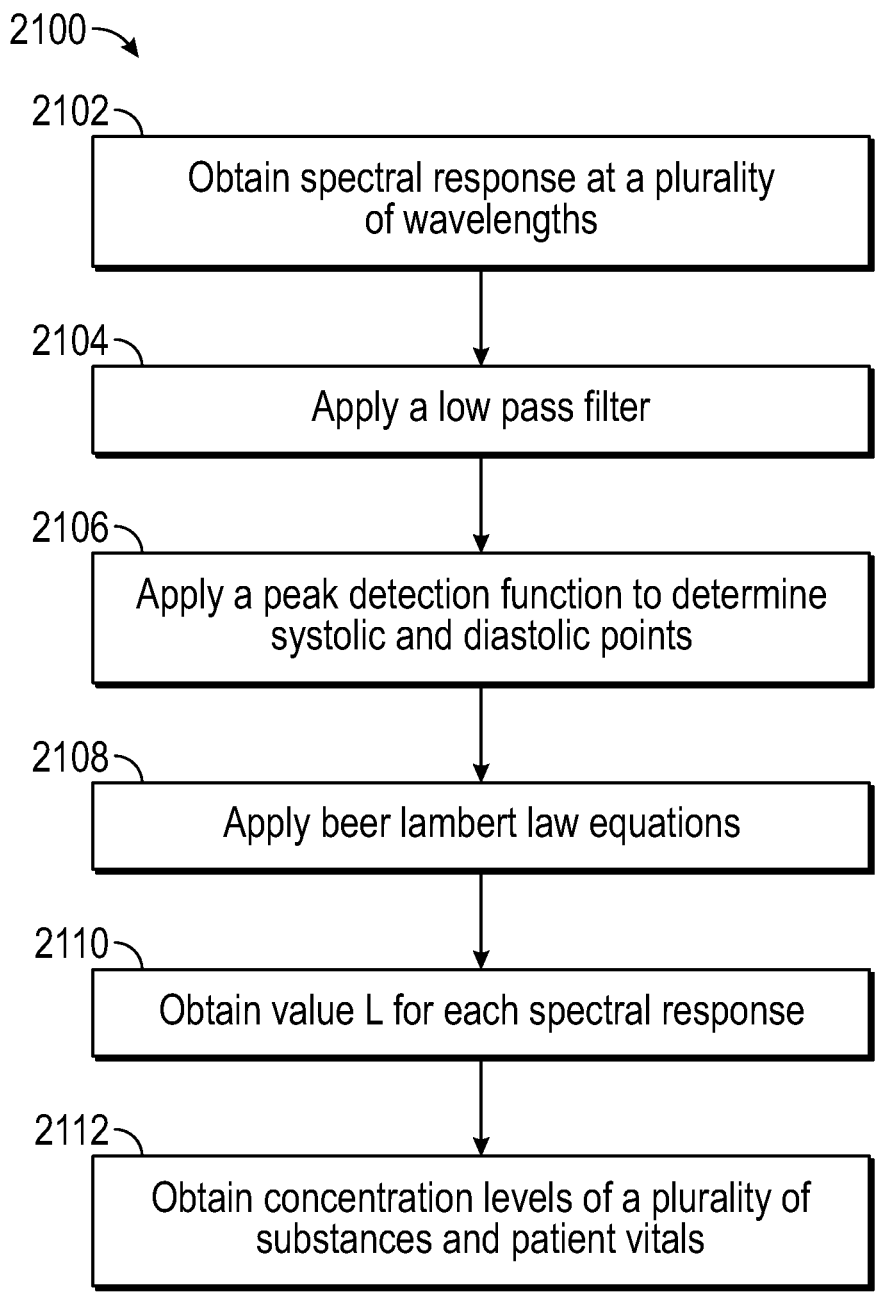
FIG. 21 illustrates a logical flow diagram of an embodiment of a method of the biosensor.

FIG. 21 illustrates a logical flow diagram of an embodiment of a method 2100 of the biosensor 150. In one aspect, the biosensor 150 emits and detects light at a plurality of predetermined frequencies or wavelengths, such as approximately 940 nm, 660 nm, 390 nm, 592 nm, and 468 nm. The light is pulsed for a predetermined period of time (such as 100 usec or 200 Hz) sequentially at each predetermined wavelength. In another aspect, light may be pulsed in a wavelength range of 1 nm to 50 nm around each of the predetermined wavelengths. Then, the spectral responses are obtained for the plurality of wavelengths at 2102. The spectral response may be measured over a predetermined period (such as 300 usec.). This measurement process is repeated sequentially pulsing the light and obtaining spectral measurements over a desired measurement period, e.g. from 1-2 seconds to 1-2 minutes or 2-3 hours or continuously over days or weeks. Because the human pulse is typically on the order of magnitude of one 1 HZ, typically the time differences between the systolic and diastolic points are on the order of magnitude of milliseconds or tens of milliseconds or hundreds of milliseconds. Thus, spectral response measurements may be obtained at a frequency of around 10-100 Hz over the desired measurement period.

A low pass filter (such as a 5 Hz low pass filter) is applied to the spectral response signal at 2104. The relative contributions of the AC and DC components are obtained $I_{AC+DC}$ and $I_{AC}$. A peak detection algorithm is applied to determine the systolic and diastolic points at 2106. Beer Lambert equations are applied as described below at 2108. For example, the $L_\lambda$ values are then calculated for one or more of the wavelengths λ, wherein the $L_\lambda$ values for a wavelength equals:

$$L_\lambda = \text{Log}10\left(\frac{IAC + DC}{IDC}\right)$$

wherein $I_{AC+DC}$ is the intensity of the detected light with AC and DC components and $I_{DC}$ is the intensity of the detected light with the AC filtered by the low pass filter at 2110. The value $L_\lambda$ isolates the spectral response due to pulsating arterial blood flow, e.g. the AC component of the spectral response.

A ratio R of the $L_\lambda$ values at two wavelengths may then be determined. For example, $$\text{Ratio } R = \frac{L\lambda 1}{L\lambda 2}$$

The $L_\lambda$ values and Ratio R may be determined for one or more of the predetermined measurement periods over a desired time period, e.g. from 1-2 seconds to 1-2 minutes or 2-3 hours or continuously over days or weeks to monitor the values. The $L_\lambda$ values and Ratio R may be used to determine concentration levels of one or more substances in the arterial blood flow at 2112 as well as patient vitals, such as oxygen saturation $SpO_2$, heart rate, respiration rate, etc.

Embodiment—Determination of Indicators or
Concentration Levels of One or More Substances In one aspect, based on unexpected results from clinical trials, it was determined that a ratio $R_{390,940}$ obtained at approximately $L_{\lambda 1}$=390 nm and $L_{\lambda 2}$=940 is useful as a predictor or indicator of diabetic risk or diabetes. For example, during experimental clinical trials, spectral responses were obtained during predetermined measurement periods over a 1-2 minute time period at 390 nm and 940 nm. An $R_{390,940}$ value was obtained based on the spectral responses measured during a plurality of the predetermined measurement periods over the 1-2 minute time period. From the unexpected results of the clinical trials, an average or mean $R_{390,940}$ value of less than 1 (e.g., approximately 0.5) indicated that a person has diabetes or early onset of diabetes. An average or mean $R_{390,940}$ value of 2 or above indicated that a person has a lower risk of a diabetes diagnosis. An average or mean $R_{390,940}$ value in the 5-6 range indicated no current risk of diabetes. The $R_{390,940}$ value determined using $L_{\lambda 1}$=390 nm and $L_{\lambda 2=940}$ was thus an indicator of diabetic risk and diabetes. Thus, based on the clinical trials, a non-invasive, quick 1-2 minute test produced an indicator of diabetes or diabetic risk in a person.

In particular, in unexpected results, it is believed that nitric oxide NO levels in the arterial blood flow is being measured at least in part by the biosensor 150 at λ1=390 nm. Since NO is partly in a gaseous form in blood vessels (prior to adhesion to hemoglobin), the total NO concentration levels of in vitro blood samples, e.g. from a finger prick, are not detected as the gas dissipates. Thus, the biosensor 150 measurements to determine the $L_{390\ nm}$ values are the first time NO concentration levels in arterial blood flow have been measured directly in vivo. In clinical trials performed as described further herein, in unexpected results, it seems that the NO levels are an indication of insulin response in the blood as well as concentration levels of insulin and/or glucose levels in the blood. The $L_{\lambda 1=390\ nm}$ and R value obtained from $L_{\lambda 1=390\ nm}$ are thus an indicator of blood glucose levels, insulin response and diabetic risk as well as vascular health. These unexpected results have advantages in early detection of diabetic risk and easier, non-invasive monitoring of insulin resistance and glucose levels as well as vascular health and other conditions. These results are discussed in more detail herein with illustrative experimental data.

The biosensor 150 may also function as a pulse oximeter using similar principles under Beer-lambert law to determine pulse and oxygen saturation levels in pulsating arterial flow. For example, a first wavelength at approximately 940 nm and a second wavelength at approximately 660 nm may be used to determine oxygen saturation levels.

The biosensor 150 may also be used to determine alcohol levels in the blood using wavelengths at approximately 390 nm and/or 468 nm. In another embodiment, an $R_{468,940}$ value for at least $L_{468\ nm}/L_{940\ nm}$ may be used as a liver enzyme indicator, e.g. P450 enzyme indicator. In another embodiment, an $R_{592,940}$ value for at least $L_{592\ nm}/L_{940\ nm}$ may be used as a digestive indicator to measure digestive responses, such as phase 1 and phase 2 digestive stages. The biosensor 150 may also detect other types of electrolytes or analytes, such as sodium and potassium, using similar PPG techniques. In another aspect, the biosensor 150 may detect which blood cell levels in arterial blood flow using similar PPG techniques.

In another aspect, abnormal cells or proteins or compounds that are present or have higher concentrations in the blood with persons having cancer, may be detected using similar PPG techniques described herein at one or more other wavelengths. Thus, cancer risk may then be obtained through non-invasive testing by the biosensor 150.

Since the biosensor 150 may operate in multiple frequencies, various health monitoring tests may be performed concurrently and continuously. These tests may be performed throughout a hospital stay or may be non-invasively and quickly and easily obtained using the biosensor 150 in a physician's office or other clinical setting or at home. These and other aspects of the biosensor 150 are described in more detail herein with clinical trial results.

Figure 22:
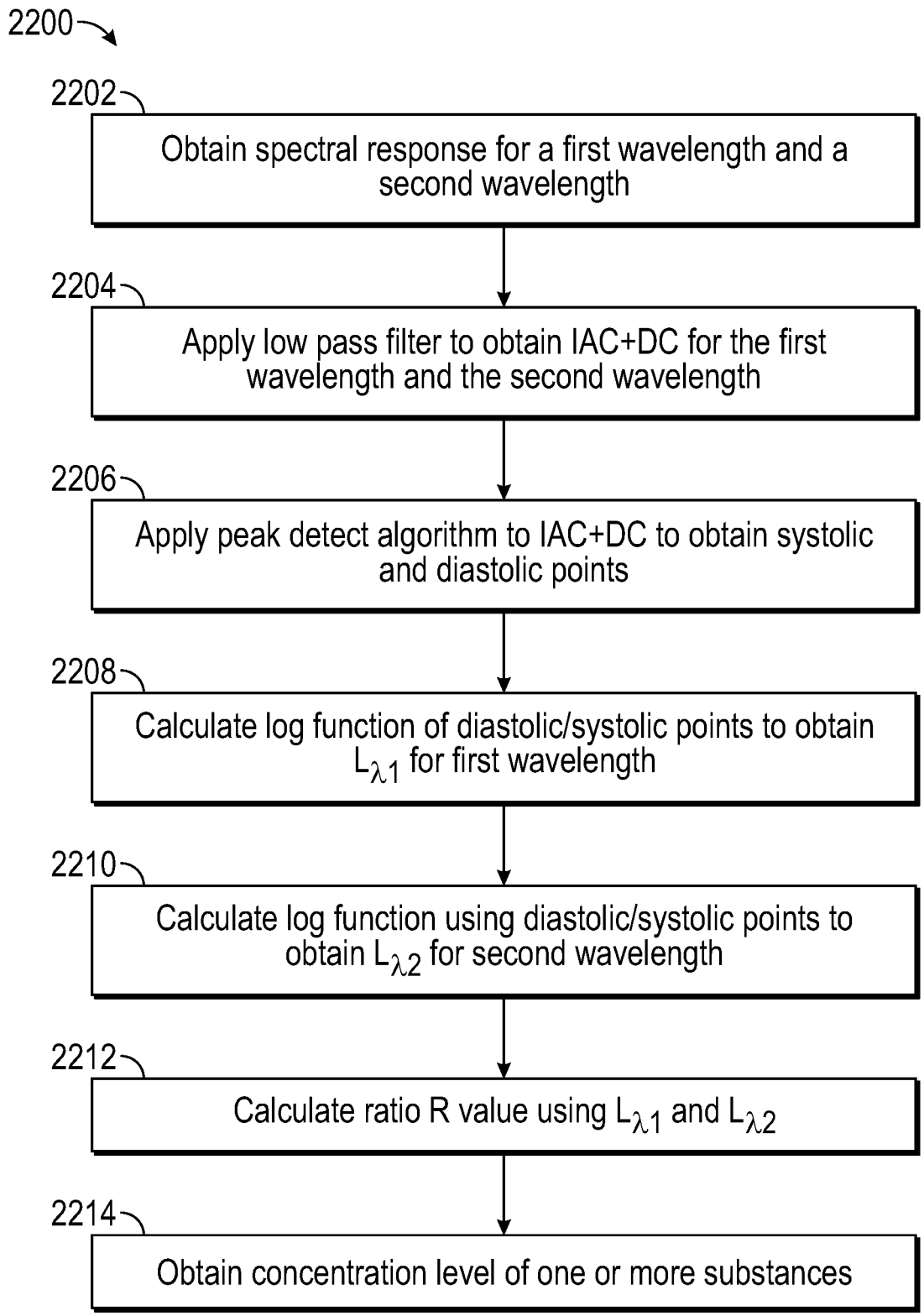
FIG. 22 illustrates a logical flow diagram of an embodiment of a method of determining concentration levels of one or more substances in more detail.

FIG. 22 illustrates a logical flow diagram of an embodiment of a method 2200 of determining concentration levels of one or more substances in more detail. The biosensor 150 obtains a first spectral response signal including a first wavelength and a second response signal including a second wavelength at 2202. In general, the first wavelength is selected that has a high absorption coefficient for the targeted substance while the second wavelength is selected that has a low absorption coefficient for the targeted substance. Thus, it is generally desired that the spectral response for the first predetermined wavelength have a higher intensity level than the spectral response for the second predetermined wavelength.

Each of the spectral response signals includes AC and DC components $I_{AC+DC}$. A low pass filter is applied to the spectral response signals $I_{AC+DC}$ to isolate the DC component of the first and second spectral response signals $I_{DC}$ at 2204. The AC fluctuation is due to the pulsatile expansion of the arteriolar bed due to the volume increase in arterial blood. In order to measure the AC fluctuation, measurements are taken at different times and a peak detection algorithm or other means is used to determine or isolate the diastolic point and the systolic point of the spectral response at 2206. The systolic and diastolic measurements are compared in order to compute the aforementioned R ratio. For example, a logarithmic function may be applied to the ratio of $I_{AC+DC}$ and $I_{DC}$ to obtain an L value for the first wavelength $L_{\lambda 1}$ at 2208 and for the second wavelength $L_{\lambda 2}$ at 2210. The ratio R of the $L_\lambda$ values may then be calculated at 2212. The L values and Ratio R may be used to determine concentration levels of one or more substances in the arterial blood flow at 2214.

In one aspect, the biosensor 150 may include a broad spectrum light source 1020, such as a white light to infrared (IR) or near IR LED 1022, that emits light with wavelengths from e.g. 350 nm to 2500 nm. Broad spectrum light sources with different ranges may be implemented. In an aspect, a broad spectrum light source with a range across 100 nm wavelengths to 2000 nm range of wavelengths in the visible, IR and/or UV frequencies. For example, a broadband tungsten light source for spectroscopy may be used. The spectral response of the reflected light is then measured across the wavelengths in the broad spectrum, e.g. from 350 nm to 2500 nm, concurrently. In an aspect, a charge coupled device (CCD) spectrometer 1030 may be configured to measure the spectral response of the detected light over the broad spectrum.

The spectral response of the reflected light is analyzed for a plurality of wavelengths, e.g. at 10 nm to 15 nm to 20 nm, incremental wavelengths across the wavelengths from 10 nm to 2500 nm. For example, the processing described with respect to FIG. 21 is performed at the plurality of wavelengths. In one aspect, the L values are calculated at incremental wavelengths, such as at nm or 1.5 nm or 2 nm incremental wavelengths. This process may be used to determine one or more wavelengths or ranges of wavelengths useful in detection for one or more substances in the arterial blood flow. For example, a spectral response around a wavelength of 500 nm may have a higher intensity. Trials may then be conducted to determine the one or more substances in the blood that generates this spectral response. In another embodiment, a known substance may be present in the blood and the spectral response across the broad spectrum is then analyzed to determine a pattern or correlation of intensities of wavelengths in the spectral response to the known substance. For example, a pattern of intensities of wavelengths across a range of wavelengths may indicate the presence of a substance. The intensities of the wavelengths may then be analyzed to determine concentration levels of the substance as described in more detail herein.

In another embodiment, the spectral response is analyzed at a set of predetermined wavelengths (or a range of 1 nm to 50 nm including each predetermined wavelength). The L values are calculated for the set of predetermined wavelengths using the analyzed spectral responses. The concentration levels of one or more substances may then be determined based on absorption coefficients for the one or more substances at each of the predetermined wavelengths. The concentration levels of a plurality of substances may be determined using the spectral response of a plurality of frequencies at 2214. The biosensor 150 may thus be used to detect a plurality of substances based on data obtained during a single measurement period. The biosensor 150 may thus perform a blood panel analysis based on in vivo arterial blood flow in a relatively short measurement period of 1-5 minutes. The blood panel analysis may be performed in a physician's office to determine results of the test while the patient is in the office. The biosensor 150 may thus provide blood panel analysis results in a 1-5 minute measurement period without a need for blood samples and lab tests that may take hours or days or weeks to obtain.

Figure 23A:
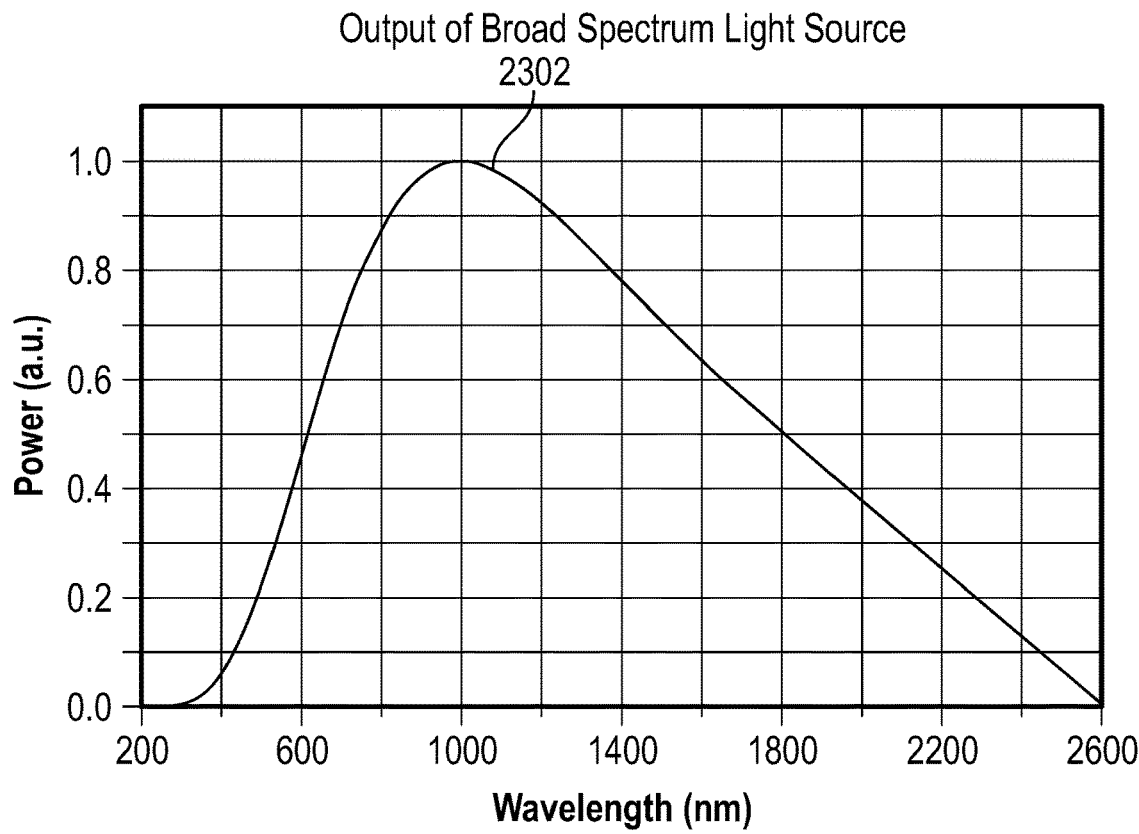
FIG. 23A illustrates a graph of an embodiment of an output of a broad spectrum light source.

FIG. 23A illustrates a graph of an embodiment of an output of a broad spectrum light source. The relative light intensity or power output of the broad spectrum light source is shown versus wavelength of the output light $I_O$. The light intensity or power of the output light extends from wavelengths of approximately 350 nm to approximately 2500 nm. A broad spectrum light source emits light with power across the wavelengths from 350 nm to 2500 nm. Broad spectrum light sources with different ranges may be implemented. In an aspect, a broad spectrum light source with a range across 100 nm wavelengths to 2000 nm range of wavelengths in the visible, IR and/or UV frequencies.

Figure 23B:
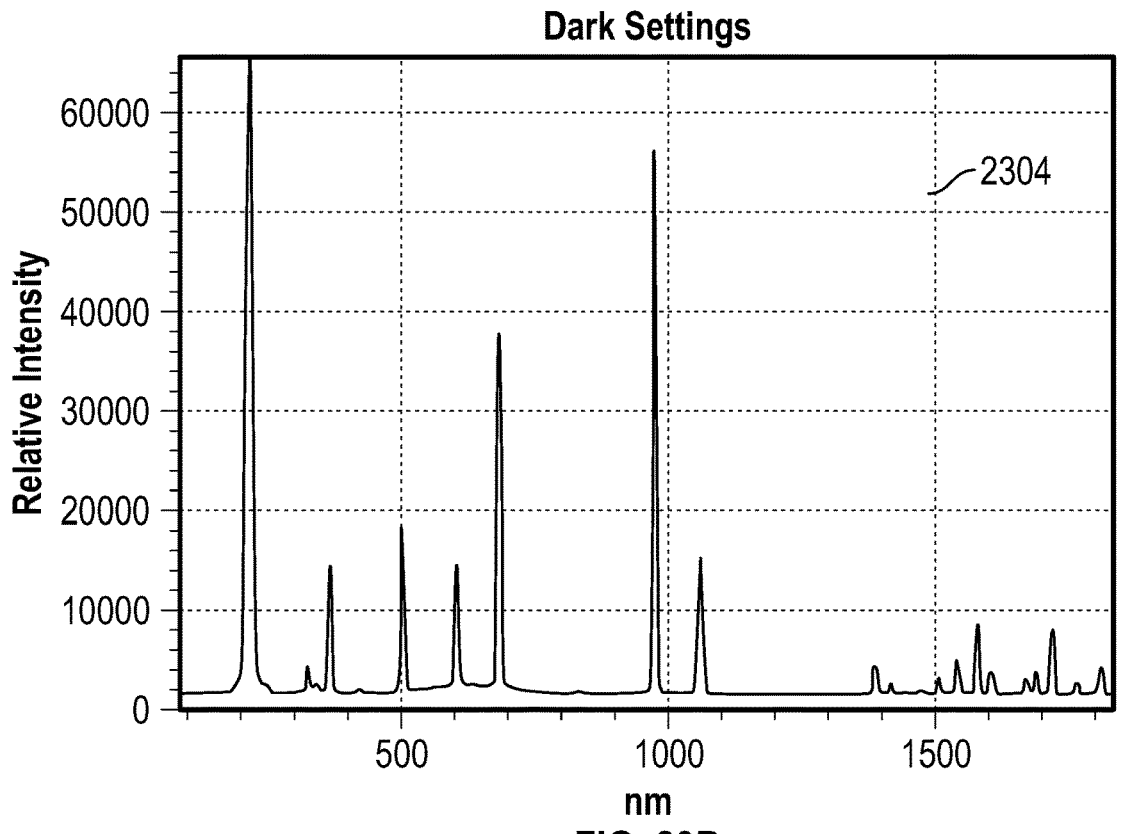
FIG. 23B illustrates a graph with an embodiment of an exemplary spectral response of detected light across a broad spectrum.

FIG. 23B illustrates a graph with an embodiment of an exemplary spectral response of detected light 2304 across a broad spectrum, e.g. from approximately 10 nm to 2000 nm. In one aspect, the spectral response of the detected light 2304 may be analyzed at a plurality of wavelengths, e.g. at a set of predetermined wavelengths or at incremental wavelengths. In another aspect, the spectral response of wavelengths with a detected intensity or power exceeding a predetermined threshold may be analyzed. For example, in the graph shown in FIG. 23B, the spectral response at wavelengths of 200 nm, 680 nm and 990 nm (and ranges of +/−20 to 50 nm around these wavelengths) exceeding a relative intensity threshold of 20000 may be analyzed.

Figure 24:
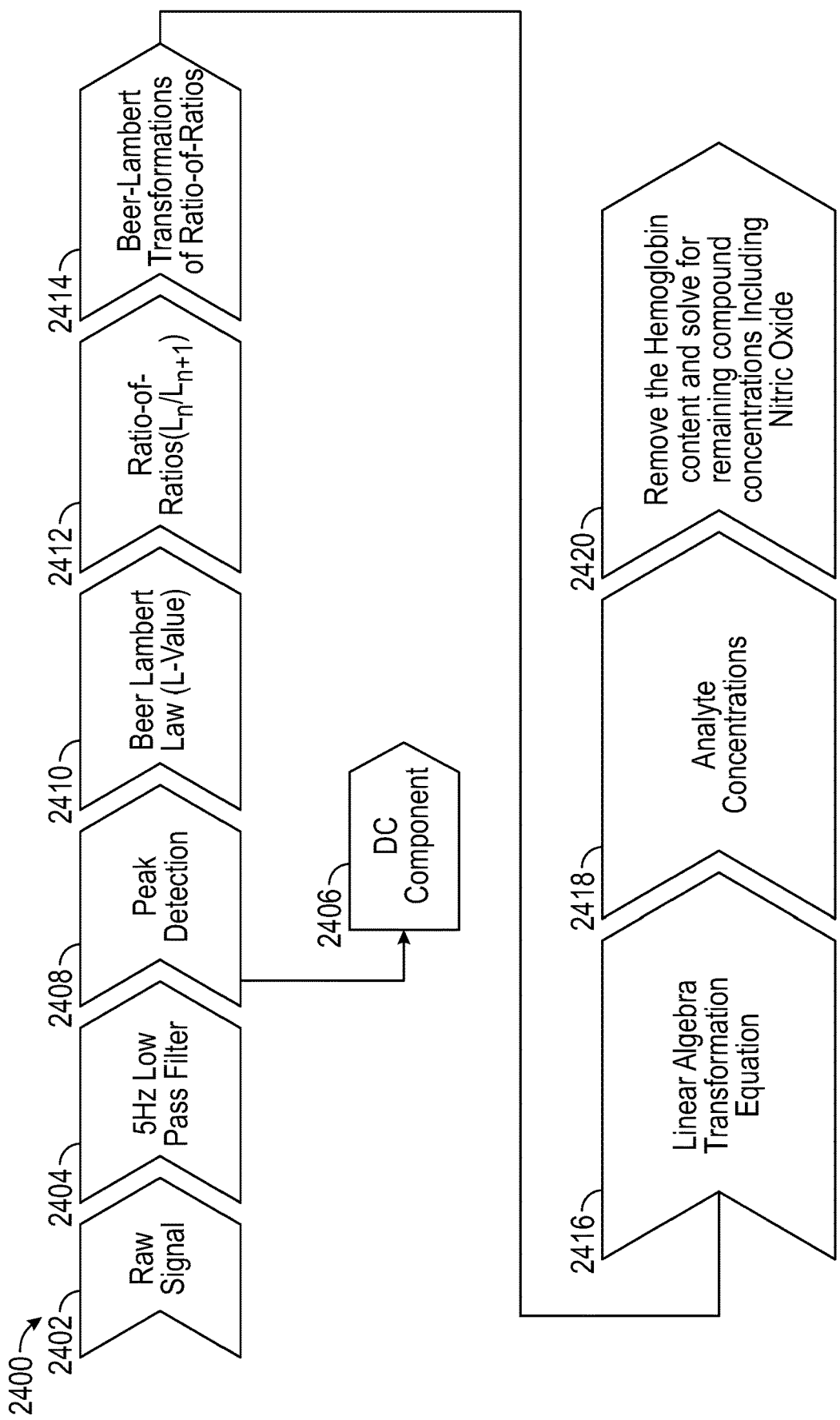
FIG. 24 illustrates a schematic block diagram of an embodiment of a method for determining concentration levels or indicators of substances in pulsating blood flow in more detail.

FIG. 24 illustrates a schematic block diagram of an embodiment of a method 2400 for determining concentration levels or indicators of substances in pulsating blood flow in more detail. The biosensor 150 obtains a spectral response signal at a first wavelength and at a second wavelength at 2402. The spectral response signal includes AC and DC components IAC+DC. A low pass filter is applied to the spectral response signal IAC+DC to isolate the DC component 2406 of the spectral response signal at each wavelength at 2404. The AC fluctuation is due to the pulsatile expansion of the arteriolar bed due to the volume increase in arterial blood. In order to measure the AC fluctuation, measurements are taken at different times and a peak detection algorithm or other means is used to determine the diastolic point and the systolic point of the spectral response at 2408. The systolic and diastolic measurements are compared in order to compute the L values using Beer-Lambert equations at 2410. For example, a logarithmic function may be applied to the ratio of IAC+DC and $I_{DC}$ to obtain an L value for the first wavelength $L_{\lambda 1}$ and for the second wavelength $L_{\lambda 2}$. The ratio R of the first wavelength $L_{\lambda 1}$ and for the second wavelength $L_{\lambda 2}$ may then be calculated at 2412. Beer-Lambert principles are applied to the ratios R at 2414. For example, when multiple frequencies are used to determine a concentration level of one or more substances, the linear function described herein are applied at 2416, and the one or more concentration levels of the substances or analytes are determined at 2418.

In an embodiment, a substances or analyte may be attached in the blood stream to one or more hemoglobin compounds. The concentration level of the hemoglobin compounds may then need to be subtracted from the concentration level of the substance to isolate the concentration level of the substance from the hemoglobin compounds. For example, nitric oxide (NO) is found in the blood stream in a gaseous form and also attached to hemoglobin compounds. Thus, the measurements at $L_{390\,nm}$ to detect nitric oxide may include a concentration level of the hemoglobin compounds as well as nitric oxide.

The hemoglobin compound concentration levels may be determined and subtracted to isolate the concentration level of the substance at 2420. The hemoglobin compounds include, e.g., Oxyhemoglobin [HbO2], Carboxyhemoglobin [HbCO], Methemoglobin [HbMet], and reduced hemoglobin fractions [RHb]. The biosensor 150 may control the PPG circuit 300 to detect the total concentration of the hemoglobin compounds using a center frequency of 660 nm and a range of 1 nm to 50 nm. A method for determining the relative concentration or composition of different kinds of hemoglobin contained in blood is described in more detail in U.S. Pat. No. 6,104,938 issued on Aug. 15, 2000, which is hereby incorporated by reference herein.

Various unexpected results were determined from clinical trials using the biosensor 150. In one aspect, based on the clinical trials, an R value obtained from the ratio $L_{\lambda 1=390\,nm}$ and $L_{\lambda 2=940\,nm}$ was found to be a predictor or indicator of diabetic risk or diabetes as described in more detail herein. In another aspect, based on the clinical trials, the R value obtained from the ratio of $L_{468\,nm}/L_{940\,nm}$ was identified as an indicator of the liver enzyme marker P450. In another aspect, based on the clinical trials, the R value obtained from the ratio of $L_{592\,nm}/L_{940\,nm}$ was identified as an indicator of digestion phases, such as phase 1 and phase 2, in the arterial blood flow. In another aspect, the R value from the ratio of $L_{660\,nm}/L_{940\,nm}$ was found to be an indicator of oxygen saturation levels $SpO_2$ in the arterial blood flow. In another aspect, it was determined that the biosensor 150 may determine alcohol levels in the blood using spectral responses for wavelengths at 390 and/or 468 nm. In general, the second wavelength of 940 nm is selected because it has a low absorption coefficient for the targeted substances described herein. Thus, another wavelength other than 940 nm with a low absorption coefficient for the targeted substances (e.g. at least less than 25% of the absorption coefficient of the targeted substance for the first wavelength) may be used instead. For example, the second wavelength of 940 nm may be replaced with 860 nm that has a low absorption coefficient for the targeted substances. In another aspect, the second wavelength of 940 nm may be replaced with other wavelengths, e.g. in the IR range, that have a low absorption coefficient for the targeted substances. In general, it is desired that the spectral response for the first predetermined wavelength have a higher intensity level than the spectral response for the second predetermined wavelength.

In another aspect, it was determined that other proteins or compounds, such as those present or with higher concentrations in the blood with persons having cancer, may be detected using similar PPG techniques described herein with biosensor 150 at one or more other wavelengths. Cancer risk may then be determined using non-invasive testing over a short measurement period of 1-10 minutes. Since the biosensor may operate in multiple frequencies, various health monitoring tests may be performed concurrently. For example, the biosensor 150 may measure for diabetic risk, liver enzymes, alcohol levels, cancer risk or presence of other analytes within a same measurement period using PPG techniques.

Figure 25:
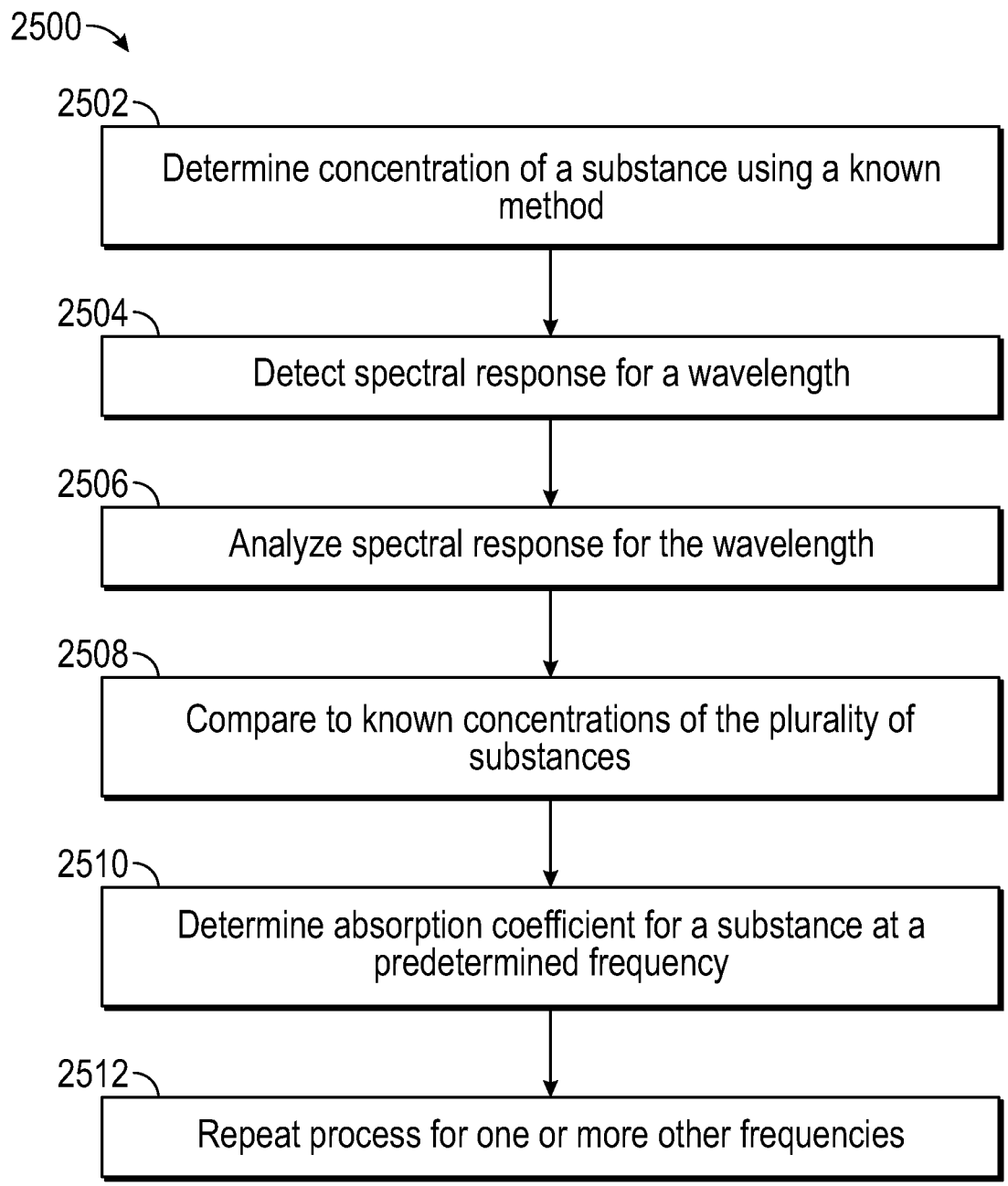
FIG. 25 illustrates a logical flow diagram of an exemplary method to determine an absorption coefficients of a substance at a wavelength λ.

FIG. 25 illustrates a logical flow diagram of an exemplary method 2500 to determine an absorption coefficients of a substance at a wavelength λ. The concentration level of a substance in arterial blood is obtained using a known method at 2502. For example, blood may be extracted at predetermined intervals during a time period and a blood gas analyzer may be used to measure a concentration level of a substance. The biosensor 150 emits light at a wavelength (and in one aspect for a range of 1 nm-50 nm around the wavelength) and detects a spectral response for the wavelength (and in one aspect for a range of 1 nm-50 nm around the wavelength) at 2504. The spectral response for the predetermined wavelength is analyzed at 2506. The intensity of the detected light is determined. The intensity of the detected light is compared to the known concentration level of the substance at 2508. The absorption coefficient for the substance may then be determined using the Beer-Lambert equations described herein at 2510.

The above process may be repeated at one or more other frequencies at 2512. For example, as described herein, the spectral analysis over a range or at multiple frequencies may be analyzed to determine one or more frequencies with a higher intensity or power level in response to a concentration level or presence of the substance. Thus, one or more frequencies may be analyzed and identified for detection of the substance, and the absorption coefficient for the substance determined at the one or more frequencies.

In another embodiment, the concentration level of a substance may be obtained from predetermined values obtained through experimentation. For example, in a calibration phase, a correlation table may be compiled through experimentation that includes light intensity values $I_{1-n}$ at one or more wavelengths $\lambda_{1-n}$ and a corresponding known concentration level for the substance for the light intensity values. In use, the biosensor 150 detects a spectral response and determines the light intensity values $I_{1-n}$ at one or more wavelengths $\lambda_{1-n}$. The biosensor 150 then looks up the detected light intensity values $I_{1-n}$ in the correlation table to determine the concentration level of the substance.

Figure 26:
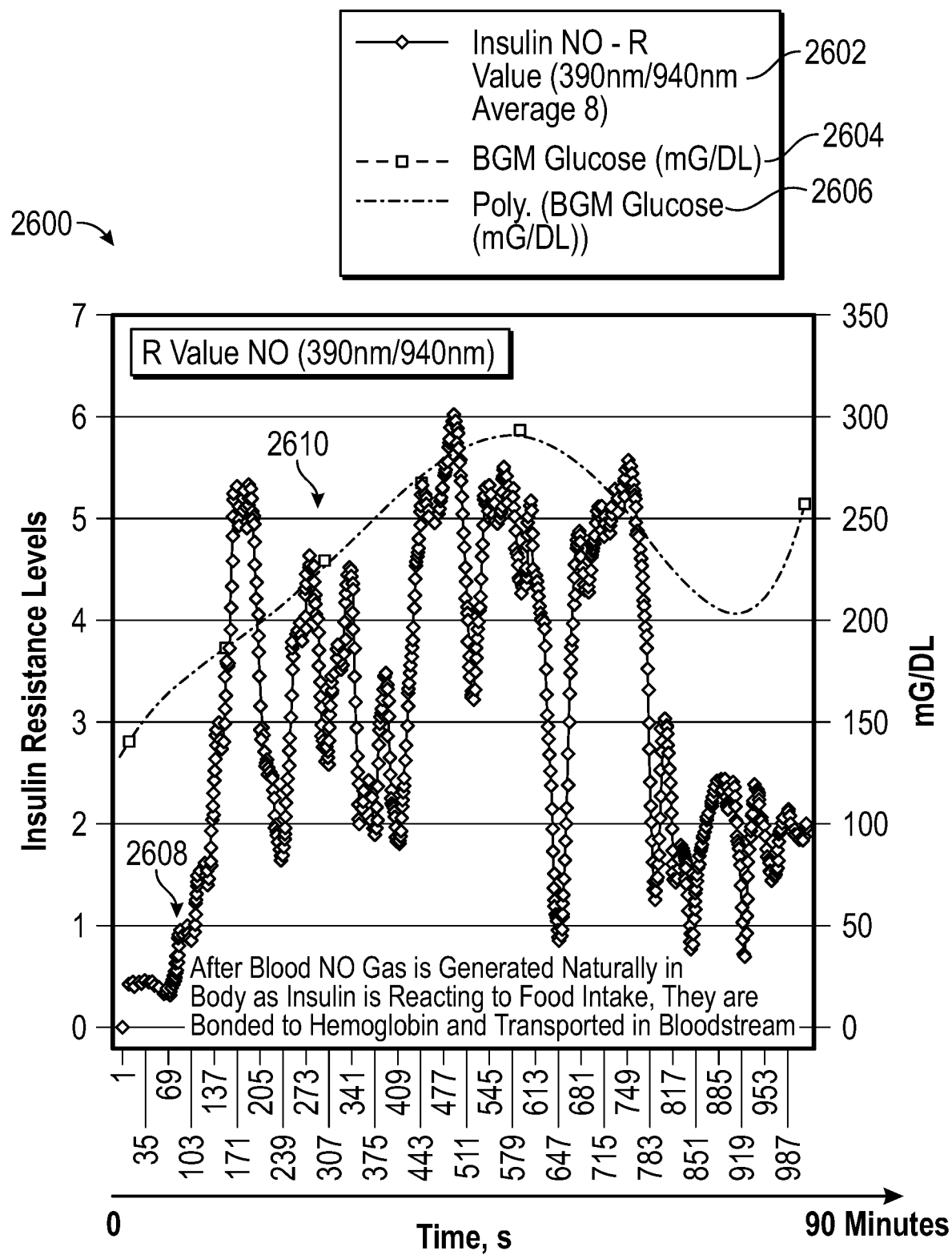
FIG. 26 illustrates a schematic drawing of another exemplary embodiment of results of clinical data obtained using an embodiment of the biosensor from a second patient.

FIG. 26 illustrates a schematic drawing of another exemplary embodiment of results of clinical data 2600 obtained using an embodiment of the biosensor 150 from a second patient. The second patient is a 59 year old male with a known diagnosis of Type 2 diabetes. At predetermined time periods of about 15 minutes, blood glucose level (BGL) was measured using a known method of a blood glucose meter (BGM) using blood from finger pricks. The BGM glucose measurements 2604 are plotted. The plotted measurements were interpolated to generate a polynomial 2606 showing the approximate BGM glucose measurements over time in mG/DL units. The biosensor 150 obtained measurements over the same time period to derive the Ratio R for approximately $L_{390\,nm}/L_{940\,nm}$ 2602, as shown on the graph as well.

In this clinical trial, the base insulin resistance factor measured prior to eating has a low baseline value of about 0.5 indicating a diabetic condition. In unexpected results, the base insulin resistance factor or R value for $L_{390\,nm}/L_{940\,nm}$ of less than 1 (in an R value range of 0-8) thus seems to indicate a diabetic condition from the clinical trial results. After consumption of a high sugar substance, insulin response 2610 is seen after about 7 minutes. The blood glucose levels may be obtained from the R values using the graph 2600 or a similar calibration table that correlates the R value with known BGL measurements for the patient. The calibration table may be generated for a specific patient or may be generated from a sample of a general population. It is determined that the R values should correlate to similar BGL measurements across a general population. Thus, the calibration table may be generated from testing of a sample of a general population.

From the unexpected results of the clinical trials, an R value of less than 1 (in an R value range of 0-8) indicated that a person has diabetes or early onset of diabetes. An R value of 5 (in an R value range of 0-8) or above indicated that a person has no diabetic condition. For example, as shown in graph 2608, the base insulin resistance factor measured using an R value of approximately $L_{390\,nm}/L_{940\,nm}$ has generally an average value greater than 5 in the first patient without a diabetes diagnosis. The base insulin resistance factor measured using an R value of approximately $L_{390\,nm}/L_{940\,nm}$ was generally an average value less than 1 (in an R value range from 0-8) in the other patients with a diabetes diagnosis of either Type 1 or Type II. The base insulin resistance factor measured using an R value in the 1-2 (in an R value range from 0-8) range indicated a high risk of diabetes and need for further testing.

It seems that the $L_{390\,nm}$ is measuring NO levels in the arterial blood flow. As insulin is generated in the body, it reacts with blood vessels to generate NO gas. The NO gas bonds to hemoglobin and is transported in the blood stream. The NO is thus a good indicator of a base insulin resistance factor after fasting and an insulin response after caloric intake.

From the clinical trials, it seems that the NO levels are reflected in the R values obtained from $L_{390\,nm}/L_{940\,nm}$. Based on the clinical trials and R values obtained in the clinical trials, it is determined that a base insulin resistance factor of less than 1 corresponds to an NO concentration level of at least less than 25% of average NO levels. For example, average NO levels are determined by sampling a general population of persons without diabetes or other health conditions affecting NO levels. From the clinical trials, an R value correlating to a base insulin factor of less than 1 indicates that the NO levels are in a range of 25% to 50% less than average NO levels. After fasting, a person with a diabetic condition will have low NO concentration levels that are at least 25% less than average NO levels due to the low level of insulin in the blood. Thus, an NO concentration level of at least less than 25% of normal ranges of NO concentration levels indicates a diabetic condition (e.g., the NO levels corresponding to R value less than 1 in this clinical trial). Thus, a base insulin resistance factor of less than 1 correlates to at least less than 25% of average NO levels of a sample population and indicates a diabetic condition.

Based on the clinical trials and R values obtained in the clinical trials, it is determined that a base insulin resistance factor in the range of 2-8 corresponds to average NO concentration levels. Thus, a base insulin resistance factor (e.g. in the range of 2-8) correlates to an average NO level of a sample population and little to no diabetic risk.

Based on these unexpected results, in one aspect, the biosensor 150 may display or transmit, e.g. to a user device or monitoring station, or otherwise output an indicator of the diabetic risk of a patient based on the R value. For example, the biosensor 150 may output no diabetic risk based on an obtained R value for a patient of 5 or greater. In another aspect, the biosensor 150 may output low diabetic risk based on an obtained R value of 2-5. In another aspect, the biosensor 150 may output high diabetic risk based on an obtained R values of 1-2. In another aspect, the biosensor 150 may output diabetic condition detected based on an R value less than one. In the clinical trials herein, the R value was in a range of 0-8. Other ranges, weights or functions derived using the R value described herein may be implemented that changes the numerical value of the R values described herein or the range of the R values described herein. In general, from the results obtained herein, an R value corresponding to at least the lower 10% of the R value range indicates a diabetic condition, an R value in the lower 10% to 25% of the R value range indicates a high risk of diabetes, an R value in the 25% to 60% range indicates a low risk of diabetes, and an R value greater than 60% indicates no diabetic condition.

The R value of $L_{390\ nm}/L_{940\ nm}$ may be non-invasively and quickly and easily obtained using the biosensor 150 in a physician's office or other clinical setting or at home. In one aspect, the R value may be used to determine whether further testing for diabetes needs to be performed. For example, upon detection of a low R value of less than 1, a clinician may then determine to perform further testing and monitoring, e.g. using glucose ingestion tests over a longer period of time or using the biosensor 150 over a longer period of time or other type of testing.

Embodiment—Blood Alcohol Level Measurements

Figure 27:
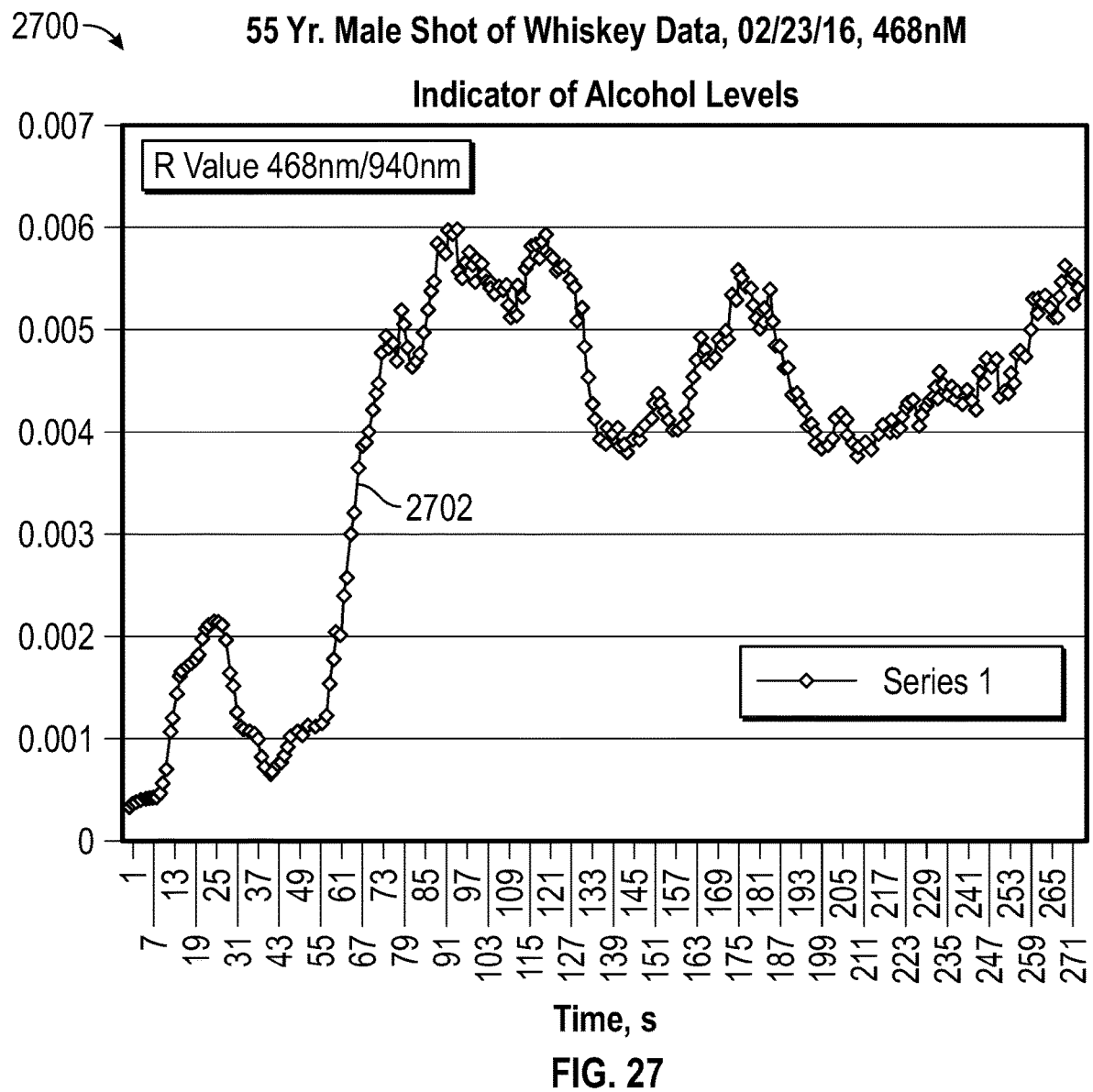
FIG. 27 illustrates a schematic drawing of another exemplary embodiment of results of clinical data obtained using an embodiment of the biosensor from a third patient.

FIG. 27 illustrates a schematic drawing of another exemplary embodiment of results of clinical data 2700 obtained using an embodiment of the biosensor 150 from a third patient. In this trial, the third patient was a 55 year old male that ingested a shot of whiskey at approximately 7 seconds. The biosensor 150 was used to measure an indicator of blood alcohol levels over a measurement period of approximately 271 seconds using a wavelength of approximately 468 nm. The graph illustrates the values obtained for ratio $R=L_{468\ nm}/L_{940\ nm}$ 2702 over the measurement period. The biosensor 150 was able to detect the increase in the blood alcohol levels over the measurement period. The ratio R values 2702 may be correlated with blood alcohol levels using a table or graph that associates the R values 2702 with blood alcohol levels. For example, the table or graph may be obtained through blood alcohol levels measured from blood drawn at preset intervals (such as every 1-5 minutes) during a measurement period (such as 1-5 hours) and interpolating the resulting measurements. The interpolated measurements are then associated with the measured ratio R values 2702 over the same measurement period. In general, the ratio R values 2702 are consistent with an approximate measured blood alcohol level in subsequent clinical trials for a patient. The calibration of measured blood alcohol levels to ratio R values 2702 may thus only be performed once for a patient. In another aspect, the calibration table may be generated using testing of a sample of a general population. It is determined that the R values should correlate to similar BAL measurements across a general population. Thus, the calibration table may be generated from testing of a sample of a general population.

In unexpected results, concentration levels of a liver enzyme called cytochrome P450 Oxidase (P450) that is generated in the presence of alcohol may be measured by the biosensor 150. The spectral response around the wavelength at approximately 468 nm seems to track the concentration levels of the liver enzyme P450. The liver enzyme is generated to react with various substances and may be generated in response to alcohol levels. Thus, the measurement of the spectral response for the wavelength at approximately 468 nm may indicate blood alcohol levels and/or concentration levels of P450.

Embodiment—Digestive Stage and Caloric Intake Measurements

Figure 28:
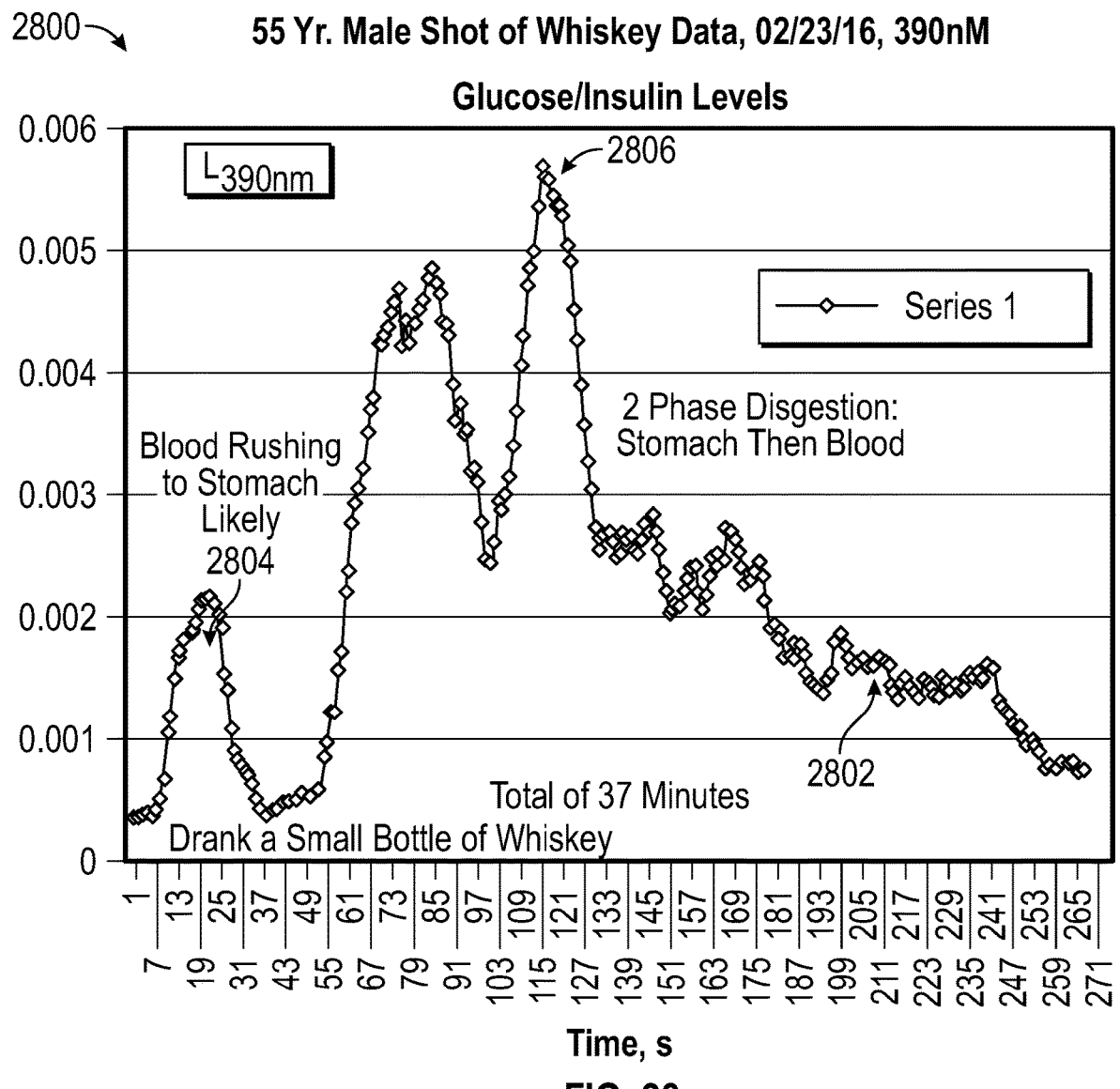
FIG. 28 illustrates a schematic drawing of another exemplary embodiment of results of clinical data obtained using the biosensor from a fourth patient.

FIG. 28 illustrates a schematic drawing of another exemplary embodiment of results of clinical data 2800 obtained using the biosensor 150 from a fourth patient. In this trial, the fourth patient ingested whiskey at approximately 13 seconds. The biosensor 150 was used to measure the digestive stages over a measurement period of approximately 37 minutes using a wavelength of approximately 390 nm to track the blood glucose levels. The graph illustrates the values for $L_{390\ nm}$ 2802 obtained over the measurement period. The biosensor 150 was able to detect the digestive stage 1 2804 and digestive stage 2 2806 based on the obtained values for $L_{390\ nm}$. The first digestive stage 1 2804 is indicated by an initial spike around 20 seconds as blood rushes to the stomach to aid in digestion. The second digestive stage 2 is indicated by a later, more prolonged increase in blood glucose levels between 60 and 180 seconds.

Based on the insulin response and BGL measurements, a calibration of caloric intake may be performed for a patient. For example, known caloric intakes may be correlated with insulin response in phase 1 and phase 2 digestions measured using values for $L_{390\ nm}$ 2802. In another aspect, the calibration table may be generated using testing of a sample of a general population. It is determined that the R values using $L_{390\ nm}$ 2802 and, e.g., $L_{940\ nm}$ should correlate to similar caloric intake measurements across a general population. Thus, the calibration table may be generated from testing of a sample of a general population.

Embodiment—Measurements of Other Substances

Using similar principles described herein, the biosensor 150 may measure concentration levels or indicators of other substances in pulsating blood flow. For example, absorption coefficients for one or more frequencies that have an intensity level responsive to concentration level of substance may be determined. The biosensor 150 may then detect the substance at the determined one or more frequencies as described herein and determine the concentration levels using the Beer-Lambert principles and the absorption coefficients. The L values and R values may be calculated based on the obtained spectral response. In one aspect, the biosensor 150 may detect various electrolyte concentration levels or blood analyte levels, such as bilirubin (using $L_{460\ nm}$) and iron (using $L_{510\ nm}$, $L_{651\ nm}$, $L_{300\ nm}$) and potassium (using $L_{550\ nm}$).

In another aspect, the biosensor 150 may detect sodium chloride NACL (using $L_{450\ nm}$) concentration levels in the arterial blood flow and determine dehydration level. The biosensor 150 may then output a determination of level of dehydration based on the detected NACL concentration levels.

In yet another aspect, the biosensor 150 may be configured to detect proteins or abnormal cells or other elements or compounds associated with cancer. The biosensor 150 may measure concentration levels or indicators of other substances in pulsating blood flow using similar principles described herein.

For example, the value $L_{\lambda 1}$ is determined from a spectral response of a wavelength with a high absorption coefficient for the targeted substance. The value $L_{\lambda 2}$ is determined from a spectral response of the wavelength with a low absorption coefficient for the targeted substance. The ratio $R_{\lambda 1, \lambda 2}$ is determined from the value $L_{\lambda 1}$ and the value $L_{\lambda 2}$. A calibration table may be generated using testing of a sample of a general population that correlates values of the ratio $R_{\lambda 1, \lambda 2}$ to concentration levels of the target substance. Then the concentration level of the targeted substance may be determined using the calibration table and the measured values for the ratio $R_{\lambda 1, \lambda 2}$.

Embodiment—Detection of Types of Cells

The biosensor 150 may detect concentration levels of different types of cells in arterial blood flow. For example, the biosensor 150 may detect the various types of white blood cells based on the spectral response of the wavelengths, e.g. using one or more wavelengths shown in Table 1 below.

TABLE 1

Detection of White Blood Cells

| White Blood Cell Type | Diameter | Color | Spectral Absorption Wavelengths |
|---|---|---|---|
| Neutrophil | 10-12 um | Pink-Red, Blue, White | Red-660 nm Blue-470 nm Green-580 nm |
| Eosinophil | 10-12 um | Pink Orange | 660 nm, 470 nm, 580 nm 600 nm |
| Basophil | 12-15 um | Blue | 470 nm |
| Lymphocyte | 7-15 um | | 633 nm |
| Monocyte | 15-30 um | | 580 nm |

The biosensor 150 may detect a color or color change of the blood due to an increase or decrease in white blood cells using one or more wavelengths described in Table 1. Based on the detected color or color change of the blood, the biosensor 150 may output an alert to a presence of an infection. For example, the biosensor 150 monitors the color of the blood. When it detects a color change indicating an increase in white blood cells, the biosensor determines whether this color change meets a predetermined threshold indicating a presence of an infection. The predetermined threshold may include a color scale and/or length of time of color change. When the color change reaches the predetermined threshold, the biosensor 150 transmits or displays an alert to indicate a presence of an infection.

In another aspect, the biosensor 150 may detect white blood cells from spectral responses at one or more wavelengths. Due to the larger size of the white blood cells from red blood cells, the presence of white blood cells in the blood affects the spectral width and shape of a spectral response.

Figure 29:
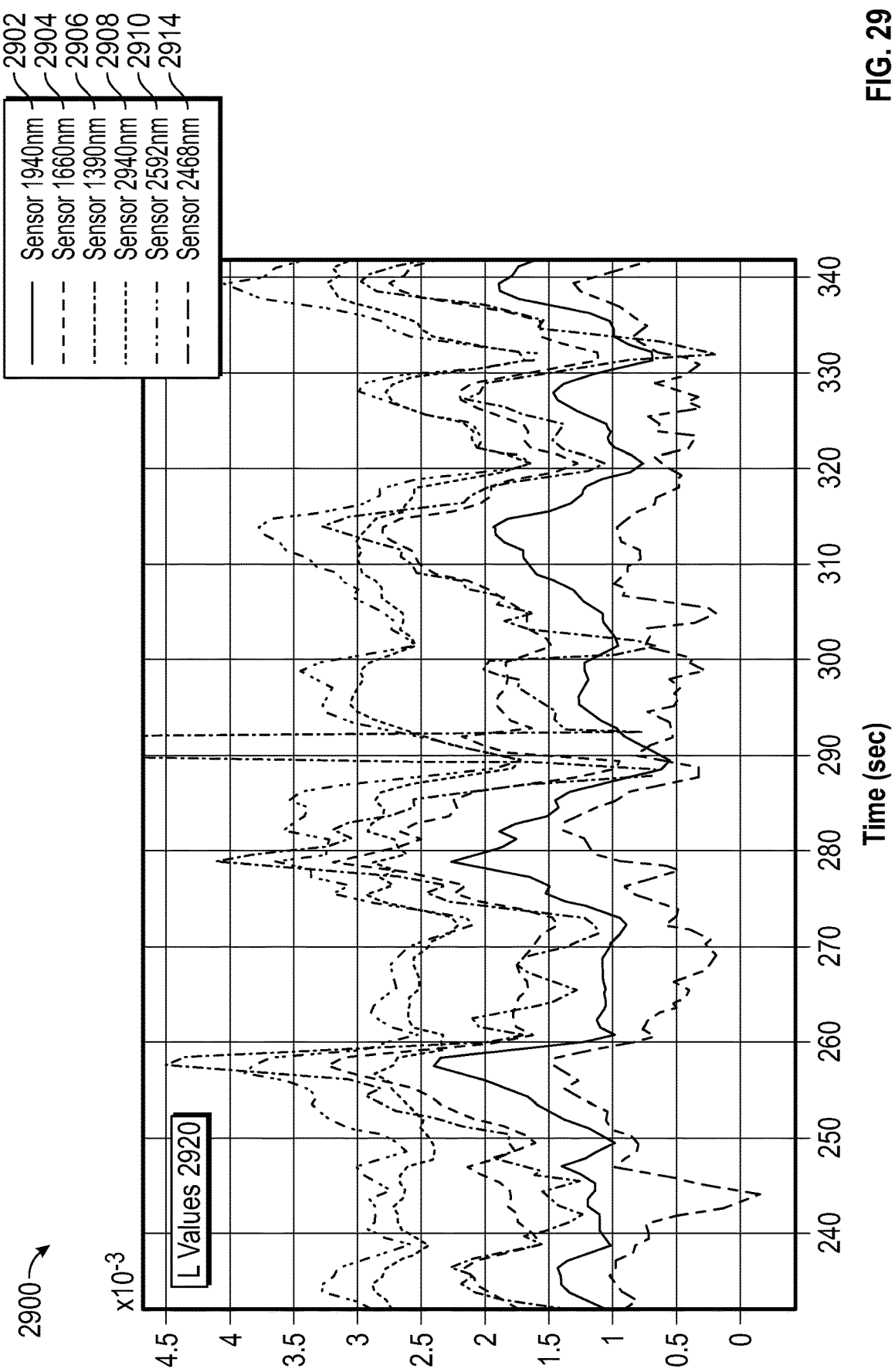
FIG. 29 illustrates an exemplary graph of spectral responses of a plurality of wavelengths from clinical data using the biosensor.

FIG. 29 illustrates an exemplary graph 2900 of spectral responses of a plurality of wavelengths from clinical data using the biosensor 150. In this embodiment, the spectral response of a plurality of wavelengths was measured using the biosensor 150 over a measurement period of almost 600 seconds or approximately 10 minutes. The graph 2900 illustrates the L values calculated from the spectral response for a first wavelength 2902 of approximately 940 nm, the spectral response for a second wavelength 2904 of approximately 660 nm and the spectral response for a third wavelength 2906 of approximately 390 nm obtained from a first biosensor 150 measuring reflected light from a first fingertip of a patient. The graph further illustrates the spectral response for a fourth wavelength 2910 of approximately 592 nm and a fifth wavelength 2914 of approximately 468 nm and the spectral response 1408 again at 940 nm obtained from a second biosensor measuring reflected light from a second fingertip of a patient. The spectral responses are temporally aligned using the systolic and diastolic points. Though two biosensors were used to obtain the spectral responses in this clinical trial, a single biosensor 150 may also be configured to obtain the spectral responses of the plurality of wavelengths.

Due to the size of white blood cells, the presence of the white blood cells in the blood affects the spectral width and shape of a spectral response at one or more wavelengths. In one aspect, from L values 2920 shown for the spectral response at 660 nm 2904, the width and shape of the spectral response is affected by the presence of white blood cells. For example, the width and shape of $L_{660\ nm}$ between 250 and 270 seconds has a different shape and width of $L_{660\ nm}$ between 300 and 320 seconds in the graph 2900. The differences in the width and shape of the spectral response may be used to determine a concentration level of white blood cells or change in concentration level of white blood cells in the blood.

In another example, the spectral responses may be used to determine a presence of infection from a level of neutrophils or neutrophilic white blood cells in arterial blood flow. The concentration of neutrophils increases in the presence of an infection. The neutrophil particles have a different color and size from red blood cells. The biosensor 150 may determine an increase in concentration of neutrophil cells in response to a change in color of the blood. In addition, the biosensor 150 may determine an increase in concentration of neutrophil cells in response to a change in a pattern of the spectral response (L value and/or R value) due to a change in size of particles in the blood. The biosensor 150 may use a combination of both a change in color and change in a pattern of the spectral response (L value and/or R value) to determine a concentration of neutrophils.

Figure 30:
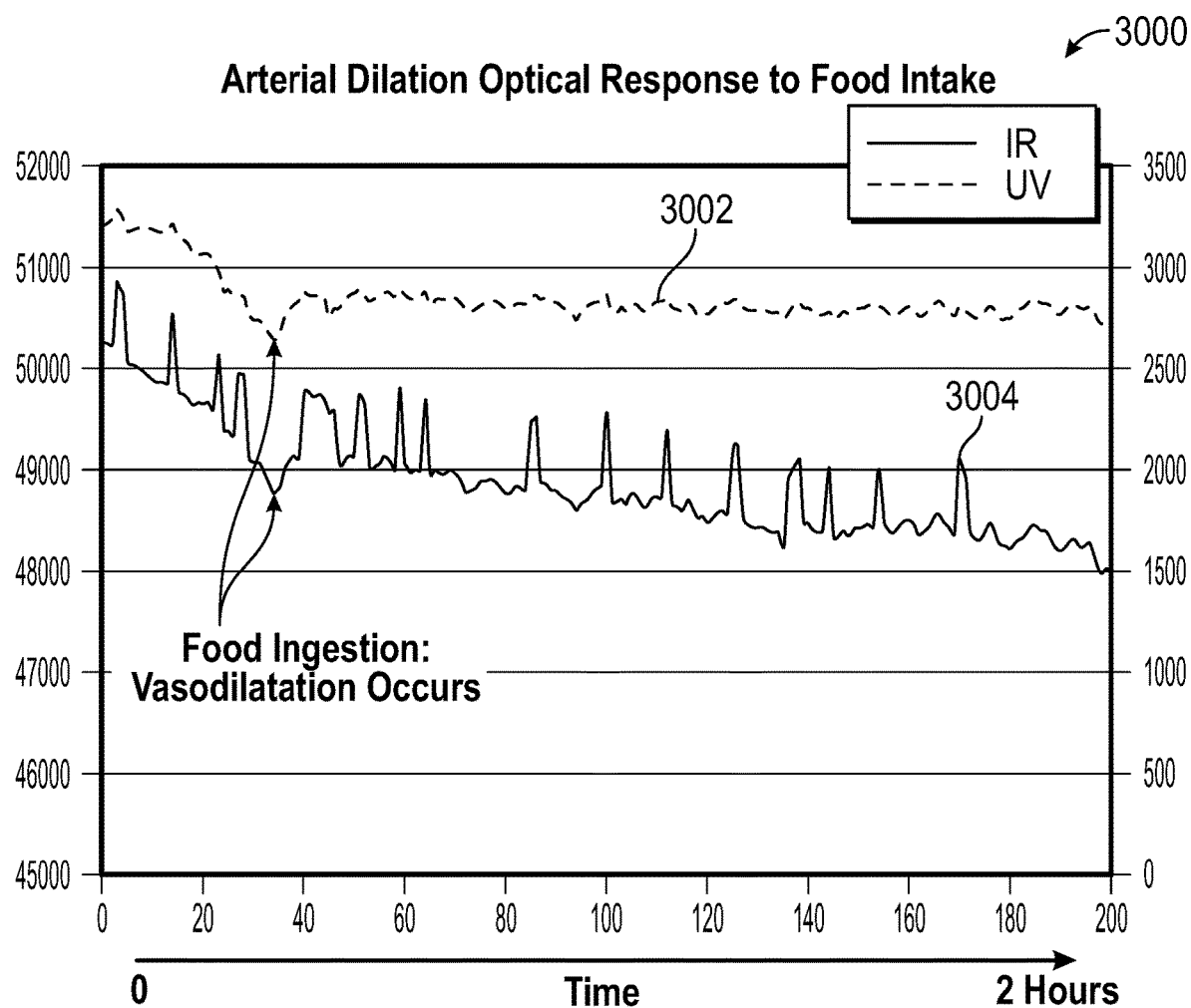
FIG. 30 illustrates an exemplary graph of spectral responses of a plurality of wavelengths from clinical data using the biosensor.

FIG. 30 illustrates an exemplary graph 3000 of spectral responses of a plurality of wavelengths from clinical data using the biosensor 150. The graph 3000 illustrates use of the spectral response to determine a level of arterial dilation or vasodilation. Vasodilation refers to the widening of blood vessels. It results from relaxation of smooth muscle cells within the vessel walls. A substance that causes dilation of blood vessels by promoting the relaxation of vascular smooth muscle are referred to as vasodilators. Chemical vasodilators include hydralazine, nitroglycerin, nitroprusside, nesiritide, and trimethaphan.

The spectral response in graph 3000 illustrates an increase in intensity of the spectral response at approximately 35 minutes in arterial blood flow. The spectral responses are from wavelengths in the infrared (IR) range and in the ultraviolet (UV) range from clinical data using the biosensor 150. The spectral responses may be used to obtain a level of dilation of the arteries of a patient. For example, upon ingestion of food, blood gases such as NO are released and cause dilation of the vessels. The infrared (IR) spectral measurement increases in intensity as shown in graph 3000 at about 35 minutes due to increased blood flow through the dilated arteries. The increase in a spectral response of IR light 3004 may be measured and mapped to a level of dilation of the arteries. A spectral response of UV light 3002 may also be measured and mapped to a level of dilation as seen in the graph 3000 at about 35 minutes. The level of vasodilation may thus be measured using the spectral responses of light in the IR or UV range.

Figure 31:
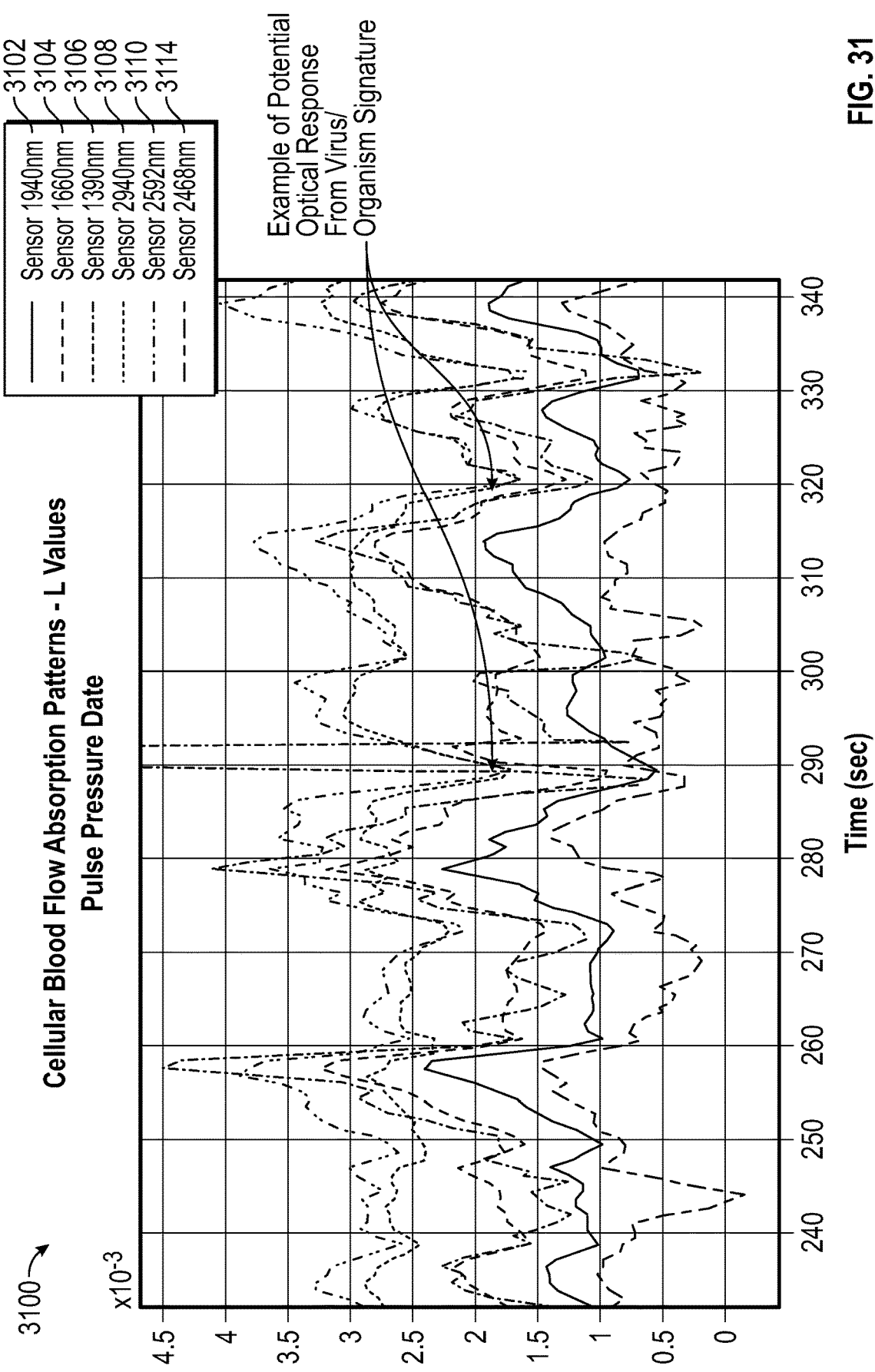
FIG. 31 illustrates an exemplary graph of spectral responses of a plurality of wavelengths from clinical data using the biosensor.

FIG. 31 illustrates an exemplary graph 3100 of spectral responses of a plurality of wavelengths from clinical data using the biosensor 150. The spectral responses may be used to determine the presence and concentration of various organisms in arterial blood flow. Due to the size and shape of various organisms, the presence of the organisms in the blood affects the spectral width and shape of a spectral response at one or more wavelengths. In one aspect, from L values shown for the spectral response at 660 nm 3104, the width and shape of the spectral response is affected by the presence of white blood cells. For example, the width and shape of $L_{660\ nm}$ between 290 and 320 seconds has a different shape and width. The differences in the width and shape of the spectral response may be used to determine a presence of an organism, a concentration level of an organism or change in concentration level of an organism in the arterial blood flow.

For example, a test is performed on blood with a known concentration of a certain virus. The spectral responses of a plurality of wavelengths of arterial blood flow are detected with the PPG circuit 300. The spectral responses are analyzed to determine one that is affected by the presence of the virus. The spectral response of the selected wavelength is analyzed to determine different patterns in shape and width indicating the presence of the virus. The pattern of the spectral response of the selected wavelength may then be mapped to the known concentration of the certain virus. This mapping may be performed for different known concentrations of the virus to generate a mapping table. The presence and/or concentration level of the virus in arterial blood flow of unknown samples may then be determined from the spectral response of the selected wavelength. This process may be performed for other types of organisms as well.

The PPG circuit 300 may thus be used to determine a concentration level of one or more substances or types of cells or organisms in arterial blood flow using the spectral responses. Such substances include but are not limited to natural and artificial occurring vasodilators, enzymes, and proteins.

The UE 100 communicates with one or more external biosensors, such as an ear biosensor and a skin biosensor, to collect and track biosensor data. The UE 100 may also include integrated biosensors.

A processing circuit includes at least one processing device, such as a microprocessor, micro-controller, digital signal processor, microcomputer, central processing unit, field programmable gate array, programmable logic device, state machine, logic circuitry, analog circuitry, digital circuitry, and/or any device that manipulates signals (analog and/or digital) based on hard coding of the circuitry and/or operational instructions. A memory is a non-transitory memory device and may be an internal memory or an external memory, and the memory may be a single memory device or a plurality of memory devices. The memory may be a read-only memory, random access memory, volatile memory, non-volatile memory, static memory, dynamic memory, flash memory, cache memory, and/or any non-transitory memory device that stores digital information.

As may be used herein, the term "operable to" or "configurable to" indicates that an element includes one or more of circuits, instructions, modules, data, input(s), output(s), etc., to perform one or more of the described or necessary corresponding functions and may further include inferred coupling to one or more other items to perform the described or necessary corresponding functions. As may also be used herein, the term(s) "coupled", "coupled to", "connected to" and/or "connecting" or "interconnecting" includes direct connection or link between nodes/devices and/or indirect connection between nodes/devices via an intervening item (e.g., an item includes, but is not limited to, a component, an element, a circuit, a module, a node, device, network element, etc.). As may further be used herein, inferred connections (i.e., where one element is connected to another element by inference) includes direct and indirect connection between two items in the same manner as "connected to".

As may be used herein, the terms "substantially" and "approximately" provides an industry-accepted tolerance for its corresponding term and/or relativity between items. Such an industry-accepted tolerance ranges from less than one percent to fifty percent and corresponds to, but is not limited to, frequencies, wavelengths, component values, integrated circuit process variations, temperature variations, rise and fall times, and/or thermal noise. Such relativity between items ranges from a difference of a few percent to magnitude differences.

Note that the aspects of the present disclosure may be described herein as a process that is depicted as a schematic, a flowchart, a flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed. A process may correspond to a method, a function, a procedure, a subroutine, a subprogram, etc. When a process corresponds to a function, its termination corresponds to a return of the function to the calling function or the main function.

The various features of the disclosure described herein can be implemented in different systems and devices without departing from the disclosure. It should be noted that the foregoing aspects of the disclosure are merely examples and are not to be construed as limiting the disclosure. The description of the aspects of the present disclosure is intended to be illustrative, and not to limit the scope of the claims. As such, the present teachings can be readily applied to other types of apparatuses and many alternatives, modifications, and variations will be apparent to those skilled in the art.

In the foregoing specification, certain representative aspects of the invention have been described with reference to specific examples. Various modifications and changes may be made, however, without departing from the scope of the present invention as set forth in the claims. The specification and figures are illustrative, rather than restrictive, and modifications are intended to be included within the scope of the present invention. Accordingly, the scope of the invention should be determined by the claims and their legal equivalents rather than by merely the examples described. For example, the components and/or elements recited in any apparatus claims may be assembled or otherwise operationally configured in a variety of permutations and are accordingly not limited to the specific configuration recited in the claims.

Furthermore, certain benefits, other advantages and solutions to problems have been described above with regard to particular embodiments; however, any benefit, advantage, solution to a problem, or any element that may cause any particular benefit, advantage, or solution to occur or to become more pronounced are not to be construed as critical, required, or essential features or components of any or all the claims.

As used herein, the terms "comprise," "comprises," "comprising," "having," "including," "includes" or any variation thereof, are intended to reference a nonexclusive inclusion, such that a process, method, article, composition or apparatus that comprises a list of elements does not include only those elements recited, but may also include other elements not expressly listed or inherent to such process, method, article, composition, or apparatus. Other combinations and/or modifications of the above-described structures, arrangements, applications, proportions, elements, materials, or components used in the practice of the present invention, in addition to those not specifically recited, may be varied or otherwise particularly adapted to specific environments, manufacturing specifications, design parameters, or other operating requirements without departing from the general principles of the same.

Moreover, reference to an element in the singular is not intended to mean "one and only one" unless specifically so stated, but rather "one or more." Unless specifically stated otherwise, the term "some" refers to one or more. All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is intended to be construed under the provisions of 35 U.S.C. § 112(f) as a "means-plus-function" type element, unless the element is expressly recited using the phrase "means for" or, in the case of a method claim, the element is recited using the phrase "step for."

What is claimed is:

1. User equipment, comprising:
   a display;
   at least one transceiver configured to communicate with an external biosensor, wherein the at least one transceiver receives biosensor data from the biosensor, wherein the biosensor data includes a first photoplethysmography (PPG) signal at a first wavelength of light and a second PPG signal at a second wavelength of light;
   at least one processing circuit and at least one memory device, wherein the at least one memory device stores instructions which when executed by the at least one processing device, causes the user equipment to:
      process the biosensor data to determine a relative alternating current (AC) component and a direct current (DC) component of the first wavelength of light and the second wavelength of light;
      determine a level of nitric oxide (NO) in blood flow based on the relative AC component and the DC component of the first wavelength of light and the second wavelength of light; and
      generate a graphical user interface (GUI) that displays the biosensor data on the display of the user equipment.

2. The user equipment of claim 1, wherein the user equipment is further configured to:
   generate a GUI that displays one or more commands for controlling the biosensor;
   receive user input indicating a command for the biosensor; and
   transmit a command to the biosensor in response to the user input.

3. The user equipment of claim 1, wherein the first wavelength of light has a high absorption coefficient for nitric oxide (NO) levels in blood flow and the second wavelength of light has a low absorption coefficient for NO levels in blood flow.

4. The user equipment of claim 3, wherein the user equipment is further configured to:
   obtain a first wavelength value ($L_{\lambda 1}$) using the first PPG signal;
   obtain a second wavelength value ($L_{\lambda 2}$) using the second PPG signal; and
   determine a ratio value ($R_{\lambda 1, \lambda 2}$) using a ratio including the value La and the value $L_{\lambda 2}$.

5. The user equipment of claim 4, wherein the user equipment is further configured to:
   determine a level of nitric oxide (NO) in blood flow using at least the value $R_{\lambda 1, \lambda 2}$.

6. The user equipment of claim 4, wherein the user equipment is further configured to:
   obtain a blood glucose concentration level using at least the value $R_{\lambda 1, \lambda 2}$ and a calibration.

7. The user equipment of claim 1, wherein the user equipment is further configured to:
   determine a level of one or more additional substances in blood flow using the biosensor data.

8. The user equipment of claim 1, wherein the user equipment is further configured to:
   determine a level of vasodilation using the biosensor data, wherein the level of vasodilation includes a measurement of a localized change in width of a vessel from a localized relaxation of vascular muscle cells within the vessel walls.

9. The user equipment of claim 1, wherein the biosensor is implemented in a finger attachment and the user equipment includes a smart phone.

10. User equipment, comprising:
    a display;
    at least one transceiver configured to communicate over a cellular network and to an external biosensor; and
    at least one processing circuit and at least one memory device, wherein the at least one memory device stores instructions which when executed by the at least one processing device, causes the user equipment to:
       obtain a first wavelength value ($L_{\lambda 1}$) using an alternating current (AC) component and a direct current (DC) component of a first photoplethysmography (PPG) signal;
       obtain a second wavelength value ($L_{\lambda 2}$) using an AC component and a DC component of a second PPG signal;
       obtain a ratio value ($R_{\lambda 1, \lambda 2}$) from a ratio including the value La and the value $L_{\lambda 2}$;
       obtain a blood glucose level using the value $R_{\lambda 1, \lambda 2}$; and
       generate a graphical user interface that includes the blood glucose level on the display.

11. The user equipment of claim 10, wherein the first PPG signal is obtained at a first wavelength with the high absorption coefficient for nitric oxide (NO) levels in blood flow and the second PPG signal is obtained at a second wavelength with a low absorption coefficient for NO levels in blood flow.

12. The user equipment of claim 10, wherein the user equipment is further configured to:
    generate a command to a drug administrative device to administer medication.

13. The user equipment of claim 10, wherein the user equipment is configured to:

generate a message with the blood glucose level to a third party health care provider; and transmit the message over a wide area network to the third party health care provider.

14. The user equipment of claim 10, wherein the user equipment is further configured to:

determine a level of one or more additional substances in blood flow using the biosensor data.

15. The user equipment of claim 10, wherein the user equipment is further configured to:

determine a level of vasodilation using the biosensor data, wherein the level of vasodilation includes a measurement of a localized change in width of a vessel from a localized relaxation of vascular muscle cells within the vessel walls.

16. The user equipment of claim 10, wherein the biosensor is implemented in a finger attachment and the user equipment includes a smart phone.

17. User equipment, comprising:

one or more transceivers configured to communicate over a cellular network and to at least one external biosensor;

at least one processing circuit and at least one memory device, wherein the at least one memory device stores instructions which when executed by the at least one processing device, causes the user equipment to:

obtain a first AC component and a first direct current (DC) component of a first photoplethysmography (PPG) signal around a first wavelength of light (21), wherein the first wavelength of light is in a range of 370 nm to 410 nm;

obtain a second AC component and a second direct current (DC) component of a second PPG signal around a second wavelength of light (21), wherein the second wavelength of light is in an infrared (IR) range; and obtain a ratio value (R) from a ratio including the first AC component, the first DC component, the second AC component, and the second DC component.

18. The user equipment of claim 17, wherein the user equipment is further configured to:

obtain an NO level using the value $R_{\lambda 1, \lambda 2}$ and a calibration.

19. The user equipment of claim 17, wherein the user equipment is further configured to:

obtain an blood glucose level using the value $R_{\lambda 1, \lambda 2}$ and a calibration.

20. The user equipment of claim 17, wherein the user equipment is further configured to:

determine a level of vasodilation using the biosensor data, wherein the level of vasodilation includes a measurement of a localized change in width of a vessel from a localized relaxation of vascular muscle cells within the vessel walls.

* * * * *

UNITED STATES PATENT AND TRADEMARK OFFICE
CERTIFICATE OF CORRECTION

PATENT NO. : 12,376,802 B2  
APPLICATION NO. : 17/127266  
DATED : August 5, 2025  
INVENTOR(S) : Robert Steven Newberry Page 1 of 1

It is certified that error appears in the above-identified patent and that said Letters Patent is hereby corrected as shown below:

In the Claims

In Claim 17, Column 40, Line 1, after 'wavelength of light' delete "(21)" and insert -- ($\lambda 1$) --

In Claim 17, Column 40, Line 6, after 'wavelength of light' delete "(21)" and insert -- ($\lambda 1$) --

Signed and Sealed this  
Fourth Day of November, 2025

John A. Squires  
*Director of the United States Patent and Trademark Office*